(12) United States Patent
Chen et al.

(10) Patent No.: US 12,370,199 B2
(45) Date of Patent: Jul. 29, 2025

(54) FULVESTRANT FORMULATIONS AND METHODS OF THEIR USE

(71) Applicant: EAGLE PHARMACEUTICALS, INC., Woodcliff Lake, NJ (US)

(72) Inventors: Feng-Jing Chen, Irvine, CA (US); Steven L. Krill, Midland Park, NJ (US); Rama Abu Shmeis, Branchburg, NJ (US)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 0 days.

(21) Appl. No.: 17/379,534

(22) Filed: Jul. 19, 2021

(65) Prior Publication Data

US 2021/0346396 A1    Nov. 11, 2021

Related U.S. Application Data

(63) Continuation of application No. 16/099,265, filed as application No. PCT/US2017/031376 on May 5, 2017, now abandoned.

(60) Provisional application No. 62/420,555, filed on Nov. 10, 2016, provisional application No. 62/332,842, filed on May 6, 2016.

(51) Int. Cl.
| | |
|---|---|
| *A61K 31/565* | (2006.01) |
| *A61K 9/00* | (2006.01) |
| *A61K 9/08* | (2006.01) |
| *A61K 9/10* | (2006.01) |
| *A61K 9/14* | (2006.01) |
| *A61K 31/519* | (2006.01) |
| *A61K 45/06* | (2006.01) |
| *A61K 47/10* | (2017.01) |
| *A61K 47/26* | (2006.01) |
| *A61K 47/32* | (2006.01) |
| *A61P 35/00* | (2006.01) |

(52) U.S. Cl.
CPC .......... *A61K 31/565* (2013.01); *A61K 9/0019* (2013.01); *A61K 9/08* (2013.01); *A61K 9/10* (2013.01); *A61K 9/14* (2013.01); *A61K 31/519* (2013.01); *A61K 45/06* (2013.01); *A61K 47/10* (2013.01); *A61K 47/26* (2013.01); *A61K 47/32* (2013.01); *A61P 35/00* (2018.01)

(58) Field of Classification Search
CPC ...... A61K 31/565; A61K 9/0019; A61K 9/08; A61K 9/10; A61K 9/14; A61K 31/519; A61K 45/06; A61K 47/10; A61K 47/26; A61K 47/32; A61P 35/00
See application file for complete search history.

(56) References Cited

U.S. PATENT DOCUMENTS

| | | |
|---|---|---|
| 6,774,122 B2 | 8/2004 | Evans et al. |
| 7,456,160 B2 | 11/2008 | Evans et al. |
| 8,158,152 B2 | 4/2012 | Palepu |
| 8,329,680 B2 | 12/2012 | Evans et al. |
| 8,466,139 B2 | 6/2013 | Evans et al. |
| 8,541,400 B2 | 9/2013 | Johnsson et al. |
| 8,586,092 B2 | 11/2013 | Hu et al. |
| 8,853,260 B2 | 10/2014 | Desai et al. |
| 8,956,659 B2 | 2/2015 | Hu et al. |
| 9,180,088 B2 | 11/2015 | Palepu |
| 9,254,268 B2 | 2/2016 | Temtsin et al. |
| 9,271,990 B2 | 3/2016 | Faraj |
| 2001/0020016 A1 | 9/2001 | Evans et al. |
| 2003/0114430 A1 | 6/2003 | Macleod et al. |
| 2003/0165568 A1 | 9/2003 | Colombo et al. |
| 2003/0185568 A1 | 10/2003 | Ooi et al. |
| 2006/0251582 A1 | 11/2006 | Reb |
| 2007/0093547 A1 | 4/2007 | Desai et al. |
| 2008/0161276 A1 | 7/2008 | Johnsson et al. |
| 2009/0098200 A1 | 4/2009 | Temtsin et al. |
| 2010/0166872 A1 | 7/2010 | Singh et al. |
| 2010/0323020 A1 | 12/2010 | Gokhale et al. |
| 2013/0033813 A1 | 2/2013 | Ling et al. |

(Continued)

FOREIGN PATENT DOCUMENTS

| | | |
|---|---|---|
| CN | 1429101 A | 7/2003 |
| CN | 101108168 A | 1/2008 |

(Continued)

OTHER PUBLICATIONS

Addo et al., A phase 1 trial to assess the pharmacology of the new oestrogen receptor antagonist fulvestrant on the endometrium in healthy postmenopausal volunteers, British Journal of Cancer, 87, 2002, 1354-1359.

(Continued)

*Primary Examiner* — Robert A Wax
*Assistant Examiner* — Olga V. Tcherkasskaya
(74) *Attorney, Agent, or Firm* — BakerHostetler

(57) ABSTRACT

The disclosure is directed to fulvestrant formulations including suspensions of fulvestrant particles suitable for injection. The formulations can comprise fulvestrant particles having an LD Dv(10) less than about 3 microns, for example, between about 1 micron to about 3 microns, an LD Dv(50) less than about 35 microns, for example, between about 2 microns and about 35 microns, and an LD Dv(90) less than about 120 microns, for example, between about 4 microns and about 120 microns. The formulations can comprise fulvestrant particles having a CE Dv(90) less than about 200 microns, for example, between about 10 microns and about 200 microns, a CE Dv(50) less than about 60 microns, for example, between about 5 microns and about 60 microns, and a CE Dv(10) less than about 25 microns, for example, between about 1 microns and about 25 microns.

5 Claims, 18 Drawing Sheets

(56) References Cited

U.S. PATENT DOCUMENTS

| | | | |
|---|---|---|---|
| 2013/0267489 | A1 | 10/2013 | Teja et al. |
| 2013/0274236 | A1 | 10/2013 | Swart |
| 2013/0338131 | A1 | 12/2013 | Staric et al. |
| 2014/0088061 | A1 | 3/2014 | Castillo et al. |
| 2014/0314664 | A1 | 10/2014 | Qin et al. |
| 2015/0104521 | A1 | 4/2015 | Desai et al. |
| 2015/0132388 | A1 | 5/2015 | Angi et al. |
| 2015/0231153 | A1 | 8/2015 | Faraj |
| 2016/0058773 | A1 | 3/2016 | Palepu |
| 2016/0129014 | A1 | 5/2016 | Faraj |
| 2016/0220505 | A1 | 8/2016 | Temtsin et al. |

FOREIGN PATENT DOCUMENTS

| | | |
|---|---|---|
| CN | 102802609 A | 11/2012 |
| CN | 104337761 A | 2/2015 |
| EP | 1962906 | 9/2008 |
| EP | 2200588 | 6/2010 |
| EP | 2249839 | 11/2010 |
| EP | 2460539 A1 | 6/2012 |
| EP | 2601935 A1 | 6/2013 |
| EP | 2616078 | 7/2013 |
| EP | 2661281 | 11/2013 |
| EP | 3068377 | 9/2016 |
| JP | 2003-519659 A | 6/2003 |
| JP | 2004-534093 A | 11/2004 |
| TW | 201016220 A | 5/2010 |
| WO | 01/87266 A1 | 11/2001 |
| WO | 03/06064 | 1/2003 |
| WO | 2006/013369 A2 | 2/2006 |
| WO | 2007/061529 A1 | 5/2007 |
| WO | 2007/069272 A2 | 6/2007 |
| WO | 2009/040818 A1 | 4/2009 |
| WO | 2009/111057 A2 | 9/2009 |
| WO | 2010/147899 A1 | 12/2010 |
| WO | 2012/021791 A2 | 2/2012 |
| WO | 2012/035516 A1 | 3/2012 |
| WO | 2012/094620 A2 | 7/2012 |
| WO | 2013/153559 A1 | 10/2013 |
| WO | 2015/033302 A2 | 3/2015 |
| WO | 2015/051193 A1 | 4/2015 |
| WO | 2015/071836 A1 | 5/2015 |
| WO | 2015/114320 A1 | 8/2015 |
| WO | 2016/000653 A1 | 1/2016 |
| WO | 2016/004369 A1 | 1/2016 |

OTHER PUBLICATIONS

Ballard, B., "Biopharmaceutical considerations in subcutaneous and intramuscular drug administration", Journal of Pharmaceutical Sciences, 1968, 57(3):357-378.
Behre, H., et al., "Intramuscular injection of testosterone undecanoate for the treatment of male hypogonadism: phase I studies", 1999, 140(5):414-419.
Brunner, N. "MCF7/LCC2: a 4-hydroxytamoxifen resistant human breast cancer variant that retains sensitivity to the steroidal antiestrogen ICI 182,780", Cancer Res. 1993, 53(14):3229-3232.
Chatterjee et al., Contrasting action of antiestrogen (ICI-182780) for preventing initiation of embryo implantation by estradiol or epidermal growth factor (EGF). Life sciences, Jan. 1, 1993;53(21):1625-1630.
DeFriend et al., Investigation of a new pure antiestrogen (ICI 182780) in women with primary breast cancer. Cancer Research. Jan. 15, 1994;54(2):408-414.
Dukes et al., Antiuterotrophic effects of a pure antioestrogen, ICI 182,780: magnetic resonance imaging of the uterus in ovariectomized monkeys, Journal of Endocrinology. Nov. 1, 1992;135(2):239-247.
Dukes et al., Antiuterotrophic effects of the pure antioestrogen ICI 182,780 in adult female monkeys (*Macaca nemestrina*): quantitative magnetic resonance imaging. Journal of Endocrinology, Aug. 1, 1993;138(2):203-209.

Gallagher et al., The estrogen antagonist ICI 182,780 reduces cancellous bone volume in female rats. Endocrinology. Dec. 1, 1993;133(6):2787-2791.
Gradishar et al., Clinical potential of new antiestrogens. Journal of Clinical Oncology. Feb. 1997;15(2):840-852.
Gunther et al., The effects of the estrogen receptor blocker, Faslodex (ICI 182,780), on estrogen-accelerated bone maturation in mice. Pediatric research. Sep. 1999;46(3):269-273.
Howell et al., Clinical studies with the specific 'pure' antioestrogen ICI 182780. The Breast. Jun. 1, 1996;5(3):192-195.
Hu et al., Circumvention of tamoxifen resistance by the pure anti-estrogen ICI 182, 780. International journal of cancer, Nov. 11, 1993;55(5):873-876.
ISO 13320, International Standard, Particle size analysis—Laser diffraction methods; First edition, Oct. 1, 2009, 58 pages.
Kern, F. et al., "Transfected MCF-7 cells as a model for breast cancer progression", Breast Cancer Research and Treatment, 1994, 153-165.
Kuter et al., Pharmacokinetic profile of fulvestrant 500 mg vs 250 mg: Results from the NEWEST study, Journal of Clinical Oncology, 2008 ASCO Annual Meeting Proceedings (Post-Meeting Edition), vol. 26, No. 15S, (May 20 Supplement), 2008, 579.
Langdon, S. et al., "Growth inhibition of oestrogen receptor-positive human ovarian carcinoma by anti-oestrogens in vitro and in a xenograft model", Eur J Cancer, 1994, 682-686.
McClelland, R. et al., "Effects of short-term antiestrogen treatment of primary breast cancer on estrogen receptor mRNA and protein expression and on estrogen-regulated genes", Breast Cancer Research Treatment, 1996, 41(1):31-41.
McClelland, R. et al., "Short-term effects of pure anti-oestrogen ICI 182780 treatment on oestrogen receptor, epidermal growth factor receptor and transforming growth factor-alpha protein expression in human breast cancer", Eur J Cancer, 1996, 32A(3):413-416.
Minto, C., et al., "Pharmacokinetics and pharmacodynamics of nandrolone esters in oil vehicle: effects of ester, injection site and injection volume", The Journal of Pharmacology and Experimental Therapeutics, 1997, 281(1):93-102.
Nicholson, R. et al., "Responses to pure antiestrogens (ICI 164384, ICI 182780) in estrogen-sensitive and -resistant experimental and clinical breast cancer", Annals New York Academy of Sciences, 1995, 12;761:148-163.
Ogasawara, Y. et al., "Effects of experimental chemoendocrine therapy with a combination of a pure antiestrogen and 5-fluorouracil on human breast cancer cells implanted in nude mice", Surgery Today, 1999, 29, 149-156.
Ohno et al., Three dose regimens of fulvestrant in postmenopausal Japanese women with advanced breast cancer: results from a double-blind, phase II comparative study (FINDER1), Annals of Oncology 21: 2342-2347, 2010.
Osborne, C. et al., "Comparison of the Effects of a Pure Steroidal antiestrogen With Those of Tamoxifen in a Model of Human Breast Cancer", Journal of the National Cancer Institute, 1995, 746-750.
Osborne, C., et al., "The importance of tamoxifen metabolism in tamoxifen-stimulated breast tumor growth", Cancer Chemother Pharmacol, 1994, 89-95.
Parczyk, K., et al., "Progesterone receptor repression by estrogens in rat uterine epithelial cells", J Steroid Biochem Mol Biol., 1997, 63(4-6):309-316.
Parisot, J. et al., "The pure antiestrogen ICI 182,780 binds to a high-affinity site distinct from the estrogen receptor", Int J Cancer, 1995, 62(4):480-4.
Robertson et all., Pharmacokinetic Profile of Intramuscular Fulvestrant in Advanced Breast Cancer, Clin. Pharmacokinet, 43(8), 2004, 529-538.
Robertson, Fulvestrant: pharmacokinetics and pharmacology; British Journal of Cancer, 90 (Suppl I), 2004, S7-S10.
Sahlin, L., et al., "Regulation of thioredoxin mRNA in the rat uterus by gonadal steroids", Journal of Steroid Biochemistry & Molecular Biology, 1999, 68(5-6):203-209.
Spiegel, A., et al., "Use of Nonaqueous Solvents in Parenteral Products", Journal of Pharmaceutical Sciences, 1963, 52, 917-927.
Thurlimann, B., "Hormonal treatment of breast cancer: new developments", Oncology, 1998, 55(6):501-507.

(56) References Cited

OTHER PUBLICATIONS

Vollmer, G., et al., "The rat endometrial adenocarcinoma cell line RUCA-I: a novel hormone-responsive in vivo/in vitro tumor model", J Steroid Biochem Mol Biol. 1996, 58(1):103-115.

Von Minckwitz, G. et al., "New endocrine approaches in the treatment of breast cancer", Biomed Pharmacother, 1998, 52(3):122-132.

Wakeling AE. A new approach to breast cancer therapy: Total estrogen ablation with pure antiestrogens, Long-Term Tamoxifen Treatment for Breast Cancer, ed Jordan VC (University of Wisconsin Press, Madison). 1994:219-234.

Wakeling, A., "Are breast tumours resistant to tamoxifen also resistant to pure antioestrogens?", The Journal of Steroid Biochemistry and Molecular Biology, 1993, 107-114.

Wakeling, A., "Interactions Between Growth Factors and Oestrogens in Breast Cancer Cells", Molecular Oncology and Clinical Applications, 1993, 385-389.

Wakeling, A., "The future of new pure antiestrogens in clinical breast cancer", Breast Cancer Res Treat. 1993, 25(1):1-9.

Wakeling, A., "Development of novel oestrogen-receptor antagonists", Biochem Soc Trans, 1991, 19(4):899-901.

Wakeling, A., et al., "ICI 182,780, a new antioestrogen with clinical potential", J Steroid Biochem Mol Biol. 1992, 43(1-3):173-177.

Wilson, J. et al., "MCF-7 human mammary adenocarcinoma cell death in vitro in response to hormone-withdrawal and DNA damage", Int J Cancer, 1995 , 61(4):502-508.

Zalcberg, J. et al., "Differential effects of estrogen, tamoxifen and the pure antiestrogen ICI 182,780 in human drug-resistant leukemia cell lines", Cancer Chemother Pharmacol. 1993;33(2):123-129.

"Polyethylene Glycol 3350 NF Polyethylene Glycol 3350 Powder for Oral Solution", Retrieved from https://dailymed.nlm.nih.gov/dailymed/fda/fdaDrugXsl.cfm?setid=ef00202d-7a97-43df-adc7-c4043b54df03, Retrieved on Feb. 18, 2025, pp. 1-6.

"Polyethylene Glycol 3350", Revision Bulletin, Dec. 1, 2020, 7 Pages.

Formulation F003a-100mg/ml Fulvestrant Suspension

| | Materials | Process Step | In-Process Control & Testing | Note |
|---|---|---|---|---|
| Step1 | Purified Water Polysorbate 80 | Mix | Very sufficient mixing | Clear |
| Step2 | Fulvestrant | Homogenize with IKA T10 @25000 rpm for 60-120 min. | Particle Size (via laser diffraction) | LD $Dv_{90}$ ~12μm |
| Step3 | | Combine 4 sublots. Mix with Vortex Mixer | Particle Size (via laser diffraction) | LD $Dv_{90}$ ~13μm |
| Step4 | Dextrose | Mix with Vortex Mixer | Particle Size (via laser diffraction) | LD $Dv_{90}$ ~13μm |

*FIG. 4*

Formulation F003b-100mg/ml Fulvestrant Suspension

| | Materials | Process Step | In-Process Control & Testing | Note |
|---|---|---|---|---|
| Step1 | Purified Water Polysorbate 80 | Mix | Very sufficient mixing | Clear |
| Step2 | Fulvestrant | Homogenize with IKA T10 @25000 rpm for 15 min. (3 sublots) | Particle Size (via laser diffraction) | LD $Dv_{90}$~40μm |
| Step3 | | Combine 3 sublots. Mix with Vortex Mixer | Particle Size (via laser diffraction) | LD $Dv_{90}$~40μm |
| Step4 | | Process with Nano DeBee Z5 @40000 psi for 15 cycles | Particle Size (via laser diffraction) | LD $Dv_{90}$~15μm |
| Step5 | | Remove 12% supernatant | | |
| Step6 | Dextrose | Mix with Vortex Mixer | Particle Size (via laser diffraction) | LD $Dv_{90}$~12μm |

FIG. 5

Formulation F005c-100mg/ml Fulvestrant Suspension

| | Materials | Process Step | In-Process Control & Testing | Note |
|---|---|---|---|---|
| Step1 | Purified Water Polysorbate 80 | Mix | Very sufficient mixing | Clear |
| Step2 | Fulvestrant | Homogenize with IKA T10 @25000 rpm for 15 min. (3 sublots) | Particle Size (via laser diffraction) | LD $Dv_{90}$~40μm |
| Step3 | | Combine 3 sublots. Mix with Vortex Mixer | Particle Size (via laser diffraction) | LD $Dv_{90}$~40μm |
| Step4 | | Process with Nano DeBee Z5 @40000 psi for 15 cycles | Particle Size (via laser diffraction) | LD $Dv_{90}$~15μm |
| Step5 | | Remove 12% supernatant | | |
| Step6 | Mannitol | Mix with Vortex Mixer | Particle Size (via laser diffraction) | LD $Dv_{90}$~12μm |

*FIG. 6*

Formulation F003d-100mg/ml Fulvestrant Suspension

Formulation F003e-100mg/ml Fulvestrant Suspension

| | Materials | Process Step | In-Process Control & Testing | Note |
|---|---|---|---|---|
| Step 1 | Purified Water Polysorbate 80 | Mix | Very sufficient mixing | Clear |
| Step 2 | Micronized Fulvestrant | Homogenize with IKA T10 @25000 rpm for 5 min. | Particle Size (via laser diffraction) | LD $Dv_{90}$~12μm |
| Step 3 | Dextrose | Mix with Vortex Mixer | Particle Size (via laser diffraction) | LD $Dv_{90}$~13μm |
| Step 4 | F003d | Mix with Vortex Mixer | Particle Size (via laser diffraction) | LD $Dv_{90}$~13μm |

FIG. 8

Formulation F003k3-100mg/ml Fulvestrant Suspension

| | Materials | Process Step | In-Process Control & Testing | Note |
|---|---|---|---|---|
| Step1 | Purified Water Polysorbate 80 Dextrose | Mix | Very sufficient mixing | Clear |
| Step2 | Micronized Fulvestrant | Homogenize with IKA T10 @25000 rpm for 5 min. | Particle Size (via laser diffraction) | LD $Dv_{90}$~9μm |
| Step3 | | Process with Nano DeBee Z5 @40000 psi for 9 cycles | Particle Size (via laser diffraction) | LD $Dv_{90}$~13μm |
| Step4 | | Add 10ml vehicle to pump all suspension out | Assay | ~79 mg/ml |
| Step5 | | Remove 21% supernatant | Particle Size (via laser diffraction) | LD $Dv_{90}$~13μm |

*FIG. 10*

Formulation F005c2-100mg/ml Fulvestrant Suspension

| | Materials | Process Step | In-Process Control & Testing | Note |
|---|---|---|---|---|
| Step 1 | Purified Water, Polysorbate 80, Mannitol | Mix | Very sufficient mixing | Clear |
| Step 2 | Micronized Fulvestrant | Homogenize with IKA T10 @25000 rpm for 5 min. | Particle Size (via laser diffraction) | LD $Dv_{90}$ ~9μm |
| Step 3 | | Process with Nano DeBee Z5 @40000 psi for 9 cycles | Particle Size (via laser diffraction) | LD $Dv_{90}$ ~13μm |
| Step 4 | | Add 10ml vehicle to pump all suspension out | Assay | ~79 mg/ml |
| Step 5 | | Remove 21% supernatant | Particle Size (via laser diffraction) | LD $Dv_{90}$ ~13μm |

*FIG. 11*

Formulation F005b1(5mg/mL_PS80), F017a(15mg/mL_PS80), F015a(25mg/mL_PS80) -100mg/ml Fulvestrant Suspension directly by dispersing the micronized API in suspending medium only

| Materials | Process Step | In-Process Control & Testing | Note |
|---|---|---|---|
| Step 1: Purified Water, Polysorbate 80, Mannitol | Mix | Very sufficient mixing | Clear |
| Step 2: Micronized Fulvestrant | Homogenize with IKA T10 @25000 rpm for 5 min. | Particle Size (via laser diffraction) | LD $Dv_{90}$ ~7μm |

*FIG. 12*

FULVESTRANT FORMULATIONS AND METHODS OF THEIR USE

CROSS REFERENCE TO RELATED APPLICATIONS

This application is a continuation of U.S. application Ser. No. 16/099,265, filed Nov. 6, 2018 which is a National Stage Application filed under 35 U.S.C. 371 of International Application No. PCT/US2017/031376 filed May 5, 2017 which claims the benefit of U.S. Provisional Application No. 62/332,842, filed May 6, 2016, and U.S. Provisional Application No. 62/420,555, filed Nov. 10, 2016, the entireties of which are incorporated by reference herein.

FIELD

The disclosure is directed to fulvestrant-containing formulations and methods of their use in the treatment of disease.

BACKGROUND

Fulvestrant, or 7-(9-(4,4,5,5,5-pentafluoropentylsulfinyl)nonyl)estra-1,3,5(10)-triene-3,17-diol, has the structure of formula (1):

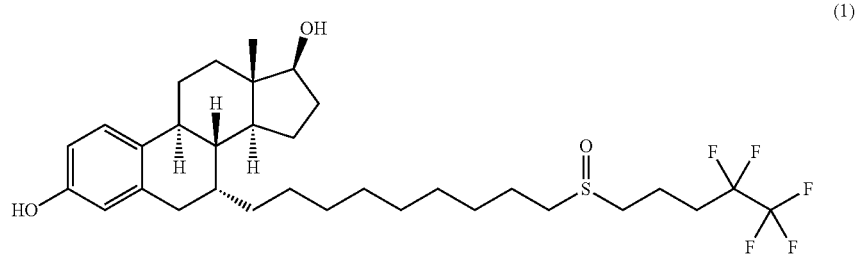

(1)

Fulvestrant is a selective estrogen receptor degrader (SERD) indicated for the treatment of hormone receptor positive metastatic breast cancer in postmenopausal women with disease progression following anti-estrogen therapy.

As with other steroidal-like compounds, fulvestrant has physical properties which make preparing fulvestrant pharmaceutical compositions difficult. Fulvestrant is a particularly lipophilic molecule, even when compared with other steroidal compounds, and its aqueous solubility is extremely low.

Due to the poor solubility and oral bioavailability of fulvestrant, the drug is currently administered via intramuscular injection of an oil-based fulvestrant formulation. The current commercial formulation of fulvestrant, FASLODEX™, is dosed at 500 mg and requires that two 5 mL injections of a 50 mg/mL fulvestrant formulation be administered intramuscularly. Each 5 mL injection contains 10% w/v alcohol, 10% w/v benzyl alcohol, and 15% w/v benzyl benzoate as co-solvents and made up to 100% w/v with castor oil as a further co-solvent and release rate modifier. Administration of the formulation is slow (1-2 minutes per injection) and painful, due to the viscous oil-based vehicle used to solubilize fulvestrant. A warning has been added to the FASLODEX™ label concerning painful injections, sciatica, neuropathic pain, and peripheral neuropathy.

It has been previously reported (U.S. Pat. No. 6,774,122 to AstraZeneca) that intra-muscular injections of fulvestrant in the form of an aqueous suspension were not suitable for use. Those suspensions resulted in extensive local tissue irritation at the injection site as well as a poor release profile due to the presence of fulvestrant in the form of solid particles. Furthermore, the fulvestrant release rate was reported as not clinically significant.

There is a need for fulvestrant formulations with improved dosing properties. The disclosure is directed to these and other important needs.

SUMMARY

The present disclosure provides formulations comprising fulvestrant particles. The disclosure also provides fulvestrant suspensions, preferably those having a fulvestrant concentration of equal to or greater than about 50 mg/mL. The disclosure also provides formulations comprising fulvestrant particles and a non-oil vehicle. Some aspects of the disclosure are directed to pharmaceutical compositions comprising fulvestrant particles having an LD Dv(90) greater than or equal to about 7 microns. Further aspects of the disclosure are directed to pharmaceutical compositions comprising fulvestrant particles having a CE Dv(90) less than about 200 microns, for example, between about 10 microns and about 200 microns, a CE Dv(50) less than about 60 microns, for example, between about 5 microns and about 60 microns, and a CE Dv(10) less than 25 microns, for example, between about 1 microns and about 25 microns. Other aspects of the disclosure are directed to pharmaceutical compositions comprising fulvestrant at a concentration of about 100 mg/mL, whereupon administration to a subject, the 90% confidence intervals (CI) of the relative mean $AUC_{(0-t)}$, relative mean $AUC_{(0-\infty)}$, or both of the pharmaceutical compositions of the disclosure is within 80% to 125% of the relative mean $AUC_{(0-t)}$ and relative mean $AUC_{(0-\infty)}$, respectively, of a reference listed fulvestrant product. Other aspects of the disclosure are directed to fulvestrant formulations having a concentration of about 100 mg/mL and particular pharmacokinetic profiles. In other aspects, the disclosure is directed to pharmaceutical compositions comprising fulvestrant particles, wherein the fulvestrant concentration is about 40 to 125 mg/mL.

Methods of making and using the products described herein are also described.

BRIEF DESCRIPTION OF THE DRAWINGS

The summary, as well as the following detailed description, is further understood when read in conjunction with the appended drawings. For the purpose of illustrating the disclosure, there are shown in the drawings exemplary embodiments of the disclosure; however, the disclosure is not limited to the specific methods, compositions, and devices disclosed. In the drawings:

FIG. 4 depicts aspects of exemplary methods of preparation for fulvestrant suspensions of the present disclosure;

FIG. 5 depicts aspects of exemplary methods of preparation for fulvestrant suspensions of the present disclosure;

FIG. 6 depicts aspects of exemplary methods of preparation for fulvestrant suspensions of the present disclosure;

FIG. 8 depicts aspects of exemplary methods of preparation for fulvestrant suspensions of the present disclosure;

FIG. 10 depicts aspects of exemplary methods of preparation for fulvestrant suspensions of the present disclosure;

FIG. 11 depicts aspects of exemplary methods of preparation for fulvestrant suspensions of the present disclosure;

FIG. 12 depicts aspects of exemplary methods of preparation for fulvestrant suspensions of the present disclosure;

Figure 1A:
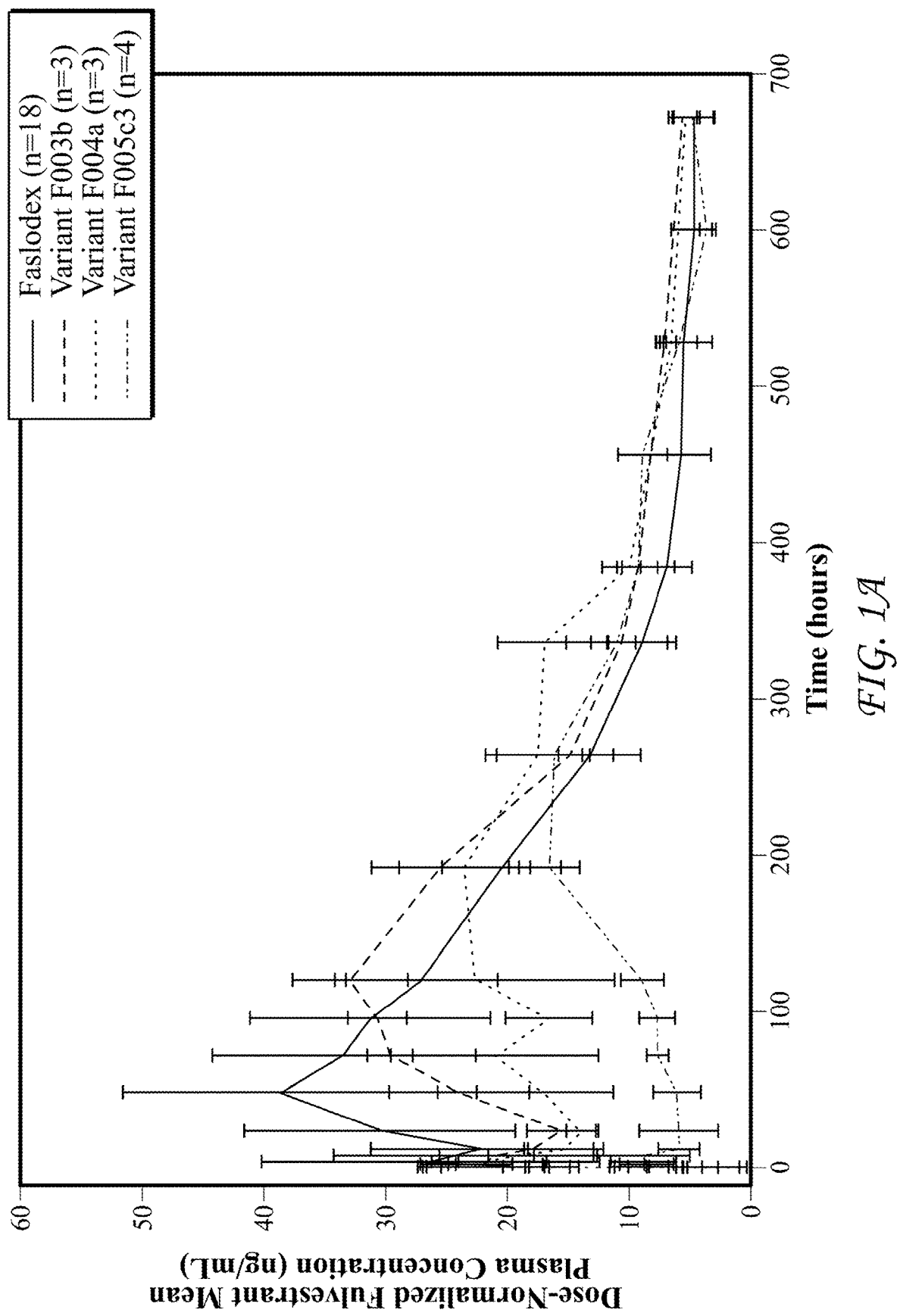
FIG. 1A depicts pharmacokinetic data for administration of commercial fulvestrant formulations (FASLODEX™) and some exemplary fulvestrant formulations of the present disclosure to canines.
Figure 1B:
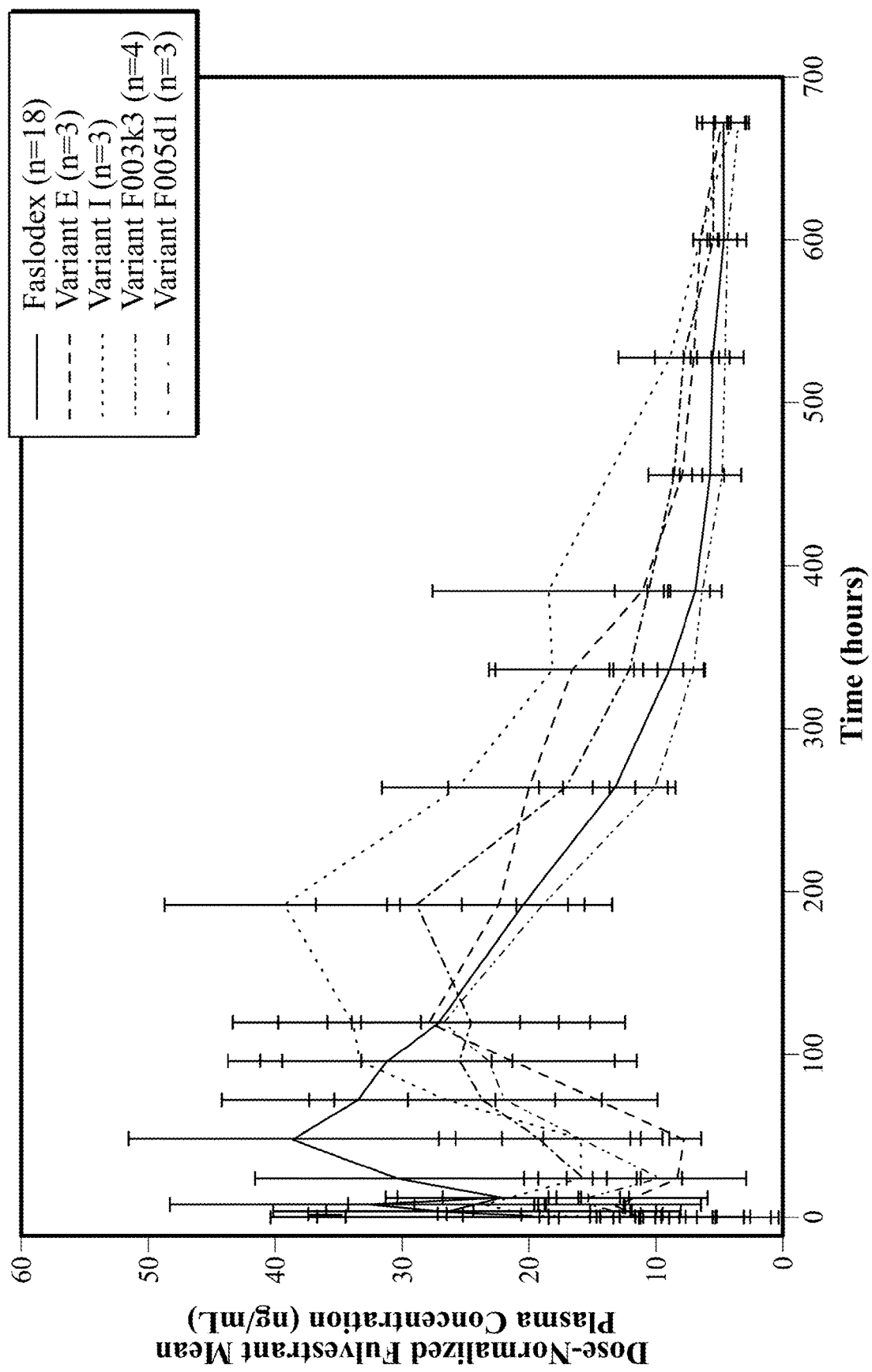
FIG. 1B depicts pharmacokinetic data for administration of commercial fulvestrant formulations (FASLODEX™) and some exemplary fulvestrant formulations of the present disclosure to canines.

All callouts and annotations in the Figures are hereby incorporated into this description as if fully set forth herein.

DETAILED DESCRIPTION OF ILLUSTRATIVE EMBODIMENTS

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claimed disclosure.

As used in the specification including the appended claims, the singular forms "a," "an," and "the" include the plural, and reference to a particular numerical value includes at least that particular value, unless the context clearly dictates otherwise.

When a range of values is expressed, another embodiment includes from the one particular value and/or to the other particular value. All ranges are inclusive and combinable. Further, reference to values stated in ranges include each and every value within that range. When values are expressed as approximations, by use of the antecedent "about," it will be understood that the particular value forms another embodiment. The term "about" as used herein when referring to a measurable value such as an amount, a temporal duration, and the like, is meant to encompass reasonable variations of the value, such as, for example, ±10% from the specified value. For example, the phrase "about 50%" can include ±10% of 50, or from 45% to 55%.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination.

Terms

As used herein, whether by itself or in conjunction with another term or terms, it should be understood that the phrases "method of treating" and "method of treatment" may be used interchangeably with the phrase "for use in the treatment of" a particular disease.

As used herein, whether by itself or in conjunction with another term or terms, "pharmaceutically acceptable" indicates that the designated entity such as, for example, e.g., a pharmaceutically acceptable excipient is generally chemically and/or physically compatible with other ingredients in a formulation, and/or is generally physiologically compatible with the recipient thereof.

As used herein, "pharmaceutical composition" refers to a formulation as described herein that includes one or more pharmaceutically acceptable excipients, that is suitable for administration to a subject. It should be understood that the term "pharmaceutical composition" encompasses (a) suspensions and (b) suspensions which have been dried such that one or more solvents have been removed partially or completely, either by evaporation or sublimation, including, but not limited to, lyophilized cakes.

As used herein, whether by themselves or in conjunction with another term or terms, "subject(s)," "individual(s)," and "patient(s)", refer to mammals, including humans. The term human(s) refers to and includes, a human child, adolescent, or adult.

As used herein, whether by themselves or in conjunction with another term or terms, "treats," "treating," "treated," and "treatment," refer to and include ameliorative, palliative, and/or curative uses and results, or any combination thereof. In other embodiments, the methods described herein can be used prophylactically. It should be understood that "prophylaxis" or a prophylactic use or result do not refer to nor require absolute or total prevention (i.e., a 100% preventative or protective use or result). As used herein, prophylaxis or a prophylactic use or result refer to uses and results in which administration of a compound or formulation diminishes or reduces the severity of a particular condition, symptom, disorder, or disease described herein; diminishes or reduces the likelihood of experiencing a particular condition, symptom, disorder, or disease described herein; or delays the onset or relapse (reoccurrence) of a particular condition, symptom, disorder, or disease described herein; or any combination of the foregoing.

As used herein, whether used alone or in conjunction with another term or terms, "therapeutic" and "therapeutically effective amount", refer to an amount of a compound or formulation that (a) treats a particular condition, symptom, disorder, or disease described herein; (b) attenuates, ameliorates or eliminates one or more symptoms of a particular condition, disorder, or disease described herein; (c) delays the onset or relapse (reoccurrence) of a particular condition, symptom, disorder, or disease described herein. It should be understood that the terms "therapeutic" and "therapeutically effective" encompass any one of the aforementioned effects (a)-(c), either alone or in combination with any of the others (a)-(c).

As used herein, whether used alone or in conjunction with another term or terms, "therapeutic agent" refers to any substance included in a formulation that is useful in the treatment of a disease, condition, or disorder or comorbidity (i.e., a disease, condition, or disorder that exists simultaneously with breast cancer) and is not fulvestrant.

As used herein, whether used alone or in conjunction with another term or terms, "suspension" refers to solid particles dispersed in a liquid vehicle.

As used herein, whether used alone or in conjunction with another term or terms, "formulation" refers to a mixture of components. The term "formulation" encompasses pharmaceutical compositions, and suspensions, as well as suspensions that have been dried such that one or more solvents have been removed partially or completely (e.g., lyophilized cakes).

As used herein "Dv(10)", "Dv(50)" and "Dv(90)" are defined as the volume weighted particle diameters where a cumulative 10%, 50% or 90% v/v of the particles have an equal or smaller diameter, respectively, when measured. For example, if a particle population has a Dv(50) of about 25 microns, 50% of the particles in volume have a diameter of less than or equal to about 25 microns.

As used herein, Dn(10)", "Dn(50)" and "Dn(90)" are defined as the number weighted particle diameters where a cumulative 10%, 50% or 90% of the particles have an equal or smaller diameter, respectively, when measured. For example, if a particle population has a Dn(50) of about 25 microns, 50% of the particles in number have a diameter of less than or equal to about 25 microns.

Particle size and particle size distributions can be determined by measurement via laser diffraction. Particle size analysis by laser diffraction methods is known in the art and is explained more fully by ISO 13320:2009(E), "Particle size analysis—Laser diffraction methods," International Organization for Standardization which is incorporated by reference herein in its entirety for all purposes. Particle sizes determined by laser diffraction are represented as the diameter of a sphere having equivalent volume to the particle volume as determined by Mie theory of light scattering. Tables 1-7 and 23-27 and FIGS. 4-12 provide laser diffraction particle size and particle size distribution ("PSD") data for some exemplary embodiments of the present invention, with measurements taken during methods of preparation, on the day of formulation ("Day 0"), and at various later dates after formulation, as indicated. Measurements were taken "as is" and "sonicated." Data for "sonicated" samples indicates that the measurement sample was subjected to sonication to disperse agglomerates and provide stable repeat measurements, as more fully described in ISO 13320:2009 (E). Values measured via laser diffraction are indicated as such in the Figures and Tables, or are referred to herein by "laser diffraction Dv(##)", "LD Dv(##)", "laser diffraction diameter", or "LD diameter."

Particle size and particle size distributions can also be determined by microscopy image capture and analysis. Microscopy image capture and analysis captures a two dimensional (2D) image of a 3D particle and calculates various size and shape parameters from the 2D image. Particle sizes determined by microscopy image capture and analysis are represented as the diameter of a circle with the equivalent area as the 2D image of the particle, referred to herein as a circle equivalent or "CE" diameter. Particle size analysis by microscopy image capture and analysis is known in the art and is explained more fully by ISO 13322-1:2014, "Particle size analysis—Image analysis methods—Part 1: Static image analysis methods," International Organization for Standardization, which is incorporated by reference herein in its entirety for all purposes. Values measured by microscopy image capture and analysis are referred to herein by "circle equivalent diameter," "CE diameter," "circle equivalent Dv(##)," "CE Dv(##)", or "CE Dn(##)". Tables 41-50 provide microscopy image capture and analysis particle size and particle size distribution data for some exemplary embodiments of the present invention, with measurement samples taken during methods of preparation, after an initial suspension is formed, or after lyophilization and reconstitution, as indicated.

A. Formulations

Suspensions Comprising Fulvestrant Particles and a Vehicle

In particular embodiments, the invention is directed to suspensions comprising fulvestrant particles and a vehicle. The fulvestrant particles may have different particle size distributions as described more fully elsewhere herein. As used herein, a "vehicle" is a suspending medium, preferably a pharmaceutically acceptable suspending medium. In certain embodiments, the vehicle is a non-oil vehicle. As used herein, "oils" are non-polar substances that have no or low miscibility with water. Castor oil is an example of an oil. In other embodiments of the invention, the vehicle comprises water, i.e., is aqueous. As used herein, an "aqueous" vehicle is a vehicle that comprises at least about 50% w/w water. In some embodiments, the aqueous vehicle comprises at least about 60% w/w, at least about 70% w/w, at least about 80% w/w, at least about 85% w/w, at least about 90% w/w, at least about 95% w/w, at least about 96% w/w, at least about 97% w/w, at least about 98% w/w, or at least about 99% w/w water. In certain embodiments of the invention, the vehicle is water. In yet other embodiments of the invention, the vehicle is a non-aqueous medium. In some embodiments, a vehicle comprises a single suspending medium. In other embodiments, a vehicle comprises a mixture of two or more suspending mediums, which may be aqueous or non-aqueous. In still other embodiments of the invention, the vehicle comprises both water and a non-aqueous solvent. In particular embodiments of the invention, the suspension is substantially oil-free. As used herein, a "substantially oil-free" suspension is a suspension comprising a vehicle that comprises at most about 10% w/w oil. In some preferred embodiments, a substantially oil-free suspension comprises a vehicle that comprises less than about 5% w/w oil, less than about 2% w/w oil, less than about 1% w/w oil, less than about 0.5% w/w oil, less than about 0.1% w/w oil, or comprises a vehicle that is free of oil.

Fulvestrant suspensions of the disclosure can have fulvestrant present at a concentration of about 40 mg/mL to about 125 mg/mL in a vehicle. The fulvestrant present in the fulvestrant suspensions may have different particle size distributions as described more fully elsewhere herein. In particular embodiments of the invention, fulvestrant is present at a concentration equal to or greater than about 40 mg/mL. In further embodiments, fulvestrant is present at a concentration of about 40 to about 75 mg/mL. In other embodiments, fulvestrant is present at a concentration of about 75 mg/mL to about 125 mg/mL. In still further embodiments, fulvestrant is present at a concentration of about 40 mg/mL, about 45 mg/mL, about 50 mg/mL, about 55 mg/mL, about 60 mg/mL, about 65 mg/mL, about 70 mg/mL, or about 75 mg/mL.

In certain embodiments, fulvestrant is present in the suspension at a concentration equal to or greater than about 75 mg/mL. In further embodiments, fulvestrant is present in the suspension at a concentration of about 75 to about 125 mg/mL. In particular embodiments, fulvestrant is present in the suspension at a concentration of about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, or about 125 mg/mL. In other embodiments, fulvestrant is present in the suspension at a concentration of about 75 mg/mL to about 95 mg/mL, about 80 mg/mL to about 100 mg/mL, about 90 mg/mL to about 110 mg/ml, about 95 mg/mL to about 105 mg/mL, about 95 mg/mL to about 115 mg/mL, about 100 mg/mL to about 110 mg/mL, about 110 mg/mL to about 125 mg/mL, including all ranges and subranges there between.

Pharmaceutical Compositions Comprising Fulvestrant

Other embodiments of the disclosure include pharmaceutical compositions comprising fulvestrant. These pharmaceutical compositions may be prepared by combining fulvestrant, as described herein, with one or more additional excipients, preferably pharmaceutically acceptable excipients.

In certain embodiments, the pharmaceutical compositions may further comprise a stabilizer, or one or more stabilizers, or two or more stabilizers. In still further embodiments of the invention, the stabilizer is selected from the group consisting of surfactants, polymers, cross-linked polymers, buffering agents, electrolytes, and non-electrolytes. In yet further embodiments of the invention, the pharmaceutical composition comprises a combination of two or more stabilizers selected from the group consisting of surfactants, polymers, cross-linked polymers, buffering agents, electrolytes, and non-electrolytes.

In certain embodiments of the invention, the pharmaceutical compositions comprising fulvestrant comprise about 0.2 mg/mL to about 75 mg/mL of one or more stabilizers, and all ranges and subranges therebetween. In particular embodiments of the invention, the pharmaceutical composition comprises about 0.2 to 0.7 mg/mL, 0.5 to 1 mg/mL, 1 to 5 mg/mL, 2 to 8 mg/mL, 5 to 6 mg/mL, 5 to 10 mg/mL, 8 to 12 mg/mL, 10 to 15 mg/mL, 15 to 20 mg/mL, 20 to 30 mg/mL, 30 to 40 mg/mL, 40 to 50 mg/mL, 45 to 55 mg/mL, 50 to 60 mg/mL, or 60 to 75 mg/mL of one or more stabilizers, and all ranges and subranges there between. In further embodiments of the invention, the pharmaceutical composition comprises about 0.2 mg/mL, 0.5 mg/mL, 1 mg/mL, 2 mg/mL, 3 mg/mL, 4 mg/mL, 5 mg/mL, 5.5 mg/mL, 6 mg/mL, 7 mg/mL, 8 mg/mL, 9 mg/mL, 10 mg/mL, 12 mg/mL, 15 mg/mL, 17 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, or about 75 mg/mL of one or more stabilizers.

In yet further embodiments of the invention, the stabilizer is a surfactant. For example, the stabilizer can be, but is not limited to, polyethylene oxide (PEO), a PEO derivative, polysorbate 80, polysorbate 20, poloxamer 188 (including, but not limited to, PLURONIC® F-68 poloxamer sold by BASF Corp. (Wyandotte, MI, USA)), poloxamer 124 (including, but not limited to, PLURONIC® L44 poloxamer sold by BASF Corp. (Wyandotte, MI, USA)), poloxamer 407 (including, but not limited to, PLURONIC® F127 poloxamer sold by BASF Corp. (Wyandotte, MI, USA)), polyethoxylated vegetable oils, polyethoxylated castor oil (including but not limited to KOLLIPHOR® EL, formerly known as CREMOPHOR® EL sold by BASF Corp. (Wyandotte, MI, USA)), sorbitan palmitate (including, but not limited to, SPAN™ 40 sold by Croda International Plc), lecithin, poly(vinyl alcohol) ("PVA"), human serum albumin, and mixtures thereof.

In particular embodiments of the invention, the stabilizer is a polymer. For example, the stabilizer can be, but is not limited to, a polyvinylpyrrolidone ("PVP") (such as, but not limited to povidone K12, povidone K17, including as sold under the tradenames PLASDONE™ C-12 povidone, PLASDONE™ C-17 povidone, and PLASDONE™ C-30 povidone, and mixtures thereof), polyethylene glycol 3350, and mixtures thereof.

In other embodiments of the invention, the stabilizer is an electrolyte, i.e., a salt that dissociates into anions and cations in aqueous solution. For example, the stabilizer can be, but is not limited to, sodium chloride, calcium chloride, and mixtures thereof.

In still other embodiments of the invention, the stabilizer is a non-electrolyte, i.e., is non-ionic. For example, the stabilizer can be, but is not limited to, dextrose, glycerol (also referred to as glycerin), mannitol, or mixtures thereof.

In other embodiments of the invention, the stabilizer is a cross-linked polymer. For example, the stabilizer can be, but is not limited to, carboxymethylcellulose sodium (CMC). In some embodiments of the invention, the carboxymethylcellulose sodium stabilizer is CMC 7LF, CMC 7MF, CMC 7HF, or mixtures thereof.

In other embodiments of the invention, the stabilizer is a buffering agent, for example, $NaH_2PO_4 \cdot H_2O$, $NaH_2PO_4 \cdot 2H_2O$, anhydrous $NaH_2PO_4$, sodium citrate, citric acid, Tris, sodium hydroxide, HCl, or mixtures thereof.

In further embodiments of the invention, combinations of non-electrolyte stabilizers and electrolyte stabilizers may be used. In some embodiments, the combination of stabilizers may comprise two or more non-electrolyte stabilizers. In other embodiments, the combination of stabilizers may comprise two or more electrolyte stabilizers. In further embodiments, the combination of stabilizers may comprise one or more non-electrolyte stabilizers and one or more electrolyte stabilizers. In yet further embodiments, the combination of stabilizers may comprise two or more of mannitol, dextrose, and sodium chloride.

In certain embodiments of the invention, combinations of surfactant stabilizers and polymer stabilizers may be used. In some embodiments, the combination of stabilizers may comprise two or more surfactant stabilizers. In other embodiments, the combination of stabilizers may comprise two or more polymer stabilizers. In further embodiments, the combination of stabilizers may comprise one or more surfactant stabilizers and one or more polymer stabilizers. In yet further embodiments, the combination of stabilizers may comprise two or more of polysorbate 80, polysorbate 20, and poloxamer 188. In still further embodiments, the combination of stabilizers may comprise one or more of polysorbate 80, polysorbate 20, and poloxamer 188 and one or more of povidone K12, povidone K17, polyvinylpyrrolidone as sold under the tradenames PLASDONE™ C-12 povidone, PLASDONE™ C-17 povidone, or PLASDONE™ C-30 povidone, and polyethylene glycol 3350. Polyethylene glycol 3350 has an average molecular weight of about 3350 g/mol (Polyethylene Glycol 3350 monograph by The United States Pharmacopeial Convention, Dec. 1, 2020; Polyethylene Glycol 3350 by Atlantic Biologicals Corps, May 2018). In yet still further embodiments, the combination of stabilizers may comprise polysorbate 80 and one or more of polyvinylpyrrolidone as sold under the tradename PLASDONE™ C-12 povidone and povidone K12.

In certain embodiments, the pharmaceutical compositions comprising fulvestrant comprise CMC (carboxymethylcellulose sodium). In some embodiments, the CMC is prepared and heat sterilized before being combined with the fulvestrant during methods of preparation (described more fully elsewhere herein). In further embodiments of the invention, the viscosity of a CMC solution can be modulated by the degree of heating applied, which can allow for the formation of a plurality of fulvestrant pharmaceutical compositions having identical constituents, but with different viscosity values. These different viscosity values can affect the physical stability of the fulvestrant pharmaceutical compositions and the pharmacokinetic characteristics upon administration to subjects. In some embodiments, fulvestrant pharmaceutical compositions comprising CMC may be prepared in two or more parts with each part comprising a different amount of CMC. In other embodiments one or more such parts may be a suspension free of any CMC. In further embodiments, the parts can be mixed in an appropriate ratio to obtain a desired pharmaceutical composition.

In certain embodiments of the invention, the pharmaceutical compositions in the form of liquid suspensions comprising fulvestrant and one or more stabilizers may exhibit different sedimentation behaviors to form either flocculated or caked suspension upon storage. In some embodiments of the invention, after being stored, pharmaceutical compositions in the form of liquid suspensions comprising fulvestrant can be redispersed back into a homogeneous suspension with an acceptable particle size distribution upon redispersion. Exemplary liquid suspension formulations described herein were prepared and tested for sedimentation and redispersion. The tested formulations exhibited different sedimentation behaviors, but all were redispersible back to an acceptable, homogeneous suspension after a 3-month storage period at room temperature.

In certain embodiments of the invention, the pharmaceutical compositions comprising fulvestrant have a pH of from about 3-10, for example, about 3, 4, 5, 6, 7, 8, 9, or about 10. In further embodiments of the invention, the pharmaceutical composition has a pH of from about 5-8. In further embodiments of the invention, the pharmaceutical composition has a pH of from about 6-8. In further embodiments of the invention, the pharmaceutical composition has a pH of from about 3-7. In certain embodiments of the invention, the pharmaceutical composition has a pH of about 6.0 to 8.0. In particular embodiments of the invention, the pharmaceutical composition has a pH of about 6.0 to 7.0, 6.5 to 7.0, 6.5 to 7.5, 6.7 to 7.2, 7.0 to 7.2, 7.0 to 7.5, or 7.0 to 8.0. In further embodiments of the invention, the pharmaceutical composition has a pH of about 7.0.

In particular embodiments of the invention, the pharmaceutical composition further comprises one or more buffering agents, i.e., an agent that when added to a pharmaceutical composition, results in a pharmaceutical composition that resists pH changes or that results in a change in pH, such as, but not limited to, $NaH_2PO_4 \cdot H_2O$, $NaH_2PO_4 \cdot 2H_2O$, anhydrous $NaH_2PO_4$, sodium citrate, citric acid, Tris, sodium hydroxide, HCl, or mixtures thereof. In certain embodiments of the invention, the pharmaceutical composition comprises about 1 mM to 20 mM, of one or more buffering agents, and all ranges and subranges therebetween. In particular embodiments of the invention, the pharmaceutical composition comprises about 1 to 2 mM, 1 to 3 mM, 1 to 5 mM, 2 to 8 mM, 5 to 6 mM, 5 to 10 mM, 8 to 12 mM, 10 to 15 mM, or 15 to 20 mM of one or more buffering agents, and all ranges and subranges there between. In further embodiments of the invention, the pharmaceutical composition comprises about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM of one or more buffering agents.

In certain embodiments of the invention, the pharmaceutical composition has an osmolarity from about 280 mOsm/L to about 310 mOsm/L, for example, about 280, 285, 290, 300, 305, or about 310 mOsm/L. In further embodiments of the invention, the pharmaceutical composition has an osmolarity from about 290 mOsm/L to about 300 mOsm/L. In yet further embodiments of the invention, the pharmaceutical composition has an osmolarity of about 290 mOsm/L. In some embodiments, the osmolarity may be selected through the use of appropriate amounts of the one or more stabilizers, e.g., stabilizers that also act as tonicifiers, such as, but not limited to, the non-electrolyte stabilizers and electrolyte stabilizers described herein. In some embodiments, the osmolarity may be selected through the use of appropriate amounts of one or more buffering agents that act as tonicifiers in a pharmaceutical composition, such as, but not limited to, the buffering agents described herein.

In certain embodiments of the invention, the pharmaceutical composition has an absolute viscosity measured at 25° C. from about 1.0 cP to about 1000 cP, and all ranges and subranges therebetween. In particular embodiments of the invention, the pharmaceutical composition has an absolute viscosity measured at 25° C. from about 750 cP to about 1000 cP, about 500 to about 750 cP, about 250 cP to about 500 cP, about 100 cP to about 250 cP, about 50 cP to about 100 cP, about 25 cP to about 50 cP, about 10 cP to about 25 cP, about 1 cP to about 10 cP, about 1 cP to about 5 cP, about 1.0 cP to about 4.0 cP, about 1.0 cP to about 3.0 cP, about 1.0 cP to about 2.5 cP, about 1.0 cP to about 2.0 cP, about 1.5 cP to about 2.0 cP. In further embodiments of the invention, the pharmaceutical composition has an absolute viscosity measured at 25° C. of about 1.0 cP, 1.1 cP, 1.2 cP, 1.3 cP, 1.4 cP, 1.5 cP, 1.6 cP, 1.7 cP, 1.8 cP, 1.9 cP, 2.0 cP, 2.1 cP, 2.2 cP, 2.3 cP, 2.4 cP, 2.5 cP, 2.6 cP, 2.7 cP, 2.8 cP, 2.9 cP, 3.0 cP, 3.5 cP, 4.0 cP, 4.5 cP, 5.0 cP, 10 cP, 15 cP, or 20 cP.

In yet further embodiments of the invention, pharmaceutical compositions having a fulvestrant concentration of 50 mg/mL or 100 mg/mL have an absolute viscosity measured at 25° C. that is from about 2-fold to about 500-fold lower than FASLODEX™, and all ranges and subranges therebetween. In further embodiments of the invention, fulvestrant pharmaceutical compositions having a fulvestrant concentration of 50 mg/mL or 100 mg/mL have an absolute viscosity measured at 25° C. that is 500-fold lower, about 400-fold lower, about 300-fold lower, about 250-fold lower, about 200-fold lower, about 150-fold lower, about 100-fold lower, about 50-fold lower, about 40-fold lower, about 30-fold lower, about 20-fold lower, about 10-fold lower, about 5-fold lower, about 4-fold lower, about 3-fold lower, about 2-fold lower, or about 1.5-fold lower than FASLODEX™. In further embodiments of the invention, for example, fulvestrant pharmaceutical compositions having a fulvestrant concentration of 50 mg/mL or 100 mg/mL, have an absolute viscosity measured at 25° C. that is substantially equivalent to FASLODEX™. Table 21 provides density measurements of some exemplary fulvestrant pharmaceutical compositions of the present disclosure. Table 22 provides viscosity measurements of some exemplary fulvestrant pharmaceutical compositions of the present disclosure.

In certain embodiments of the invention, the pharmaceutical composition comprises one or more additional pharmaceutically acceptable excipients. As used herein, a pharmaceutically acceptable excipient is generally chemically and/or physically compatible with other ingredients in a pharmaceutical composition or pharmaceutical composition, and/or is generally physiologically compatible with the recipient thereof. In some embodiments, the one or more additional pharmaceutically acceptable excipients are selected from the group consisting of preservatives, antioxidants, or mixtures thereof. In yet further embodiments of the invention, the additional pharmaceutically acceptable excipient is a preservative such as, but not limited to, phenol, cresol, p-hydroxybenzoic ester, chlorobutanol, or mixtures thereof. In yet further embodiments of the invention, the additional pharmaceutically acceptable excipient is an antioxidant such as, but not limited to, ascorbic acid, sodium pyrosulfite, palmitic acid, butylated hydroxyanisole, butylated hydroxytoluene, tocopherols, or mixtures thereof.

In certain embodiments of the invention, the pharmaceutical composition comprises about 50 mg/mL fulvestrant, about 5.8 mg/mL of one or more stabilizers, and water for injection (WFI) q.s. to volume.

In further embodiments of the invention, the pharmaceutical composition comprises about 50 mg/mL fulvestrant, about 5 mg/mL of one or more surfactants, about 0.8 mg/mL of one or more polymers, and WFI q.s. to volume.

In yet further embodiments of the invention, the pharmaceutical composition comprises about 50 mg/mL fulvestrant, about 5 mg/mL of polysorbate 80, about 0.8 mg/mL of povidone K12 (PVP 12K), and WFI q.s. to volume.

In certain embodiments of the invention, the pharmaceutical composition comprises about 50 mg/mL fulvestrant, about 5.8 mg/mL of one or more stabilizers, about 9 mg/mL of one or more electrolytes, about 10 mM of one or more buffering agents, and WFI q.s. to volume.

In further embodiments of the invention, the pharmaceutical composition comprises about 50 mg/mL fulvestrant, about 5 mg/mL of one or more surfactants, about 0.8 mg/mL of one or more polymers, about 9 mg/mL of sodium chloride, about 10 mM of one or more of $NaH_2PO_4 \cdot H_2O$, $NaH_2PO_4 \cdot 2H_2O$, and anhydrous $NaH_2PO_4$ (preferably a mixture of about 0.61 mg/mL $NaH_2PO_4 \cdot 2H_2O$ and about 0.85 mg/mL of anhydrous $NaH_2PO_4$), and WFI q.s. to volume In certain embodiments of the invention, the pharmaceutical composition comprises about 50 mg/mL fulvestrant, about 55 mg/mL of one or more stabilizers, and WFI q.s. to volume.

In further embodiments of the invention, the pharmaceutical composition comprises about 50 mg/mL fulvestrant, about 5 mg/mL of one or more surfactants, about 50 mg/mL of one or more non-electrolytes, and WFI q.s. to volume.

In yet further embodiments of the invention, the pharmaceutical composition comprises about 50 mg/mL fulvestrant, about 5 mg/mL of polysorbate 80, about 50 mg/mL of dextrose, and WFI q.s. to volume.

In further embodiments of the invention, the pharmaceutical composition comprises about 50 mg/mL fulvestrant, about 5 mg/mL of polysorbate 80, about 50 mg/mL of mannitol, and WFI q.s. to volume.

In certain embodiments of the invention, the pharmaceutical composition comprises about 50 mg/mL fulvestrant, about 5 mg/mL of one or more stabilizers, about 9 mg/mL of one or more electrolytes, and WFI q.s. to volume.

In further embodiments of the invention, the pharmaceutical composition comprises about 50 mg/mL fulvestrant, about 5 mg/mL of one or more surfactants, about 9 mg/mL of sodium chloride, and WFI q.s. to volume.

In yet further embodiments of the invention, the pharmaceutical composition comprises about 50 mg/mL fulvestrant, about 5 mg/mL of polysorbate 80, about 9 mg/mL of sodium chloride, and WFI q.s. to volume.

In certain embodiments of the invention, the pharmaceutical composition comprises about 100 mg/mL fulvestrant, about 55 mg/mL of one or more stabilizers, and WFI q.s. to volume.

In further embodiments of the invention, the pharmaceutical composition comprises about 100 mg/mL fulvestrant, about 5 mg/mL of one or more surfactants, about 50 mg/mL of one or more non-electrolytes, and WFI q.s. to volume.

In yet further embodiments of the invention, the pharmaceutical composition comprises about 100 mg/mL fulvestrant, about 5 mg/mL of polysorbate 80, about 50 mg/mL of mannitol, and WFI q.s. to volume.

In certain embodiments of the invention, the pharmaceutical composition comprises about 100 mg/mL fulvestrant, about 56.6 mg/mL of one or more stabilizers, and WFI q.s. to volume.

In further embodiments of the invention, the pharmaceutical composition comprises about 100 mg/mL fulvestrant, about 5 mg/mL of one or more surfactants, about 1.6 mg/mL of one or more polymers, about 50 mg/mL of one or more non-electrolytes, and WFI q.s. to volume.

In yet further embodiments of the invention, the pharmaceutical composition comprises about 100 mg/mL fulvestrant, about 5 mg/mL of polysorbate 80, about 1.6 mg/mL of polyvinylpyrrolidone as sold under the tradename PLASDONE™ C-12 povidone, povidone K12, or a mixture thereof, about 50 mg/mL of mannitol, and WFI q.s. to volume.

In certain embodiments of the invention, the pharmaceutical composition comprises about 100 mg/mL fulvestrant, about 57.4 mg/mL of one or more stabilizers, and WFI q.s. to volume.

In further embodiments of the invention, the pharmaceutical composition comprises about 100 mg/mL fulvestrant, about 5 mg/mL of one or more surfactants, about 2.4 mg/mL of one or more polymers, about 50 mg/mL of one or more non-electrolytes, and WFI q.s. to volume.

In yet further embodiments of the invention, the pharmaceutical composition comprises about 100 mg/mL fulvestrant, about 5 mg/mL of polysorbate 80, about 2.4 mg/mL of polyvinylpyrrolidone as sold under the tradename PLASDONE™ C-12 povidone, povidone K12, or a mixture thereof, about 50 mg/mL of mannitol, and WFI q.s. to volume.

In certain embodiments of the invention, the pharmaceutical composition comprises about 100 mg/mL fulvestrant, about 5 mg/mL of polysorbate 80, between about 1 mg/mL and 2.4 mg/mL of PVP, sorbitan palmitate, poloxamer 188, poloxamer 124, poloxamer 427, polyethoxylated castor oil, PVA, or a mixture thereof, about 50 mg/mL of mannitol, and WFI q.s. to volume.

In further embodiments of the invention, the pharmaceutical composition comprises about 100 mg/mL fulvestrant, about 5 mg/mL of polysorbate 80, about 2.4 mg/mL of PVA, about 50 mg/mL of mannitol, and WFI q.s. to volume.

In yet further embodiments of the invention, the pharmaceutical composition comprises about 100 mg/mL fulvestrant, about 5 mg/mL of polysorbate 80, about 1.0 mg/mL of polyethoxylated castor oil, about 50 mg/mL of mannitol, and WFI q.s. to volume.

In certain embodiments of the invention, the pharmaceutical composition comprises about 100 mg/mL fulvestrant, about 5 mg/mL of polysorbate 80, about 2.0 mg/mL of poloxamer 188, about 50 mg/mL of mannitol, and WFI q.s. to volume.

In certain embodiments of the invention, the pharmaceutical composition comprises about 100 mg/mL fulvestrant, about 5 mg/mL of polysorbate 80, about 1.5 mg/mL of poloxamer 188, about 50 mg/mL of mannitol, and WFI q.s. to volume.

In certain embodiments of the invention, the pharmaceutical composition comprises about 100 mg/mL fulvestrant, about 5 mg/mL of polysorbate 80, about 1.5 mg/mL of sorbitan palmitate, about 50 mg/mL of mannitol, and WFI q.s. to volume.

In certain embodiments of the invention, the pharmaceutical composition comprises about 100 mg/mL fulvestrant, about 5 mg/mL of polysorbate 80, about 1.5 mg/mL of poloxamer 124, about 50 mg/mL of mannitol, and WFI q.s. to volume.

In certain embodiments of the invention, the pharmaceutical composition comprises about 100 mg/mL fulvestrant, about 5 mg/mL of polysorbate 80, about 1.5 mg/mL of poloxamer 407, about 50 mg/mL of mannitol, and WFI q.s. to volume.

Aspects of some exemplary embodiments of pharmaceutical compositions comprising fulvestrant are shown in Tables 1-20 and 23-27.

In the Figures and specification, references are made to exemplary formulations. Some exemplary formulations are identified as "F ###" where each "#" is a numeral, e.g., F001, F002, and so on. The exemplary formulations sharing an initial identification "F ###" share identical concentrations of constituent components (mg/mL), but may vary in their properties due to different methods of preparation, particle size distributions of fulvestrant, or other differences in processing, storage, or handling. Such exemplary formulation sharing an initial identification scheme "F ###" are further identified by extra alphanumeric characters. For example, the exemplary formulations F003a, F003b, and F003k2 have the same concentrations of constituent components but may differ in, e.g., the underlying methods of preparation and resulting particle size distributions. In some instances in the Figures, formulations are identified by only ending non-zero numerals # or ## and subsequent alphanumeric characters; for example, formulation F003a may be referred to as "Variant 3a", formulation F005a2 may be referred to as "Variant 5a2", and the like. Some exemplary formulations are identified and referred to as "Lot"s, with references to the same Lot number referring to exemplary formulations having the same concentrations of constituent components, but may vary in their properties due to different methods of preparation, particle size distributions of fulvestrant, or other differences in processing, storage, or handling.

TABLE 1

| Target Formulation (mg/mL) | Formulation B | | Formulation E | | Formulation I | |
|---|---|---|---|---|---|---|
| Fulvestrant | 50 | | 50 | | 50 | |
| Polysorbate 80 | 5 | | 5 | | 5 | |
| PVP 12K | 0.8 | | 0.8 | | 0.8 | |
| NaCl | | | | | 9 | |
| WFI | q.s. to volume | | q.s. to volume | | q.s. to volume | |
| Assay (% LC) | 100.0 | | 93.5 | | 94.0 | |
| Total Impurities (% a/a) | 0.2 | | 0.3 | | 0.2 | |
| PSD (via laser diffraction) | as is | sonicated | as is | sonicated | as is | sonicated |
| Day 0 LD Dv (10) (µm) | 7.4 | 6.0 | 2.4 | 1.9 | NA | NA |
| LD Dv (50) | 35.0 | 32.0 | 5.2 | 3.9 | | |
| LD Dv (90) (µm) | 143 | 129 | 11.1 | 8.7 | | |
| | day 5 | | day 1 | | day 4 | |
| LD Dv (10) | 7.6 | 2.3 | 2.3 | 1.2 | 2.5 | 0.04 |
| LD Dv (50) | 31.9 | 5.7 | 5.0 | 1.8 | 5.6 | 0.8 |
| LD Dv (90) (µm) | 107 | 19.2 | 10.9 | 2.5 | 12.3 | 3.2 |
| | day 14 | | Day 10 | | Day 11 | |
| LD Dv (10) | 5.9 | 5.1 | 1.9 | 1.8 | 2.3 | 0.06 |
| LD Dv (50) | 27.5 | 24.4 | 4.0 | 3.8 | 4.8 | 1.3 |
| LD Dv (90) (µm) | 86.3 | 76.0 | 9.1 | 9.4 | 9.4 | 3.7 |
| | Day 77 | | Day 71 | | Day 12 | |
| LD Dv (10) | 5.4 | 4.8 | 2.1 | 1.8 | 2.4 | 0.2 |
| LD Dv (50) | 26.3 | 21.0 | 4.7 | 3.8 | 5.1 | 3.0 |
| LD Dv (90) | 88.7 | 62.2 | 12.5 | 9.7 | 11.4 | 6.3 |
| pH | 7.4 (day 11) | | 6.9 (day 7) | | 7.1 (day 4) | |
| pH | N/A | | N/A | | 6.9 (day 11) | |

TABLE 2

| Target Formulation (mg/mL) | | Formulation J | | Formulation K | | Formulation L | |
|---|---|---|---|---|---|---|---|
| Fulvestrant | | 50 | | 50 | | 100 | |
| Polysorbate 80 | | 5 | | 5 | | 5 | |
| PVP 12K | | 0.8 | | 0.8 | | 0.8 | |
| NaCl | | 9 | | 9 | | 9 | |
| Phosphate buffer* | | 10 mM | | 10 mM | | 10 mM | |
| WFI | | q.s. to volume | | q.s. to volume | | q.s. to volume | |
| Assay (% LC) | | 80.9 | | 82.4 | | 94.1 | |
| Total Impurities (% a/a) | | 0.2 | | 0.2 | | 0.2 | |
| PSD (via laser diffraction) | | as is | sonicated | as is | sonicated | as is | sonicated |
| Day 0 (µm) | LD Dv (10) | 2.2 | 1.8 | 0.04 | 0.04 | 2.4 | 1.9 |
| | LD Dv (50) | 5.4 | 4.2 | 1.9 | 1.1 | 5.0 | 4.1 |
| | LD Dv (90) | 11.8 | 10.3 | 4.7 | 3.6 | 10.4 | 8.4 |
| (µm) | | day 5 | | day 4 | | Day 0 | |
| | LD Dv (10) | 2.0 | 1.7 | 0.03 | 0.04 | 2.4 | 1.9 |
| | LD Dv (50) | 4.7 | 3.8 | 1.4 | 1.1 | 5.0 | 4.1 |
| | LD Dv (90) | 9.7 | 8.2 | 3.6 | 3.0 | 10.4 | 8.4 |
| (µm) | | Day 12 | | Day 11 | | Day 11 | |
| | LD Dv (10) | 2.1 | 1.8 | 1.8 | 0.05 | 2.0 | 2.0 |
| | LD Dv (50) | 5.2 | 4.2 | 3.6 | 2.1 | 4.0 | 4.0 |
| | LD Dv (90) | 14.8 | 14.5 | 6.9 | 4.9 | 7.6 | 7.8 |
| (µm) | | Day 13 | | Day 12 | | Day 11 | |
| | LD Dv (10) | 2.3 | 1.9 | 2.2 | 0.06 | 2.5 | 2.2 |
| | LD Dv (50) | 5.9 | 4.6 | 4.5 | 2.3 | 5.3 | 5.0 |
| | LD Dv (90) | 16.5 | 16.0 | 11.1 | 5.6 | 10.8 | 10.6 |
| pH | | | | 7.0 (day 4) | | 7.0 (day 1) | |
| pH | | | | 7.0 (day 11) | | 7.1 (day 12) | |

TABLE 3

| Target Formulation (mg/mL) | | Formulation L3F | | Formulation L6 | |
|---|---|---|---|---|---|
| Fulvestrant | | 50 | | 100 | |
| Polysorbate 80 | | 5 | | 5 | |
| PVP 12K | | 0.8 | | 0.8 | |
| NaCl | | 9 | | 9 | |
| Phosphate buffer* | | 10 mM | | 10 mM | |
| WFI | | q.s. to volume | | q.s. to volume | |
| Assay (mg/mL) | | 83.8 | | 113.9 | |
| Total Impurities (% a/a) | | 0.7 | | 0.2 | |
| PSD (via laser diffraction) | | as is | sonicated | as is | sonicated |
| Day 0 (µm) | LD Dv(10) | 2.1 | 2.0 | 2.2 | 2.1 |
| | LD Dv(50) | 5.9 | 5.5 | 6.9 | 6.7 |
| | LD Dv(90) | 14.7 | 14.2 | 17.6 | 17.7 |
| | | Day 14 | | Day 1 | |
| (µm) | LD Dv(10) | 2.1 | 2.0 | 2.1 | 2.1 |
| | LD Dv(50) | 5.7 | 5.5 | 6.8 | 6.6 |
| | LD Dv(90) | 14.4 | 14.0 | 18.0 | 17.7 |
| pH | | | | 7.1 (day 1) | |

TABLE 4

| Target Formulation | | F003a | | F003b | | F004a | |
|---|---|---|---|---|---|---|---|
| Fulvestrant | | 100 | | 100 | | 100 | |
| Polysorbate 80 | | 5 | | 5 | | 5 | |
| Dextrose | | 50 | | 50 | | | |
| NaCl | | | | | | 9 | |
| WFI | | q.s. to volume | | q.s. to volume | | q.s. to volume | |
| Manufacturing Process | | API size reduction by HSM only | | API size reduction by HSM followed by HPH | | API size reduction by HSM followed by HPH | |
| Assay (mg/mL) | | 95.0 | | 96.3 | | 99.8 | |
| Total Impurities (%) | | 0.42 | | 0.28 | | 0.27 | |
| PSD (via laser diffraction) | | as is | sonicated | as is | sonicated | as is | sonicated |
| Day 0 | LD | 1.9 | 1.9 | 2.2 | 1.6 | 1.9 | 1.5 |
| (µm) | LD | 5.3 | 5.2 | 6.0 | 3.9 | 5.8 | 3.5 |
| | LD | 13.0 | 12.7 | 12.1 | 7.6 | 12.2 | 7.7 |
| (µm) | | Day 13 | | Day 13 | | Day 13 | |
| | LD Dv (10) | 1.9 | 1.9 | 2.1 | 1.7 | 1.7 | 1.5 |
| | LD Dv (50) | 5.3 | 5.2 | 5.5 | 4.2 | 4.0 | 3.3 |
| | LD Dv (90) | 13.4 | 13.0 | 11.3 | 8.2 | 8.7 | 6.8 |

TABLE 4-continued

| Target Formulation | F003a | | F003b | | F004a | |
|---|---|---|---|---|---|---|
| (μm) | Day 13 | | Day 13 | | Day 13 | |
| LD Dv (10) | 1.8 | 1.7 | 2.1 | 1.7 | 1.7 | 1.6 |
| LD Dv (50) | 5.1 | 4.9 | 5.9 | 4.3 | 4.0 | 3.4 |
| LD Dv (90) | 13.0 | 13.2 | 12.1 | 8.4 | 8.6 | 6.3 |
| pH | | | 7.3 (Day 0) | | 7.5 (Day 0) | |
| pH | | | 7.1 (Day 13) | | 7.1 (Day 13) | |

TABLE 5

| Target Formulation (mg/mL) | | F003e | | F003k2 | | F003k3 | |
|---|---|---|---|---|---|---|---|
| Fulvestrant | | 100 | | 100 | | 100 | |
| Polysorbate 80 | | 5 | | 5 | | 5 | |
| Dextrose | | 50 | | 50 | | 50 | |
| WFI | | q.s. to volume | | q.s. to volume | | q.s. to volume | |
| Manufacturing Process | | Micronized API dispersed by vortex/ sonics or HSM | | Micronized API dispersed by HSM | | Micronized API dispersed by HSM followed by HPH for size reduction | |
| Assay (mg/mL) | | 100.5 | | 97.8 | | 99.6 | |
| Total Impurities (% a/a) | | 0.34 | | 0.43 | | 0.42 | |
| PSD (via laser diffraction) | | as is | sonicated | as is | sonicated | as is | sonicated |
| Day 0 | LD Dv (10) | 1.5 | 1.5 | 1.5 | 1.4 | 2.2 | 1.4 |
| (μm) | LD Dv (50) | 3.9 | 3.8 | 2.9 | 2.6 | 7.0 | 3.4 |
| | LD Dv (90) | 13.0 | 12.8 | 6.7 | 6.3 | 13.3 | 7.4 |
| (μm) | | Day 1 | | Day 5 | | Day 1 | |
| | LD Dv (10) | 1.5 | 1.5 | NA | NA | NA | NA |
| | LD Dv (50) | 4.0 | 4.0 | | | | |
| | LD Dv (90) | 12.4 | 12.5 | | | | |
| (μm) | | Day 13 | | Day 12 | | Day 8 | |
| | LD Dv (10) | 1.5 | 1.5 | 1.6 | 1.5 | 1.5 | 1.3 |
| | LD Dv (50) | 4.1 | 4.1 | 3.2 | 2.9 | 2.9 | 2.6 |
| | LD Dv (90) | 14.0 | 14.3 | 7.0 | 6.5 | 5.7 | 5.2 |
| (μm) | | Day 22 | | Day 12 | | Day 8 | |
| | LD Dv (10) | 1.5 | 1.5 | 1.5 | 1.4 | 1.4 | 1.1 |
| | LD Dv (50) | 3.9 | 3.9 | 3.0 | 2.8 | 2.8 | 1.9 |
| | LD Dv (90) | 12.6 | 12.8 | 6.7 | 6.4 | 6.2 | 3.5 |
| pH | | | | 7.2 (day 1) | | 7.2 (day 0) | |
| pH | | | | 4.5 (Day 12) | | 6.8 (Day 8) | |

TABLE 6

| Target Formulation (mg/mL) | | F003i | | F005a2 | | F005b1 | |
|---|---|---|---|---|---|---|---|
| Fulvestrant | | 100 | | 100 | | 100 | |
| Polysorbate 80 | | 5 | | 5 | | 5 | |
| Dextrose | | 50 | | | | | |
| Mannitol | | | | 50 | | 50 | |
| WFI | | q.s. to volume | | q.s. to volume | | q.s. to volume | |
| Manufacturing Process | | Reconstituted lyophilized suspension, micronized API dispersed by HSM | | Reconstituted lyophilized suspension, API sized reduction by HSM | | Micronized API dispersed by HSM | |
| Assay (mg/mL) | | 99.2 | | 93.2 | | 100.2 | |
| Total Impurities (% a/a) | | 0.46 | | 0.55 | | 0.36 | |
| PSD (via laser diffraction) | | as is | sonicated | as is | sonicated | as is | sonicated |
| Day 0 (μm) | LD | 4.6 | 1.7 | 2.1 | 2.0 | 1.5 | 1.4 |
| | LD | 54.2 | 5.6 | 6.5 | 5.6 | 3.2 | 2.7 |
| | LD | 112 | 16.2 | 18.4 | 13.5 | 7.9 | 6.6 |

TABLE 6-continued

| Target Formulation (mg/mL) | | F003i | | F005a2 | | F005b1 |
|---|---|---|---|---|---|---|
| | | Day 9 | | Day 8 | | Day 13 |
| (µm) | LD | 2.5 | 1.5 | 2.1 | 2.0 | |
| | LD | 39.5 | 4.3 | 6.2 | 5.4 | |
| | LD | 95.1 | 13.5 | 16.7 | 13.2 | |
| | Day(90) | | | | | |
| pH | | | | 6.5 (Day3) | | 7.4 (Day 0) |
| pH | | | | 7.2 (Day 9) | | |

TABLE 7

| Target Formulation (mg/mL) | F005c2 | | F0017a | | F0015a | |
|---|---|---|---|---|---|---|
| Fulvestrant | 100 | | 100 | | 100 | |
| Polysorbate 80 | 5 | | 15 | | 25 | |
| Mannitol | 50 | | 50 | | 50 | |
| WFI | q.s. to volume | | q.s. to volume | | q.s. to volume | |
| Manufacturing Process | Micronized API dispersed by HSM followed by HPH for size reduction | | Micronized API dispersed by HSM | | Micronized API dispersed by HSM | |
| Assay (mg/mL) | 100.2 | | | | 103.8 | |
| Total Impurities (% a/a) | | | | | 0.39 | |
| PSD (via laser diffraction) | as is | sonicated | as is | sonicated | as is | sonicated |
| Day 0 | LD | 1.3 | 1.1 | 1.5 | 1.4 | 1.5 | 1.4 |
| (µm) | LD | 2.3 | 1.9 | 3.0 | 2.6 | 2.9 | 2.6 |
| | LD | 4.9 | 3.7 | 7.2 | 6.4 | 6.9 | 6.4 |
| pH | | | 7.1 (day 0) | | 7.1 (day 0) | |

TABLE 8

| | Formulation/Variants | | | | | | |
|---|---|---|---|---|---|---|---|
| mg/mL | I | J | K | L | M | N | O, O2 |
| Fulvestrant | 50 | 50 | 50 | 100 | 100 | 100 | 100 |
| Polysorbate 80 | 5 | 5 | 5 | 5 | 5 | 5 | 5 |
| Povidone K12 | 0.8 | 0.8 | 0.8 | 0.8 | 0.8 | 0.8 | 0.8 |
| Sodium Chloride | 9 | 9 | 9 | 9 | 9 | 4.5 | |
| Dextrose | | | | | | 25 | 50 |
| $NaH_2PO_4 \cdot 2H_2O$ | | 0.61 | 0.61 | 0.61 | | | |
| $Na_2HPO_4$ | | 0.85 | 0.85 | 0.85 | | | |
| WFI | QS | QS | QS | QS | QS | QS | QS |

TABLE 9

| | Formulation | | | | | | | |
|---|---|---|---|---|---|---|---|---|
| variants (mg/mL) | F001 F001e | F002 B, E | F003 F003a, b, e, f, g, h, i, j, k2, k3, l | F004 F004a | F005 F005a, a2, b1, c, c2, c3, d, d1, g, g4, g5, h3 | F015 F015a, a1, a3 | F016 | F017 F017a, a1, a3 |
| Fulvestrant | 100 | 100 | 100 | 100 | 100 | 100 | 100 | 100 |
| Polysorbate 80 | 5 | 5 | 5 | 5 | 5 | 25 | 5 | 15 |
| Povidone K12 | | 0.8 | | | | | 0.8 | |
| Sodium Chloride | | | | 9 | | | | |
| Dextrose | | 50 | | | | | | |
| Mannitol | | | | | | 50 | 50 | 50 | 50 |
| WFI | QS | QS | QS | QS | QS | QS | QS | QS |

TABLE 10

| (mg/mL) | Formulation | | | | | | | | | |
|---|---|---|---|---|---|---|---|---|---|---|
| | F003k+ | F006 | F007 | F008 | F009 | F010 | F011 | F012 | F013 | F014 |
| Fulvestrant | 200 | 100 | 100 | 100 | 100 | 100 | 100 | 100 | 100 | 100 |
| Polysorbate 80 | 5 | 25 | 5 | 5 | 5 | 5 | 5 | 5 | 5 | 5 |
| Dextrose | 50 | 50 | 50 | 50 | 50 | 50 | 50 | 50 | 50 | 50 |
| Polysorbate 20 | | | 15 | | | | | | | |
| Poloxamer 188 | | | | 2 | | | | | | |
| PVP K12 | | | | | 20 | | | | | |
| PVP K17 | | | | | | 5 | | | | |
| PEG 3350 | | | | | | | 60 | | | |
| CMC7LF PH | | | | | | | | 30 | | |
| CMC7MF PH | | | | | | | | | 20 | |
| CMC7HF PH | | | | | | | | | | 5 |
| WFI | QS | QS | QS | QS | QS | QS | QS | QS | QS | QS |

TABLE 11

| (mg/mL) | F018 | F019 | F020 | F021 | F022 | F023 | F024 | F025 | F026 | F027 | F028 |
|---|---|---|---|---|---|---|---|---|---|---|---|
| Fulvestrant | 100 | 100 | 100 | 100 | 100 | 100 | 100 | 100 | 100 | 100 | 100 |
| Polysorbate 80 | 5 | 5 | 5 | 5 | 5 | 5 | 5 | 5 | 5 | 5 | 5 |
| Polysorbate 20 | | | | | 5 | 15 | | 5 | 15 | 5 | |
| Poloxamer 188 | | | | | | | 2 | 2 | 2 | 2 | |
| Mannitol | 50 | 50 | 50 | 50 | 50 | 50 | 50 | 50 | 50 | 50 | 50 |
| Dextrose | | | | | | | | | | | |
| NaCl | | | | | | | | | | | |
| Glycerol | | | | | | | | | | | |
| PVP K12 | 5 | 10 | 20 | | | | | | | 10 | |
| PVP K17 | | | | 5 | | | | | | | |
| PEG 3350 | | | | | | | | | | | 60 |
| CMC7LF PH | | | | | | | | | | | |
| CMC7MF PH | | | | | | | | | | | |
| CMC7HF PH | | | | | | | | | | | |
| WFI | qs | qs | qs | qs | qs | qs | qs | qs | qs | qs | qs |

TABLE 12

| (mg/mL) | F029 | F030 | F031 | F032 | F033 | F034 | F035 | F036 |
|---|---|---|---|---|---|---|---|---|
| Fulvestrant | 100 | 100 | 100 | 100 | 100 | 100 | 100 | 100 |
| Polysorbate 80 | 5 | 5 | 5 | 5 | 5 | 5 | 5 | 5 |
| Polysorbate 20 | | | | | | | | 5 |
| Poloxamer 188 | | | | | | | | 2 |
| Mannitol | 50 | 25 | 12.5 | 37.5 | 50 | 50 | 50 | 50 |
| Dextrose | | 25 | 37.5 | 12.5 | | | | |
| NaCl | | | | | | | | |
| Glycerol | | 30 | | | | | | |
| PVP K12 | | | | | | | | 5 |
| PVP K17 | | | | | | | | |
| PEG 3350 | | | | | | | | |
| CMC7LF PH | | | | | 3 | 2 | 1 | 1 |
| CMC7MF PH | | | | | | | | |
| CMC7HF PH | | | | | | | | |
| WFI | qs | qs | qs | qs | qs | qs | qs | qs |

TABLE 13

| (mg/mL) | F037 | F038 | F039 | F040 | F041 | F042 | F043 | F044 | F045 | F046 | F047 |
|---|---|---|---|---|---|---|---|---|---|---|---|
| Fulvestrant | 100 | 100 | 100 | 100 | 100 | 100 | 100 | 100 | 100 | 100 | 100 |
| Polysorbate 80 | 5 | 5 | 5 | | 5 | 5 | 5 | | 5 | 5 | 5 |
| Polysorbate 20 | | | | 5 | | | | 5 | | | |
| Poloxamer 188 | | | | 2 | | | | 2 | | | |
| Mannitol | 25 | 25 | 25 | 25 | 12.5 | 12.5 | 12.5 | 12.5 | 37.5 | 37.5 | 37.5 |
| Dextrose | 25 | 25 | 25 | 25 | 37.5 | 37.5 | 37.5 | 37.5 | 12.5 | 12.5 | 12.5 |
| NaCl | | | | | | | | | | | |
| Glycerol | | | | | | | | | | | |
| PVP K12 | | | | 5 | | | | 5 | | | |
| PVP K17 | | | | | | | | | | | |
| PEG 3350 | | | | | | | | | | | |
| CMC7LF PH | 3 | 2 | 1 | 1 | 3 | 2 | 1 | 1 | 3 | 2 | 1 |
| CMC7MF PH | | | | | | | | | | | |
| CMC7HF PH | | | | | | | | | | | |
| WFI | qs | qs | qs | qs | qs | qs | qs | qs | qs | qs | qs |

TABLE 14

| (mg/mL) | F048 | F049 | F050 | F051 | F052 | F053 | F054 | F055 |
|---|---|---|---|---|---|---|---|---|
| Fulvestrant* | 100 | 100 | 100 | 100 | 100 | 100 | 100 | 100 |
| Polysorbate 80 | 5 | 5 | 5 | 5 | 5 | 5 | 5 | 5 |
| Polysorbate 20 | 5 | | | | | | | 5 |
| Poloxamer 188 | 2 | | | | | | | 2 |
| Mannitol | 37.5 | 25 | 25 | 25 | 25 | 25 | 25 | 25 |
| Dextrose | 12.5 | | | 25 | 25 | 25 | 25 | 25 |
| NaCl | | 4.9 | 9 | 4.9 | 4.9 | 4.9 | 4.9 | 4.9 |
| Glycerol | | | | | | | | |
| PVP K12 | 5 | | | | | | | 5 |
| PVP K17 | | | | | | | | |
| PEG 3350 | | | | | | | | |
| CMC7LF PH | 1 | | | | 3 | 2 | 1 | 1 |
| CMC7MF PH | | | | | | | | |
| CMC7HF PH | | | | | | | | |
| WFI | qs | qs | qs | qs | qs | qs | qs | qs |

TABLE 15

| (mg/mL) | F056 | F057 | F058 | F059 | F060 | F061 | F062 |
|---|---|---|---|---|---|---|---|
| Fulvestrant | 100 | 100 | 100 | 100 | 100 | 100 | 100 |
| Polysorbate 80 | | | | | | | |
| Polysorbate 20 | 5 | 10 | 15 | 5 | 5 | 10 | 10 |
| Poloxamer 188 | | | | | | | |
| Mannitol | 50 | 50 | 50 | 50 | 50 | 50 | 50 |
| Dextrose | | | | | | | |
| NaCl | | | | | | | |
| Glycerol | | | | | | | |
| PVP K12 | | | | | | | |
| PVP K17 | | | | | | | |
| PEG 3350 | | | | 10 | 30 | 10 | 30 |
| PEG 4000 | | | | | | | |
| CMC7LF PH | | | | | | | |
| CMC7MF PH | | | | | | | |
| CMC7HF PH | | | | | | | |
| WFI | qs | qs | qs | qs | qs | qs | qs |

TABLE 16

| (mg/mL) | F063 | F064 | F065 | F066 | F067 | F068 | F069 | F070 |
|---|---|---|---|---|---|---|---|---|
| Fulvestrant | 100 | 100 | 100 | 100 | 100 | 100 | 100 | 100 |
| Polysorbate 80 | | | | | | | | |
| Polysorbate 20 | 15 | 15 | 5 | 5 | 10 | 10 | 15 | 15 |
| Poloxamer 188 | | | | | | | | |
| Mannitol | 50 | 50 | 50 | 50 | 50 | 50 | 50 | 50 |
| Dextrose | | | | | | | | |
| NaCl | | | | | | | | |
| Glycerol | | | | | | | | |
| PVP K12 | | | | | | | | |
| PVP K17 | | | | | | | | |
| PEG 3350 | 10 | 30 | | | | | | |
| PEG 4000 | | | 3 | 7.5 | 3 | 7.5 | 3 | 7.5 |
| CMC7LF PH | | | | | | | | |
| CMC7MF PH | | | | | | | | |
| CMC7HF PH | | | | | | | | |
| WFI | qs | qs | qs | qs | qs | qs | qs | qs |

TABLE 17

| | Formulations/Variants | | | | | | | |
|---|---|---|---|---|---|---|---|---|
| Component | Q | R | S | T | U | V | W | X |
| Fulvestrant (mg/mL) | 100 | 100 | 100 | 100 | 100 | 100 | 100 | 100 |
| Polysorbate 80 (mg/mL) | 25 | 5 | — | — | 5 | 5 | — | 5 |
| Polysorbate 20 (mg/mL) | — | — | 5 | — | — | — | — | — |
| Poloxamer 188 (mg/mL) | — | — | — | 5 | — | — | — | — |
| Lecithin (mg/mL) | — | — | — | — | — | — | 5 | — |
| PVP K12 (mg/mL) | 0.8 | 5 | 0.8 | 0.8 | — | — | 0.8 | 0.8 |
| PVP K17 (mg/mL) | — | — | — | — | 0.8 | — | — | — |
| PEG 3350 (mg/mL) | — | — | — | — | — | 50 | — | — |
| Dextrose (mg/mL) | — | — | — | 50 | — | — | — | — |
| Sodium Chloride (mg/mL) | — | — | — | — | — | — | 9 | 13 |
| NaOH | QS to pH 7.0 | QS to pH 7.0 | QS to pH 7.0 | QS to pH 7.0 | QS to pH 7.0 | QS to pH 7.0 | QS to pH 7.0 | QS to pH 7.0 |
| HCl | QS to pH 7.0 | QS to pH 7.0 | QS to pH 7.0 | QS to pH 7.0 | QS to pH 7.0 | QS to pH 7.0 | QS to pH 7.0 | QS to pH 7.0 |
| WFI | QS to volume | QS to volume | QS to volume | QS to volume | QS to volume | QS to volume | QS to volume | QS to volume |

TABLE 18

| Component | Formulations/Variants | | | | | | | |
|---|---|---|---|---|---|---|---|---|
| | 1 | 2 | 3 | 4 | 5 | 6 | 7 | 8 |
| Fulvestrant (mg/mL) | 100 | 100 | 100 | 100 | 100 | 100 | 100 | 100 |
| Polysorbate 80 (mg/mL) | — | 5 | — | — | 5 | 5 | — | 5 |
| Polysorbate 20 (mg/mL) | — | — | 5 | — | — | — | — | — |
| Poloxamer 188 (mg/mL) | — | — | — | 5 | — | — | — | — |
| Human Serum Albumin (mg/mL) | 5 | | | | | | | |
| Lecithin (mg/mL) | — | — | — | — | — | — | 5 | — |
| PVP K12 (mg/mL) | 0.8 | 5 | 0.8 | 0.8 | — | — | 0.8 | 0.8 |
| PVP K17 (mg/mL) | — | — | — | — | 0.8 | — | — | — |
| PEG 3350 (mg/mL) | — | — | — | — | — | 50 | — | — |
| Dextrose (mg/mL) | | | 50 | | | | 50 | |
| Mannitol (mg/mL) | | | | — | | | — | 50 |
| Citric buffer | QS to pH 7.0 | QS to pH 7.0 | QS to pH 7.0 | QS to pH 7.0 | QS to pH 7.0 | QS to pH 7.0 | QS to pH 7.0 | QS to pH 7.0 |
| WFI | QS to volume | QS to volume | QS to volume | QS to volume | QS to volume | QS to volume | QS to volume | QS to volume |

TABLE 19

| Formulation (mg/mL) | F005g4 F005g5 | Lot 15 | Lot 26 | Lot 27 | Lot 28 | Lot 42 | Lot 43 | Lot X1 | Lot X2 |
|---|---|---|---|---|---|---|---|---|---|
| Fulvestrant | 100 | 100 | 100 | 100 | 100 | 100 | 100 | 100 | 100 |
| Polysorbate 80 | 5 | 5 | 5 | 5 | 5 | 5 | 5 | 5 | 5 |
| PVPC12 | — | | — | 1.6 | 1.6 | — | — | — | — |
| Span 40 | | | | | | 1.5 | — | | — |
| Pluronic F-68 | | | | | | | 1.5 | | |
| Pluronic L44 | | | | | | | | 1.5 | |
| Pluronic F127 | | | | | | | | | 1.5 |
| Mannitol (before homogenization) | 50 | 50 | — | 50 | — | 50 | 50 | 50 | 50 |
| Mannitol (after homogenization) | — | | 50 | — | 50 | | | | |

TABLE 20

| Formulation (mg/mL) | Lot 45 | Lot 46 | Lot 47 | Lot 48 |
|---|---|---|---|---|
| Fulvestrant | 100 | 100 | 100 | 100 |
| Polysorbate 80 | 5 | 5 | 5 | 5 |
| PVPC12 | 2.4 | — | | |
| Span 40 | — | — | | |
| Pluronic F-68 | | 2 | | |
| Cremophor EL | | | 1 | |
| PVA | | | | 2.4 |
| Mannitol (before homogenization) | 50 | 50 | 50 | 50 |

TABLE 21

| Sample Name | Density (g/ml) |
|---|---|
| F003h | 1.032 |
| F003f | 1.032 |
| F003e | 1.032 |
| F003k2 | 1.030 |

TABLE 22

| Sample Name | Formulation | Viscosity (cps) |
|---|---|---|
| Placebo | 5 mg/mL PS80 + 50 mg/mL Dextrose | 1.1 |
| F003h | [Described elsewhere] | 1.8 |
| F003f | [Described elsewhere] | 1.9 |
| F003k | [Described elsewhere] | 2.0 |
| F003e | [Described elsewhere] | 1.5 |

B. Fulvestrant Particles

Particular embodiments of the disclosure comprise solid fulvestrant particles, for example a fulvestrant suspension comprising solid fulvestrant particles. In certain embodiments of the invention, at least about 90% of the total fulvestrant in the formulation is present as solid particles. In further embodiments of the invention, at least about 80% of the total fulvestrant in the formulation is present as solid particles.

In certain embodiments of the invention, solid fulvestrant particles are particles consisting of crystalline and/or amorphous fulvestrant. In other embodiments of the invention, fulvestrant particles comprise crystalline and/or amorphous fulvestrant as well as other excipients. In still other embodiments, fulvestrant particles comprise crystalline and/or amorphous fulvestrant coated or surface modified by a surface modifier adsorbed on the surface of the particle. The surface modifier can be a stabilizer such as, but not limited to surfactants, polymers, electrolytes, and non-electrolytes, and mixtures thereof.

Other embodiments of the present invention may further comprise fulvestrant in forms other than a solid particle, such as, but not limited to, solubilized fulvestrant as a free molecule or associated with a suspension such as micelles, microemulsions, emulsion, liposome, and combinations thereof, or complexed with other formulation constituents in a vehicle. In further embodiments of the invention, such other forms of fulvestrant are in equilibrium with the fulvestrant solid particles.

In particular embodiments of the invention, the fulvestrant particles comprise about 90-99.9% by weight of fulvestrant and 0.1-10% by weight of a surface modifier adsorbed on the surface of said particle. In particular embodiments of the invention, the surface modifier is a stabilizer such as, but not limited to surfactants, polymers, electrolytes, and non-electrolytes, and mixtures thereof. In certain embodiments of the invention, fulvestrant particles comprise at least about 90% fulvestrant. In other embodiments of the invention fulvestrant particles comprise at least about 92%, 95%, 97%, 98%, 99%, 99.5%, or 99.9% fulvestrant.

In further embodiments of the invention, one or more solvents, such as water, present in the pharmaceutical composition can be removed partially or completely by appropriate techniques known to the art, such as lyophilization or spray drying, to form a dried pharmaceutical composition for reconstitution. In certain embodiments of the invention, the dried pharmaceutical composition can comprise up to about 1%, about 2%, about 5%, or about 10% of the one or more solvents. The dried pharmaceutical composition can be reconstituted with appropriate diluent known to the art, such as, but not limited to water for injection (WFI), normal saline (NS), and 5% dextrose in water (D5W) prior to administration. In further embodiments of the invention, the diluent can further comprise an organic solvent or one or more of the excipients described herein. Dried pharmaceutical compositions formed by lyophilization may be in the form of a lyophilized cake.

Fulvestrant Particle Sizes

In certain embodiments of the invention, the fulvestrant particles have a laser diffraction diameter greater than or equal to about 1 micron. In yet further embodiments of the invention, at least a portion of the fulvestrant particles have a laser diffraction diameter less than about 1 micron. In other embodiments of the invention the fulvestrant particles have a laser diffraction diameter greater than or equal to about 2 microns. In still other embodiments of the invention, at least a portion of the fulvestrant particles have a laser diffraction diameter less than about 2 microns.

In certain embodiments of the invention, the fulvestrant particles have a laser diffraction diameter greater than or equal to about 0.5 microns. In other embodiments of the invention, at least a portion of the fulvestrant particles have a laser diffraction diameter less than about 0.5 microns. In other embodiments of the invention, the fulvestrant particles have a laser diffraction diameter greater than or equal to about 1 micron. In other embodiments of the invention, at least a portion of the fulvestrant particles have a laser diffraction diameter less than about 1 microns. In still other embodiments of the invention, the fulvestrant particles have a laser diffraction diameter greater than or equal to about 1.5 microns. In other embodiments of the invention, at least a portion of the fulvestrant particles have a laser diffraction diameter less than about 1.5 microns. In yet other embodiments of the invention, the fulvestrant particles have a laser diffraction diameter greater than or equal to about 2 microns. In other embodiments of the invention, at least a portion of the fulvestrant particles have a laser diffraction diameter less than about 2 microns.

In further embodiments of the invention, about 98% of fulvestrant particles have a laser diffraction diameter greater than or equal to about 0.5 microns. In other embodiments of the invention, about 98% of fulvestrant particles have a laser diffraction diameter greater than or equal to about 1 micron. In still other embodiments of the invention, about 98% of fulvestrant particles have a laser diffraction diameter greater than or equal to about 1.5 microns. In yet other embodiments of the invention, about 98% of fulvestrant particles have a laser diffraction diameter greater than or equal to about 2 microns.

In certain embodiments of the invention, the fulvestrant particles have an LD Dv(90) between about 4 microns and about 120 microns, between about 4 microns and about 100 microns, between about 4 microns and about 75 microns, between about 4 microns and about 60 microns, between about 4 microns and about 50 microns, between about 4 microns and about 40 microns, between about 4 microns and about 30 microns, between about 4 microns and about 20 microns, between about 4 microns and about 15 microns, between about 4 microns and about 10 microns, between about 20 microns and about 60 microns, between about 20 microns and about 45 microns, between about 20 microns and about 30 microns, between about 30 microns and about 50 microns, or between about 4 microns and about 9 microns. In other embodiments of the invention, the fulvestrant particles have a LD Dv(90) equal to about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 25 microns, about 30 microns, about 35 microns, about 40 microns, about 45 microns, about 50 microns, about 55 microns, about 60 microns, about 65 microns, about 70 microns, about 75 microns, about 80 microns, about 85 microns, about 90 microns, about 95 microns, about 100 microns, about 105 microns, about 110 microns, about 115 microns, or about 120 microns.

In certain embodiments of the invention, the fulvestrant particles have an LD Dv(90) less than or equal to about 120 microns. In certain embodiments of the invention, the fulvestrant particles have an LD Dv(90) less than or equal to about 100 microns. In certain embodiments of the invention, the fulvestrant particles have an LD Dv(90) less than or equal to about 80 microns. In certain embodiments of the invention, the fulvestrant particles have an LD Dv(90) less than or equal to about 60 microns. In certain embodiments of the invention, the fulvestrant particles have an LD Dv(90) less than or equal to about 50 microns. In certain embodiments of the invention, the fulvestrant particles have an LD Dv(90) less than or equal to about 40 microns. In certain embodiments of the invention, the fulvestrant particles have an LD Dv(90) less than or equal to about 30 microns. In further embodiments of the invention, the particles have an LD Dv(90) less than or equal to about 25 microns. In further embodiments of the invention, the particles have an LD Dv(90) less than or equal to about 18 microns. In further embodiments of the invention, the particles have an LD Dv(90) less than or equal to about 16 microns. In further embodiments of the invention, the particles have an LD Dv(90) less than or equal to about 14 microns. In still further embodiments of the invention, the particles have an LD Dv(90) less than or equal to about 11 microns. In yet further embodiments of the invention, the particles have an LD Dv(90) less than or equal to about 9 microns. In yet further embodiments of the invention, the particles have an LD Dv(90) less than or equal to about 7 microns. In yet further embodiments of the invention, the particles have an LD Dv(90) less than or equal to about 5 microns. In particular embodiments of the invention, particles have an LD Dv(90) between about 9-14 microns. In other embodiments of the invention, the particles have an LD Dv(90) between about 12-14 microns. In yet other embodiments of the invention, the particles have an LD Dv(90) between about 9-11 microns. In yet other embodiments of the invention, the particles have an LD Dv(90) between about 7-9 microns. In yet other embodiments of the invention, the particles have an LD Dv(90) between about 6-8 microns. In yet other embodiments of the invention, the particles have an LD Dv(90) between about 6-7 microns. In yet other embodiments of the invention, the particles have an LD Dv(90) between about 3-6 microns.

In certain embodiments of the invention, the fulvestrant particles have an LD Dv(50) between about 2 microns and about 35 microns, between about 2 microns and about 25 microns, between about 2 microns and about 20 microns, between about 2 microns and about 15 microns, between about 2 microns and about 10 microns, between about 2 microns and about 8 microns, between about 2 microns and about 7 microns, between about 2 microns and about 6 microns, between about 2 microns and about 5 microns, between about 2 microns and about 4 microns, between about 5 microns and about 10 microns, between about 5 microns and about 15 microns, between about 7 microns and about 10 microns, between about 8 microns and about 10 microns, or between about 9 microns and about 16 microns. In other embodiments of the invention, the fulvestrant particles have a LD Dv(50) equal to about 2 microns, 3 microns, 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 25 microns, about 30 microns, or about 35 microns.

In certain embodiments of the invention, the fulvestrant particles have an LD Dv(50) less than or equal to about 9 microns. In other embodiments of the invention, the particles have an LD Dv(50) less than or equal to about 7 microns. In other embodiments of the invention, the particles have an LD Dv(50) less than or equal to about 6 microns. In yet other embodiments of the invention, the particles have an LD Dv(50) less than or equal to about 5 microns. In particular embodiments of the invention, the particles have an LD Dv(50) less than or equal to about 4 microns. In further embodiments of the invention, the particles have an LD Dv(50) less than or equal to about 3 microns. In further embodiments of the invention, the particles have an LD Dv(50) between about 4-6 microns. In further embodiments of the invention, the particles have an LD Dv(50) between about 3-5 microns. In yet further embodiments of the invention, the particles have an LD Dv(50) between about 3-4 microns. In yet further embodiments of the invention, the particles have an LD Dv(50) between about 2-3 microns.

In certain embodiments of the invention, the fulvestrant particles have an LD Dv(10) no more than about 3 microns, about 2 microns, or about 1 microns. In further embodiments of the invention, the particles have an LD Dv(10) between about 1 micron and about 3 microns. In still further embodiments of the invention, the particles have an LD Dv(10) greater than or equal to about 2 microns. In yet further embodiments of the invention, the particles have an LD Dv(10) between about 1.5 microns to about 2.5 microns. In yet further embodiments of the invention, the particles have an LD Dv(10) between about 1 micron to about 2 microns. In yet further embodiments of the invention, the particles have an LD Dv(10) between about 1.0 micron to about 1.5 microns. In even further embodiments of the invention, the particles have an LD Dv(10) of about 2 microns. In even further embodiments of the invention, the particles have an LD Dv(10) of about 1.5 microns.

In certain embodiments of the invention, the fulvestrant particles have an LD Dv(90) less than or equal to about 25 microns and an LD Dv(50) less than or equal to about 9 microns. In particular embodiments of the invention, the particles have an LD Dv(90) less than or equal to about 16 microns and an LD Dv(50) less than or equal to about 6 microns. In other embodiments of the invention, the particles have an LD Dv(90) less than or equal to about 11 microns and an LD Dv(50) less than or equal to about 5 microns. In yet other embodiments of the invention, the particles have an LD Dv(90) less than or equal to about 9 microns and an LD Dv(50) less than or equal to about 4 microns. In yet other embodiments of the invention, the particles have an LD Dv(90) less than or equal to about 8 microns and an LD Dv(50) less than or equal to about 4 microns.

In certain embodiments of the invention, the fulvestrant particles have an LD Dv(90) between about 9-14 microns and an LD Dv(50) between about 4-6 microns. In still other embodiments of the invention, the particles have an LD Dv(90) between about 9-11 microns and an LD Dv(50) between about 4-6 microns. In particular embodiments of the invention, the particles have an LD Dv(90) between about 12-14 microns and an LD Dv(50) between about 4-6 microns. In further embodiments of the invention, the particles have an LD Dv(90) between about 6-8 microns and an LD Dv(50) between about 2-4 microns. In further embodiments of the invention the fulvestrant particles have a laser diffraction diameter greater than or equal to about 1 micron. In yet further embodiments of the invention, at least a portion of the fulvestrant particles have a laser diffraction diameter less than about 1 micron. In other embodiments of the invention the fulvestrant particles have a laser diffraction diameter greater than or equal to about 2 microns. In still other embodiments of the invention, at least a portion of the fulvestrant particles have a laser diffraction diameter less than about 2 microns.

In certain embodiments of the invention, the fulvestrant particles have an LD Dv(90) between about 9-14 microns, an LD Dv(50) between about 4-6 microns, and an LD Dv(10) between about 2-3 microns. In other embodiments of the invention, the particles have an LD Dv(90) between about 9-11 microns, an LD Dv(50) between about 4-6 microns, and an LD Dv(10) between about 2-3 microns. In yet other embodiments of the invention, the particles have an LD Dv(90) between about 12-14 microns, an LD Dv(50) between about 4-6 microns, and an LD Dv(10) between about 2-3 microns. In yet other embodiments of the invention, the particles have an LD Dv(90) between about 6-9 microns, an LD Dv(50) between about 2-4 microns, and an LD Dv(10) between about 1-2 microns. In further embodiments of the invention the fulvestrant particles have a laser diffraction diameter greater than or equal to about 1 micron. In yet further embodiments of the invention, at least a portion of the fulvestrant particles have a laser diffraction diameter less than about 1 micron. In other embodiments of the invention the fulvestrant particles have a laser diffraction diameter greater than or equal to about 2 microns. In still other embodiments of the invention, at least a portion of the fulvestrant particles have a laser diffraction diameter less than about 2 microns.

In certain embodiments of the invention, the fulvestrant particles have an LD Dv(90) between about 9-14 microns, an LD Dv(50) between about 4-6 microns, and an LD Dv(10) between about 2-3 microns, and the fulvestrant particles have a laser diffraction diameter greater than or equal to about 1 micron. In other embodiments of the invention, the particles have an LD Dv(90) between about 9-14 microns, an LD Dv(50) between about 4-6 microns, and an LD Dv(10) between about 2-3 microns, and at least a portion of the fulvestrant particles have a laser diffraction diameter less than about 1 micron. In yet other embodiments of the invention, the fulvestrant particles have an LD Dv(90) between about 30 microns and about 110 microns, an LD Dv(50) between about 5 microns and about 30 microns, and an LD Dv(10) between about 1.5 microns and about 3 microns. In other embodiments of the invention, the particles have an LD Dv(90) between about 9-14 microns, an LD Dv(50) between about 4-6 microns, and an LD Dv(10) between about 2-3 microns, and the fulvestrant particles have a laser diffraction diameter greater than or equal to about 2 microns. In still other embodiments of the invention, the particles have an LD Dv(90) between about 9-14 microns, an LD Dv(50) between about 4-6 microns, and an LD Dv(10) between about 2-3 microns, and at least a portion of the fulvestrant particles have a laser diffraction diameter less than about 2 microns. In yet other embodiments of the invention, the particles have an LD Dv(90) between about 6-9 microns, an LD Dv(50) between about 2-4 microns, an LD Dv(10) between about 1-2 microns, and the fulvestrant particles have a laser diffraction diameter greater than or equal to about 0.5 microns. In yet other embodiments of the invention, the particles have an LD Dv(90) between about 6-9 microns, an LD Dv(50) between about 2-4 microns, an LD Dv(10) between about 1-2 microns, and at least a portion of the fulvestrant particles have a laser diffraction diameter less than about 0.5 microns. In further embodiments of the invention the fulvestrant particles have a laser diffraction diameter greater than or equal to about 1 micron. In yet further embodiments of the invention, at least a portion of the fulvestrant particles have a laser diffraction diameter less than about 1 micron. In other embodiments of the invention the fulvestrant particles have a laser diffraction diameter greater than or equal to about 2 microns. In still other embodiments of the invention, at least a portion of the fulvestrant particles have a laser diffraction diameter less than about 2 microns.

In certain embodiments of the invention, the fulvestrant particles have a CE Dv(10) between about 1 microns and about 25 microns, between about 2 microns and about 25 microns, between about 3 microns and about 7 microns, between about 4 microns and about 15 microns, between about 4 microns and about 10 microns, between about 4 microns and about 8 microns, between about 6 microns and about 8 microns, between about 6 microns and about 7 microns, or between about 1 microns and about 10 microns. In other embodiments of the invention, the fulvestrant particles have a CE Dv(10) equal to about 1 micron, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, or about 25 microns.

In certain embodiments of the invention, the fulvestrant particles have a CE Dv(50) between about 5 microns and about 60 microns, between about 5 microns and about 50 microns, between about 9 microns and about 20 microns, between about 9 microns and about 15 microns, between about 10 microns and about 50 microns, between about 10 microns and about 40 microns, between about 10 microns and about 30 microns, between about 10 microns and about 20 microns, between about 15 microns and about 30 microns, between about 15 microns and about 25 microns, between about 15 microns and about 20 microns, or between about 10 microns and about 15 microns. In other embodiments of the invention, the fulvestrant particles have a CE Dv(50) equal to about 5 micron, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, about 25 microns, about 30 microns, about 35 microns, about 40 microns, about 45 microns, about 50 microns, about 55 microns, or about 60 microns.

In certain embodiments of the invention, the fulvestrant particles have a CE Dv(90) between about 10 microns and about 200 microns, between about 25 microns and about 150 microns, between about 25 microns and about 125 microns, between about 25 microns and about 100 microns, between about 25 microns and about 75 microns, between about 25 microns and about 50 microns, between about 25 microns and about 40 microns, between about 25 microns and about 35 microns, between about 35 microns and about 90 microns, between about 35 microns and about 75 microns, between about 35 microns and about 50 microns, between about 35 microns and about 45 microns, between about 50 microns and about 100 microns, between about 50 microns and about 75 microns, or between about 20 microns and about 40 microns. In other embodiments of the invention, the fulvestrant particles have a CE Dv(90) equal to about 10 microns, about 15 microns, about 20 microns, about 25 microns, about 30 microns, about 35 microns, about 40 microns, about 45 microns, about 50 microns, about 55 microns, about 60 microns, about 65 microns, about 70 microns, about 75 microns, about 80 microns, about 85 microns, about 90 microns, about 95 microns, about 100 microns, about 105 microns, about 110 microns, about 115 microns, about 120 microns, about 125 microns, about 130 microns, about 135 microns, about 140 microns, about 145 microns, about 150 microns, about 155 microns, about 160 microns, about 165 microns, about 170 microns, about 175 microns, or about 200 microns.

In certain embodiments of the invention, the fulvestrant particles have a CE Dv(90) between about 35 microns and about 90 microns, a CE Dv(50) between about 10 microns and about 35 microns, and a CE Dv(10) between about 4 microns and about 10 microns. In other embodiments of the invention, the particles have a CE Dv(90) between about 25 microns and about 60 microns, a CE Dv(50) between about 10 microns and about 25 microns, and a CE Dv(10) between about 4 microns and about 8 microns. In other embodiments of the invention, the particles have a CE Dv(90) between about 20 microns and about 35 microns, a CE Dv(50) between about 10 microns and about 20 microns, and a CE Dv(10) between about 4 microns and about 8 microns. In still other embodiments of the invention, the particles have a CE Dv(90) between about 30 microns and about 100 microns, a CE Dv(50) between about 10 microns and about 50 microns, and a CE Dv(10) between about 4 microns and about 10 microns. In yet other embodiments of the invention, the particles have a CE Dv(90) between about 50 microns and about 100 microns, a CE Dv(50) between about 20 microns and about 50 microns, a CE Dv(10) between about 6 microns and about 8 microns. In yet other embodiments of the invention, the particles have a CE Dv(90) between about 50 microns and about 75 microns, a CE Dv(50) between about 30 microns and about 40 microns, a CE Dv(10) between about 8 microns and about 10 microns. In yet other embodiments of the invention, the particles have a CE Dv(90) between about 20 microns and about 60 microns, a CE Dv(50) between about 9 microns and about 20 microns, and a CE Dv(10) between about 3 microns and about 7 microns. In still further embodiments of the invention, the particles have a CE Dv(90) between about 20 microns and about 50 microns, a CE Dv(50) between about 9 microns and about 20 microns, and a CE Dv(10) between about 3 microns and about 7 microns. In other embodiments of the invention, the particles have a CE Dv(90) between about 20 microns and about 45 microns, a CE Dv(50) between about 9 microns and about 20 microns, and a CE Dv(10) between about 3 microns and about 7 microns. In yet further embodiments of the invention, the particles have a CE Dv(90) between about 20 microns and about 40 microns, a CE Dv(50) between about 9 microns and about 15 microns, and a CE Dv(10) between about 3 microns and about 7 microns. In further embodiments of the invention, the particles have a CE Dv(90) between about 20 microns and about 35 microns, a CE Dv(50) between about 9 microns and about 15 microns, and a CE Dv(10) between about 3 microns and about 7 microns. In still other embodiments of the invention, the particles have a CE Dv(90) between about 20 microns and about 45 microns, a CE Dv(50) between about 9 microns and about 15 microns, and a CE Dv(10) between about 3 microns and about 7 microns.

In certain embodiments of the invention, the fulvestrant particles have a CE Dn(90) between about 4 microns and about 20 microns, between about 6 microns and about 15 microns, between about 6 microns and about 12 microns, between about 8 microns and about 12 microns, between about 8 microns and about 11 microns, between about 4 microns and about 10 microns, between about 4 microns and about 8 microns, between about 4 microns and about 7 microns, or between about 4 microns and about 6 microns. In other embodiments of the invention, the fulvestrant particles have a CE Dn(90) equal to about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, or about 20 microns.

In certain embodiments of the invention, the fulvestrant particles have a CE Dn(50) between about 2.0 microns and about 10.0 microns, between about 2.0 microns and about 8.0 microns, between about 2.0 microns and about 6.0 microns, between about 2.0 microns and about 5.0 microns, between about 3.0 microns and about 5.0 microns, between about 3.5 microns and about 4.5 microns, between about 2.0 microns and about 4.0 microns, between about 2.5 microns and about 4.5 microns, or between about 2.5 microns and about 3.5 microns. In other embodiments of the invention, the fulvestrant particles have a CE Dn(50) equal to about 2.0 microns, about 2.5 microns, about 3.0 microns, about 3.5 microns, about 4.0 microns, about 4.5 microns, about 5.0 microns, about 5.5 microns, about 6.0 microns, about 6.5 microns, about 7.0 microns, about 7.5 microns, about 8.0 microns, about 8.5 microns, about 9.0 microns, about 9.5 microns, or about 10.0 microns.

In certain embodiments of the invention, the fulvestrant particles have a CE Dn(10) between about 0.5 microns and about 2.0 microns, between about 0.5 microns and about 1.5 microns, between about 1.0 microns and about 1.5 microns, between about 0.8 microns and about 1.2 microns, between about 0.9 microns and about 1.1 microns, or between about 0.5 microns and about 1.0 microns. In other embodiments of the invention, the fulvestrant particles have a CE Dn(10) equal to about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 microns.

In certain embodiments of the invention, the fulvestrant particles have a CE Dn(90) between about 4 microns and about 20 microns, a CE Dn(50) between about 2.0 microns and about 10.0 microns, and a CE Dn(10) between about 0.5 microns and about 2.0 microns. In other embodiments of the invention, the fulvestrant particles have a CE Dn(90) between about 6 microns and about 12 microns, a CE Dn(50) between about 2.0 microns and about 6.0 microns, and a CE Dn(10) between about 0.5 microns and about 1.5 microns. In further embodiments of the invention, the fulvestrant particles have a CE Dn(90) between about 8 microns and about 1 microns, a CE Dn(50) between about 3.0 microns and about 5.0 microns, and a CE Dn(10) between about 0.8 microns and about 1.2 microns.

C. Preparation Methods

In certain embodiments of the invention, formulations of the invention can be prepared from commercially available fulvestrant having different particle size distributions, such as, for example, recrystallized, micronized fulvestrant, or a combination thereof. In further embodiments of the invention, the formulations are prepared with sterilized, commercially available fulvestrant. In particular embodiments, commercially available fulvestrant is used in the formulations of the present invention without further processing for size reduction.

In other embodiments of the invention, fulvestrant particles suitable for use in formulations of the invention can be prepared from commercially available fulvestrant by any suitable methods known in the art. Suitable methods include, but are not limited to, size-reduction techniques such as milling, grinding, crushing, compression, attrition, low shear mixing, high shear mixing, high pressure homogenization, lyophilization, precipitation, or combinations thereof.

Desired particle size distributions for fulvestrant particles can be achieved by processing steps at one or more stages of formulation preparation. In some embodiments, the desired particle size distribution can be formed by processing fulvestrant material prior to suspension in media, by techniques described more fully elsewhere herein. In other embodiments, the desired particle size distribution can be formed by processing after suspension in media, by techniques described more fully elsewhere herein, including but not limited to high shear mixing and high pressure homogenization. In still other embodiments, the desired particle size distribution can be formed by a combination of the processing prior to and after suspension in media.

Suitable milling techniques include, but are not limited to, dry milling, wet milling, and cryogenic milling. Suitable milling machines include ball mills, pebble mills, rod mills, roller mills, colloid mills, impact mills, and jet mills. In certain embodiments of the invention, the particles can be reduced in size in the presence of one or more excipients or stabilizers, such as but not limited to a surfactants, polymers, electrolytes, and non-electrolytes, and mixtures thereof. Alternatively, the particles can be contacted with one or more excipients or stabilizers after they are reduced in size.

In certain embodiments of the invention, the formulations can be prepared from an un-milled commercially available fulvestrant by reducing the fulvestrant particle size with high shear mixing. In yet further embodiments of the invention, the formulations can be prepared from an un-milled, commercially available fulvestrant by reducing the fulvestrant particle size with high shear mixing followed by high pressure homogenization.

In certain embodiments of the invention, the formulations can be prepared from commercially available micronized fulvestrant by reducing the micronized fulvestrant particle size with high shear mixing ("HSM"). In yet further embodiments of the invention, the formulations can be prepared from an un-milled commercially available fulvestrant by reducing the fulvestrant particle size with high shear mixing followed by high pressure homogenization ("HPH").

In some embodiments of the invention, the formulations can be prepared using high pressure homogenization. In further embodiments of the invention, the high pressure homogenization process reduces particle size by subjecting the particle population to one or more of cavitation, shear, and impact within a homogenization chamber under operating pressures from about 5,000 psi to about 45,000 psi, for example, about 5,000, 10,000, 15,000, 20,000, 25,000, 30,000, 35,000, 40,000 or about 45,000 psi. In yet further embodiments of the invention, the high pressure homogenization process is performed at about 40,000 psi. In some embodiments of the invention, the high pressure homogenization process is performed at operating pressures from about 15,000 psi to about 20,000 psi. In further embodiments, the formulations can be prepared by passing the formulation suspension through a homogenization chamber under operating pressures for one or more passes, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 passes.

In the Figures and specification, references are made to exemplary formulations and processes for preparing exemplary formulations. Some exemplary preparation processes are identified with alphanumeric reference identifiers, such as "Process A1," "Process A2," and so on. Some exemplary formulations can share identical concentrations of constituent components (mg/mL), but may vary in their properties due to the different preparation processes, storage, or handling, which can result in different particle size distributions due to more or less size reduction, more or less aggregation or agglomeration, or both during processing, storage, or handling.

Methods of Forming Aqueous Fulvestrant Suspensions

In some embodiments of the invention, methods of forming an aqueous fulvestrant suspension comprise mixing an aqueous medium and at least one stabilizer to form a suspension vehicle, adding an amount of fulvestrant to the suspension vehicle, and dispersing the fulvestrant in the suspension vehicle to form the aqueous fulvestrant suspension. In further embodiments, these methods can further comprise homogenizing the aqueous fulvestrant suspension. In yet further embodiments, the methods with or without the homogenizing step can further comprise concentrating the fulvestrant suspension by phase separating the suspension and removing a portion of the supernatant. In particular further embodiments, after the concentrating step the methods can further comprise adding one or more electrolytes, non-electrolytes, buffering agents, or cross-linked polymers to the homogenized aqueous fulvestrant suspension and mixing the one or more electrolytes, non-electrolytes, buffering agents, or cross-linked polymers into the suspension. In some embodiments of the invention, the methods comprise a dispersing step performed using high shear mixing, a homogenizing step performed using high pressure homogenization, or both a dispersing step performed using high shear mixing and a homogenizing step performed using high pressure homogenization.

In further embodiments of the invention that include one or more stabilizers, the one or more stabilizers may be incorporated into the formulations at one or more stages of the methods of forming the formulations. In some embodiments, at least a portion or all of the stabilizers of a formulation are added to an aqueous medium along with an amount of fulvestrant prior to some or all of any mixing, homogenization, or supernatant-removal steps. In still other embodiments, at least a portion or all of the one or more stabilizers of a formulation are added to the fulvestrant suspensions after some or all of any mixing, homogenization, or supernatant-removal steps have been completed. In further embodiments, at least a portion or all of the surfactant and polymer stabilizers of the formulations are combined with the aqueous medium and fulvestrant prior to some or all of any mixing, homogenization, or supernatant-removal steps and at least a portion or all of the electrolyte, non-electrolyte, buffering agents, and cross-linked polymers of the formulations are added to the suspension after some or all of any mixing, homogenization, or supernatant-removal steps.

The fulvestrant particles described herein can be prepared in a method comprising the steps of dispersing fulvestrant particles in a liquid suspension medium and applying mechanical means in the presence of grinding media to reduce the particle size of fulvestrant to the desired size.

In further embodiments of the invention, a solvent, such as water, present in a formulation can be removed by appropriate techniques known to the art, such as lyophilization or spray drying, to form a dried formulation suitable for later reconstitution. Lyophilization can be used to produce a lyophilized (lyo) cake. The dried formulation can be reconstituted back into a liquid suspension using an appropriate diluent. Different volumes of diluent can be used to produce reconstituted suspensions with different fulvestrant concentrations as needed. The diluent can be aqueous in general but can further comprise an organic solvent and/or any excipient as described elsewhere herein.

In some embodiments of the invention, at least a portion of the formulation components other than fulvestrant can be omitted from the suspension and incorporated as part of the diluent and introduced into the suspension upon reconstitution by the diluent to arrive at the final formulation. In further embodiments, suspensions can be prepared with higher or lower concentrations of constituent components than desired in formulations for administration, formed into dried formulations and placed into vials in appropriate amounts of dried formulation to achieve target dose amounts of fulvestrant per vial for later reconstitution of diluent to form the desired formulation for administration.

Figure 15:
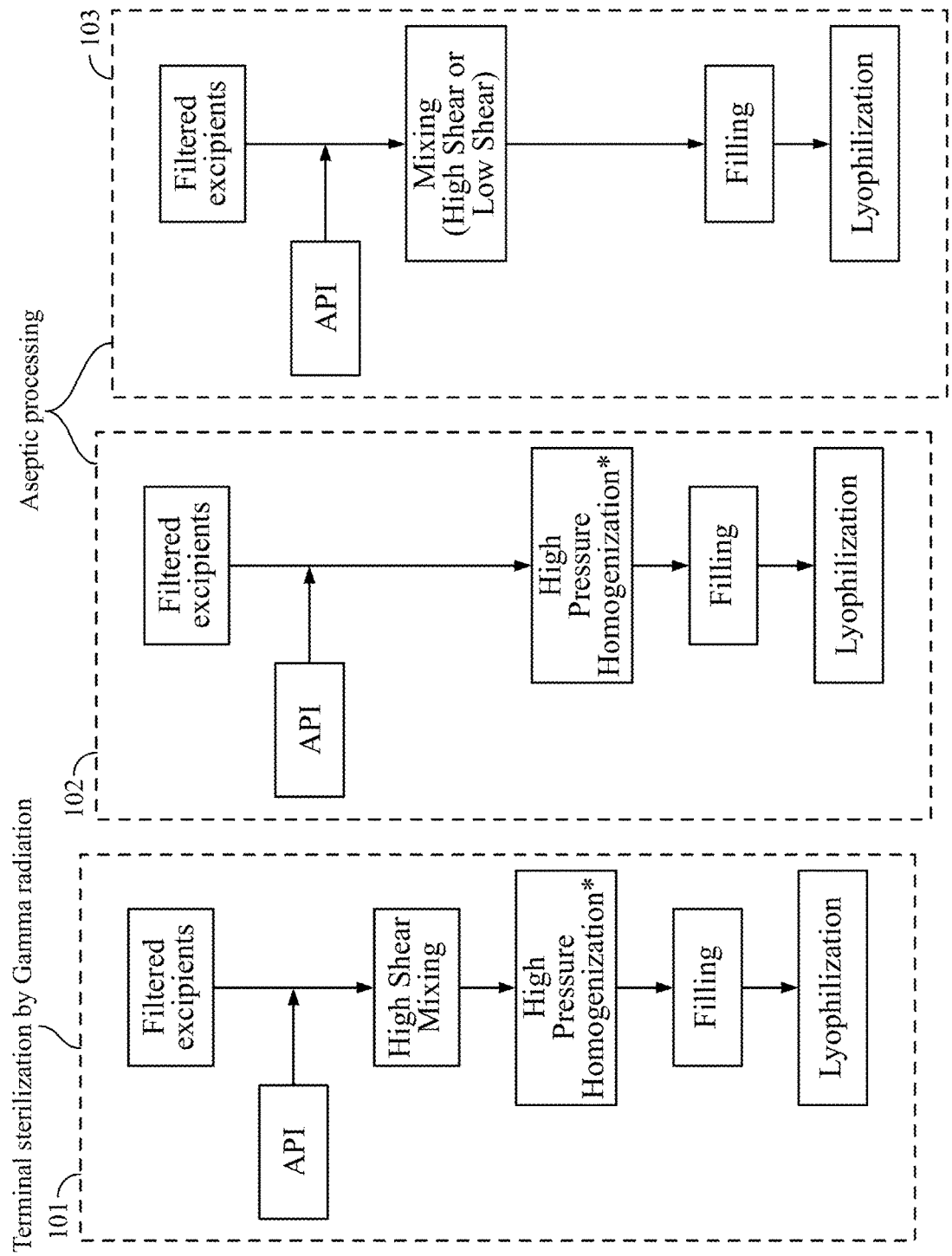
FIG. 15 depicts schematic representations of aspects of methods of preparation of some exemplary fulvestrant formulations of the present disclosure.

Some exemplary methods of preparation of dried pharmaceutical compositions are depicted schematically in FIG. 15.

In some embodiments, the pharmaceutical compositions and dried pharmaceutical compositions can be prepared using aseptic process or terminally sterilized by a compatible sterilization technique, such as, but not limited to, gamma irradiation. When a polymer is used as an excipient in the pharmaceutical composition, said polymer such as carboxymethylcellulose (CMC) or its salts including sodium CMC, can be sterilized by autoclave in a solution then combined with rest of the pharmaceutical composition that is prepared aseptically or terminally sterilized.

Some aspects of exemplary embodiments of methods of preparation of the invention are shown in Tables 4-7 and 23-27 and FIGS. 4-12 and 15 which describe aspects of the preparation methods for exemplary fulvestrant formulations.

TABLE 23

| Target Formulation (mg/mL) | B | E | I | J | K | L |
|---|---|---|---|---|---|---|
| Fulvestrant | 50 | 50 | 50 | 50 | 50 | 100 |
| Polysorbate 80 | 5 | 5 | 5 | 5 | 5 | 5 |
| PVP 12K | 0.8 | 0.8 | 0.8 | 0.8 | 0.8 | 0.8 |
| NaCl | — | — | 9 | 9 | 9 | 9 |
| Phosphate buffer | — | — | — | 10 mM | 10 mM | 10 mM |
| WFI | q.s. to | q.s. to | q.s. to | q.s, to | q.s. to volume | q.s. to volume |
| Starting API (PSD via laser diffraction) | Un-milled API L D Dv90: 780 microns | Un-milled API L D Dv90: 780 microns | Un-milled API L D Dv90: 780 microns | Un-milled API L D Dv90: 1890 microns | Un-milled API L D Dv90: 1890 microns | Un-milled API L D Dv90: 1890 microns |
| Manufacturing process | API size reduction by HSM | API size reduction by HSM followed by HPH | API size reduction by HSM followed by HPH, then subsequent salt addition | API size reduction by HSM followed by HPH in the presence of salts | API size reduction by HSM followed by HPH in the presence of salts, then further HSM | API size reduction by HSM followed by HPH in the presence of salts |
| Process End Point Targets (PSD via laser diffraction) | L D Dv90: 143 HSM at micron HSM: Total 15 min at ~20,000 rpm | Total 15 min HSM at ~20,000 rpm (L D Dv90: <~80 micron) HPH: 15 passes in reverse flow through z5 nozzle at ~30,000 psi L D Dv90: 11.1 micron | Total 42 min HSM at ~20,000 rpm (L D Dv90: <~40 micron) L D Dv90: 12.6 micron HPH: 30 passes in parallel flow through z5 nozzle at ~40,000 psi | Total 45 min HSM at ~25,000 rpm (L D Dv90: <~50 micron) L D Dv90: 11.8 micron HPH: 3 passes in parallel flow through z5 nozzle at ~40,000 psi | Total 45 min HSM at ~25,000 rpm (L D Dv90: <~50 micron) L D Dv90: 4.7 micron HPH: 12 passes in parallel flow through z5 nozzle at ~40,000 psi to L D Dv90: ~8 micron then additional 5 min HSM at ~25,000 rpm | Total 25 min HSM at ~25,000 rpm (L D Dv90: <~80 micron) L D Dv90: 13.8 microns HPH: 15 passes in parallel flow through z8 nozzle at ~30,000 psi |

TABLE 24

| Target Formulation (mg/mL) | L3F | L6 | F003a | F003b | F004a | F003e |
|---|---|---|---|---|---|---|
| Fulvestrant | 100 | 100 | 100 | 100 | 100 | 100 |
| Polysorbate 80 | 5 | 5 | 5 | 5 | 5 | 5 |
| PVP 12K | 0.8 | 0.8 | — | — | — | — |
| NaCl | 9 | 9 | — | — | — | — |
| Phospate buffer | 10 mM | 10 mM | — | — | 9 | — |
| Dextrose | — | — | 50 | 50 | — | 50 |
| WFI | q.s. to | q.s. to | q.s. to | q.s. to | q.s. to | q.s. to |
| Starting API (PSD via laser diffraction) | Un-milled API | Un-milled API LD Dv90: | Un-milled API LD Dv90: 240 micron | Un-milled API LD Dv90: 240 micron | Un-milled API LD Dv90: 240 micron | Jet-milled API |

TABLE 24-continued

| Target Formulation (mg/mL) | L3F | L6 | F003a | F003b | F004a | F003e |
|---|---|---|---|---|---|---|
| Manufacturing Process | API size reduction by HSM | API size reduction by HSM | API size reduction by HSM (F001e), then subsequent dextrose addition | API size reduction by HSM followed by HPH, then subsequent dextrose addition | API size reduction by HSM followed by HPH, then subsequent NaCl addition | API size dispersed by HSM and sonication/vortex |
| Process End Point Targets (PSD via laser diffraction) | LD Dv90: 14.7 micron and LD Dv50: 5.9 micron HSM: Total >120 min at ~25,000-30,000 rpm | LD Dv90: 17.6 micron and LD Dv50: 6.9 micron HSM: Total >120 min at ~25,000-30,000 rpm | LD Dv90: 13.6 micron and LD Dv50: 5.7 micron HSM: Total 60-120 min at ~25,000 rpm before dextrose addition to LD Dv90: 13.0 micron | Total 15 min HSM at ~25,000 rpm to target LD Dv90: <~40 micron LD Dv90: 15.1 micron HPH: 15 passes in parallel flow through z5 nozzle at ~40,000 psi before dextrose addition to LD Dv90: 12.1 micron pH = 7.3 | Total 15 min HSM at ~25,000 rpm to target LD Dv90: <~40 micron LD Dv90: 15.1 micron HPH: 15 passes in parallel flow through z5 nozzle at ~40,000 psi before NaCl addition to LD Dv90: 12.2 micron pH = 7.5 | LD Dv90: 12.2 micron HSM: Total 5 min at ~25,000 rpm to LD Dv90: 12.6 micron by sonication/vortex |

TABLE 25

| Target Formulation (mg/mL) | F003k2 | F003k3 | F003l | F005a2 |
|---|---|---|---|---|
| Fulvestrant | 100 | 100 | 100 | 100 |
| Polysorbate 80 | 5 | 5 | 5 | 5 |
| Dextrose | 50 | 50 | 50 | — |
| Mannitol | — | — | — | 50 |
| WFI | q.s. to | q.s. to | q.s. to volume | q.s. to volume |
| Starting API (PSD via laser diffraction) | Jet-mill API L D Dv90: 7-8 micron | Jet-mill API L D Dv90: 7-8 micron | Jet-mill API L D Dv90: 7-13 micron | Un-milled API L D Dv90: 240 micron |
| Manufacturing process | API dispersed by HSM, then subsequent dextrose addition | API dispersed by HSM then size reduction by HPH in the presence of dextrose | API dispersed by HSM (F003i, f, j). Suspension lyophilized, reconstituted then composited | API size reduction by HSM (F001e), then mannitol addition. Suspension lyophilized, reconstituted then composited. |
| Process End Point Targets (PSD via laser diffraction) | L D Dv90: 6.7 micron after dextrose addition HSM: Total 5 min at ~25,000 rpm | Total 5 min HSM at ~25,000 rpm (Dv90: 9.2 micron) for dispersing API L D Dv90: 13.3 micron HPH: 9 passes in parallel flow through z5 nozzle at ~40,000 psi; dextrose co-processed | Total 5 min HSM at ~25,000 rpm for dispersing each individual API lot F003i, f, j before lyophilization, L D Dv90: 7.0, 12.9, 7.3 Micron After reconstitution, L D Dv90: 121, 113, 113 micron. Composite F003l, L D Dv90: 112 micron | L D Dv90: 13.6 micron and L D Dv50: 5.7 micron HSM: Total 60-120 min at ~25,000 rpm before mannitol addition to L D Dv90: 13.2 micron (F005a) After lyophilization, reconstitution, composite F005a2, Dv90: 18.4 micron |

TABLE 26

| Target Formulation (mg/mL) | F005b1 | F005c2 | F0065c3 | F005d1 | F015a1 | F015a3 |
|---|---|---|---|---|---|---|
| Fulvestrant | 100 | 100 | 100 | 100 | 100 | 100 |
| Polysorbate 80 | 5 | 5 | 5 | 5 | 25 | 25 |
| Mannitol | 50 | 50 | 50 | 50 | 50 | 50 |
| WFI | q.s. to | q.s. to | q.s. to | q.s. to | q.s. to | q.s. to |
| Starting API (PSD via laser diffraction) | Jet-mill API L D Dv90: 7-8 micron | Jet-mill API L D Dv90: 7-8 micron | Jet-mill API L D Dv90: 7-8 micron | Jet-mill API L D Dv90: 7-8 micron | Jet-mill API L D Dv90: 7-8 micron | Jet-mill API L D Dv90: 7-8 micron |
| Manufacturing process | API dispersed by HSM in the presence of mannitol | API dispersed by HSM then size reduction by HPH in the presence of mannitol | Lyophilized F005c2 | API size reduction by HSM followed by HPH, then subsequent mannitol addition | API dispersed by HSM in the presence of mannitol | Lyophilized F015a1 |
| Process End Point Targets (PSD via laser diffraction) | L D Dv90: 7.9 micron HSM: Total 5 min at ~25,000 rpm | Total 5 min HSM at ~25,000 rpm for dispersing API (L D Dv90: ~7 micron) To HPH with 15 passes in parallel flow through z5 nozzle at ~40,000 psi resulted in L D Dv90: 17.2 micron pH = 7.1 | After reconstitution, L D Dv90: 112 micron | Total 5 min HSM at ~25,000 rpm for dispersing API (L D Dv90: ~7 micron) To HPH with 15 passes in parallel flow through z5 nozzle at ~40,000 psi resulted in Dv90: ~16 micron (F001h4) L D Dv90: 40 micron after mannitol addition pH = 7.1 | L D Dv90: 6.9 micron HSM: Total 5 min at ~25,000 rpm | After reconstitution, L D Dv90: 22.7 micron |

TABLE 27

| Target Formulation (mg/mL) | F015a4 | F017a1 | F01733 | F005g4 | F005g5 |
|---|---|---|---|---|---|
| Fulvestrant | 100 | 100 | 100 | 100 | 100 |
| Polysorbate 80 | 25 | 15 | 15 | 5 | 5 |
| Mannitol | 50 | 50 | 50 | 50 | 50 |
| WFI | Qs. to | Qs. to | q.s. to | Qs. to | q.s. to |
| Starting API (PSD via laser diffraction) | Jet-mill API L D Dv90: 7-8 micron | Jet-mill API L D Dv90: 7-8 iiticron | Jet-mill API L D Dv90: 7-8 micron | Recrystallized API L D Dv90: 18 micron | Recrystallized API L D Dv90: 18 micron |
| Manufacturing process | F015a3 gamma irradiated at 35 kGy | API dispersed by HSM in the presence of mannitol | Lyophilized, gamma irradiated (35 KGy) F017a1 | API dispersed by HSM in the presence of mannitol | Lyophilized F005g4 |
| Process End Point Targets (PSD via laser diffraction) | After reconstitution, L D Dv90: 22.7 micron | L D Dv90: 7.2 micron HSM: Total 5 min at ~25,000 rpm | After reconstitution, L D Dv90: 31.9 micron | Total 5 min HSM at ~25,000 rpm for dispersing API (L D Dv90: ~20 micron) L D Dv90: ~10 micron after HPH with 9 passes in parallel flow through z5 nozzle at | |

TABLE 27-continued

| Target Formulation (mg/mL) | F015a4 | F017a1 | F01733 | F005g4 | F005g5 |
|---|---|---|---|---|---|
| | | | | ~40,000 psi Final L D Dv90: 7.5 micron after concentration | |

D. Pharmacokinetics

In certain embodiments of the invention, the pharmaceutical compositions are bioequivalent to the commercial pharmaceutical composition, FASLODEX™. The single dose PK parameters in postmenopausal advanced breast cancer patients administered FASLODEX™ dosed intramuscularly with 500 mg with an additional dose at day 15 are reported as, in geometric mean and coefficient of variation (%), Cmax 25.1 (35.3) ng/mL, Cmin 16.3 (25.9) ng/mL, and AUC 11,400 (33.4) ng·hr/mL.

In further embodiments of the invention, the 90% confidence intervals (CI) of the relative mean $C_{max}$, $AUC_{(0-t)}$ and $AUC_{(0-\infty)}$ of the pharmaceutical composition of the invention is within 80% to 125% of the relative mean $C_{max}$, $AUC_{(0-t)}$ and $AUC_{(0-\infty)}$, respectively, of FASLODEX™. In yet further embodiments of the invention, the 90% confidence intervals (CI) of the relative mean $C_{max}$, $AUC_{(0-t)}$ and $AUC_{(0-\infty)}$ of the pharmaceutical composition of the invention is within 80% to 125% of the relative mean $C_{max}$, $AUC_{(0-t)}$ and $AUC_{(0-\infty)}$, respectively, of FASLODEX™ in the fasting state. In still further embodiments of the invention, the 90% confidence intervals (CI) of the relative mean $C_{max}$, $AUC_{(0-t)}$ and $AUC_{(0-\infty)}$ of the pharmaceutical composition of the invention is within 80% to 125% of the relative mean $C_{max}$, $AUC_{(0-t)}$ and $AUC_{(0-\infty)}$, respectively, of FASLODEX™ in the fed state.

In other embodiments of the invention, the 90% confidence intervals (CI) of the relative mean $C_{max}$, $AUC_{(0-t)}$ and $AUC_{(0-\infty)}$ of the pharmaceutical composition of the invention having a fulvestrant concentration of 100 mg/mL is within 80% to 125% of the relative mean $C_{max}$, $AUC_{(0-t)}$ and $AUC_{(0-\infty)}$, respectively, of FASLODEX™. In still other embodiments of the invention, the 90% confidence intervals (CI) of the relative mean $C_{max}$, $AUC_{(0-t)}$ and $AUC_{(0-\infty)}$ of the pharmaceutical composition of the invention having a fulvestrant concentration of 100 mg/mL is within 80% to 125% of the relative mean $C_{max}$, $AUC_{(0-t)}$ and $AUC_{(0-\infty)}$, respectively, of FASLODEX™ in the fasting state. In yet other embodiments of the invention, the 90% confidence intervals (CI) of the relative mean $C_{max}$, $AUC_{(0-t)}$ and $AUC_{(0-\infty)}$ of the pharmaceutical composition of the invention having a fulvestrant concentration of 100 mg/mL is within 80% to 125% of the relative mean $C_{max}$, $AUC_{(0-t)}$ and $AUC_{(0-\infty)}$, respectively, of FASLODEX™ in the fed state.

In particular embodiments of the invention, the pharmaceutical composition has the single dose and multiple dose pharmacokinetic parameters shown in Tables 28 and 29. Table 28 shows pharmacokinetic parameters for 500 mg dosage of pharmaceutical compositions of the disclosure. For the data labeled "Single Dose" in Table 28, the fulvestrant blood plasma concentration data are shown for a 500 mg initial dose with an additional 500 mg dose given on day 15. For the data labeled "Multiple Dose Steady State" in Table 28, the fulvestrant blood plasma concentration data are shown for measurement at month 3, after a 500 mg dosage on days 1, 15, 20, and once monthly thereafter. Table 29 shows pharmacokinetic parameters for a single 250 mg dosage of pharmaceutical compositions of the disclosure. In Table 29, data are expressed as geometric mean (CV %), except for $T_{max}$, which is shown as a median value with a range indicated in parentheses.

TABLE 28

| | $C_{max}$ (ng/mL) | $C_{min}$ (ng/mL) | AUC (ng · hr/mL) |
|---|---|---|---|
| Single Dose[1] | 20.08-31.375 | 13.04-20.375 | 9,120-14,250 |
| Multiple Dose Steady State[2] | 22.4-35.0 | 9.76-15.25 | 10,480-16,375 |

TABLE 29

| | I | II | III | IV | V | VI | VII |
|---|---|---|---|---|---|---|---|
| $C_{max}$ (µg/L) | 8.20 (63.8) | 4.76 (68.1) | 8.2 | 4-8.5 | 11.8 (6.6) | 8.3 (8.8) | 8-12 |
| $C_{min}$ (µg/L) | 2.62 (33.4) | 2.38 (47.7) | 2.6 | 2.0-3.0 | | | |
| $T_{max}$ (days) | 6.97 (1.86-7.95) | 8.8 (6.97-12.0) | 7 | 6-9 | 4.2 (8.3) | 4.6 (11.2) | 4-5 |
| $AUC_{28}$ (µg · day/L) | 148 (45.3) | 88.4 (47.3) | 148 | 80-150 | 369 (4.1) | 333 (3.0) | 325-375 |

In particular embodiments, a dose of about 500 mg of a fulvestrant pharmaceutical composition of the invention is bioequivalent to 500 mg of the commercial pharmaceutical composition, FASLODEX™. In certain embodiments, a dose of less than 500 mg of a fulvestrant pharmaceutical composition of the invention is bioequivalent to 500 mg of the commercial pharmaceutical composition, FASLODEX™. In further embodiments, a dose of about 400 to 450 mg of a fulvestrant pharmaceutical composition of the invention is bioequivalent to 500 mg of the commercial pharmaceutical composition, FASLODEX™. In still further embodiments, a dose of about 350 to 400 mg of a fulvestrant pharmaceutical composition of the invention is bioequivalent to 500 mg of the commercial pharmaceutical composition, FASLODEX™. In yet further embodiments, a dose of about 300 to 350 mg of a fulvestrant pharmaceutical composition of the invention is bioequivalent to 500 mg of the commercial pharmaceutical composition, FASLODEX™. In even further embodiments, a dose of about 250 to 300 mg of a fulvestrant pharmaceutical composition of the invention is bioequivalent to 500 mg of the commercial pharmaceutical composition, FASLODEX™.

In other embodiments of the invention, a 500 mg dose of a pharmaceutical composition of the invention provides 90% confidence intervals (CI) of the relative mean $C_{max}$, $AUC_{(0-t)}$ and $AUC_{(0-\infty)}$ within 80% to 125% of the relative mean $C_{max}$, $AUC_{(0-t)}$ and $AUC_{(0-\infty)}$, respectively, of a 500 mg dose of FASLODEX™.

In other embodiments of the invention, a dose of less than 500 mg of a pharmaceutical composition of the invention provides 90% confidence intervals (CI) of the relative mean $C_{max}$, $AUC_{(0-t)}$ and $AUC_{(0-\infty)}$ within 80% to 125% of the relative mean $C_{max}$, $AUC_{(0-t)}$ and $AUC_{(0-\infty)}$, respectively, of a 500 mg dose of FASLODEX™.

In some embodiments of the invention, fulvestrant pharmaceutical compositions of the invention can be administered as a single intramuscular injection, with the 90% confidence intervals (CI) of the relative mean Cmax, AUC (0–t) and AUC(0–∞) of fulvestrant is within 80% to 125% of the relative mean Cmax, AUC(0–t) and AUC(0–∞), respectively, of fulvestrant after administration of 500 mg of fulvestrant in the form of FASLODEX™ administered intramuscularly as two 5 mL injections. In further embodiments, such fulvestrant pharmaceutical compositions administered as a single intramuscular injection comprise a dose of about 500 mg of fulvestrant. In yet further embodiments, such fulvestrant pharmaceutical compositions administered as a single intramuscular injection comprise a dose of about 500 mg of fulvestrant in an injection volume of about 3.0 mL to about 5.0 mL, about 3.5 mL to about 4.5 mL, or about 4.0 mL.

In certain embodiments of the invention, the 90% confidence intervals (CI) of the relative mean $AUC_{(0-t)}$, relative mean $AUC_{(0-\infty)}$, or both of fulvestrant pharmaceutical compositions of the invention is within 80% to 125% of the relative mean $AUC_{(0-t)}$ and relative mean $AUC_{(0-\infty)}$, respectively, of FASLODEX™, and the relative mean $C_{max}$ of fulvestrant pharmaceutical compositions of the invention is less than 80% of the relative mean Cmax of FASLODEX™. It is believed that such embodiments may provide benefits by providing a therapeutically effect amount of fulvestrant exposure to a subject while reducing the degree of one or more Cmax-driven side-effects or toxicities in comparison to the degree of side-effects or toxicities experienced by a subject from receiving a therapeutically effective amount of fulvestrant exposure from one or more dosages of FASLODEX™.

In some embodiments of the invention, the 90% confidence intervals (CI) of the relative mean $AUC_{(0-t)}$, relative mean $AUC_{(0-\infty)}$, or both of fulvestrant pharmaceutical compositions of the invention is within 80% to 125% of the relative mean $AUC_{(0-t)}$ and relative mean $AUC_{(0-\infty)}$, respectively, of FASLODEX™, and the relative mean Cmax of fulvestrant pharmaceutical compositions of the invention is less than 80%, less than 75%, less than 70%, less than 65%, less than 60%, less than 55%, less than 50%, less than 45%, or less than 40% of the relative mean Cmax of FASLODEX™. In further embodiments, such fulvestrant pharmaceutical compositions are administered as a single intramuscular injection and comprise a dose of about 500 mg of fulvestrant at a concentration of about 100 mg/mL.

In yet further embodiments of the invention, the 90% confidence intervals (CI) of the relative mean $AUC_{(0-t)}$, relative mean $AUC_{(0-\infty)}$, or both of fulvestrant pharmaceutical compositions of the invention is within 80% to 125% of the relative mean $AUC_{(0-t)}$ and relative mean $AUC_{(0-\infty)}$, respectively, of FASLODEX™, and the relative mean $C_{max}$ of fulvestrant pharmaceutical compositions of the invention is less than 80%, less than 75%, less than 70%, less than 65%, less than 60%, less than 55%, less than 50%, less than 45%, or less than 40% of the relative mean $C_{max}$ of FASLODEX™ in the fasting state. In further embodiments, such fulvestrant pharmaceutical compositions are administered as a single intramuscular injection and comprise a dose of about 500 mg of fulvestrant at a concentration of about 100 mg/mL.

In still further embodiments of the invention, the 90% confidence intervals (CI) of the relative mean $AUC_{(0-t)}$, relative mean $AUC_{(0-\infty)}$, or both of fulvestrant pharmaceutical compositions of the invention is within 80% to 125% of the relative mean $AUC_{(0-t)}$ and relative mean $AUC_{(0-\infty)}$, respectively, of FASLODEX™, and the relative mean Cmax of fulvestrant pharmaceutical compositions of the invention is less than 80%, less than 75%, less than 70%, less than 65%, less than 60%, less than 55%, less than 50%, less than 45%, or less than 40% of the relative mean Cmax of FASLODEX™ in the fed state. In further embodiments, such fulvestrant pharmaceutical compositions are administered as a single intramuscular injection and comprise a dose of about 500 mg of fulvestrant at a concentration of about 100 mg/mL.

In some embodiments of the invention, the 90% confidence intervals (CI) of the relative mean $AUC_{(0-t)}$, relative mean $AUC_{(0-\infty)}$, or both of fulvestrant pharmaceutical compositions of the invention is within 80% to 125% of the relative mean $AUC_{(0-t)}$ and relative mean $AUC_{(0-\infty)}$, respectively, of FASLODEX™, and the relative mean Cmax of fulvestrant pharmaceutical compositions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX™. In further embodiments, such fulvestrant pharmaceutical compositions are administered as a single intramuscular injection and comprise a dose of about 500 mg of fulvestrant at a concentration of about 100 mg/mL.

In yet further embodiments of the invention, the 90% confidence intervals (CI) of the relative mean $AUC_{(0-t)}$, relative mean $AUC_{(0-\infty)}$, or both of fulvestrant pharmaceutical compositions of the invention is within 80% to 125% of the relative mean $AUC_{(0-t)}$ and relative mean $AUC_{(0-\infty)}$, respectively, of FASLODEX™, the relative mean Cmax of fulvestrant pharmaceutical compositions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX™ in the fasting state. In further embodiments, such fulvestrant pharmaceutical compositions are administered as a single intramuscular injection and comprise a dose of about 500 mg of fulvestrant at a concentration of about 100 mg/mL.

In still further embodiments of the invention, the 90% confidence intervals (CI) of the relative mean $AUC_{(0-t)}$, relative mean $AUC_{(0-\infty)}$, or both of fulvestrant pharmaceutical compositions of the invention is within 80% to 125% of the relative mean $AUC_{(0-t)}$ and relative mean $AUC_{(0-\infty)}$, respectively, of FASLODEX™, and the relative mean Cmax of fulvestrant pharmaceutical compositions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX™ in the fed state. In further embodiments, such fulvestrant pharmaceutical compositions are administered as a single intramuscular injection and comprise a dose of about 500 mg of fulvestrant at a concentration of about 100 mg/mL.

E. Methods of Treatment

In further embodiments, the invention is directed to methods of treatment comprising administration of a pharmaceutically effective amount of any of the fulvestrant pharmaceutical compositions described herein to a patient in need thereof. In particular embodiments, the invention is directed to a method of treating breast cancer, comprising administering a pharmaceutically acceptable amount of any of the fulvestrant pharmaceutical compositions described herein. In certain embodiments, the breast cancer is metastatic breast cancer. In other embodiments of the invention, the breast cancer is hormone receptor (HR)-positive breast cancer. In still other embodiments of the invention, the invention is directed to a method of treating hormone receptor (HR)-positive breast cancer in a post-menopausal woman comprising administration of a pharmaceutically effective amount of any of the fulvestrant pharmaceutical compositions described herein. In yet other embodiments, the invention is directed to a method of treating hormone receptor (HR)-positive breast cancer in a post-menopausal woman with disease progression following antiestrogen therapy comprising administration of a pharmaceutically effective amount of any of the fulvestrant pharmaceutical compositions described herein. In yet further embodiments, the invention is directed to a method of treating HR-positive, human epidermal growth factor receptor 2 (HER2)-negative advanced or metastatic breast cancer in a woman with disease progression after endocrine therapy.

In particular embodiments of the invention, a fulvestrant pharmaceutical composition as described herein is administered on days 1, 15, 29, and once monthly thereafter. In further embodiments of the invention, a 500 mg dose of any of the fulvestrant pharmaceutical compositions as described herein is administered on days 1, 15, 29, and once monthly thereafter. In still further embodiments of the invention, a 250 mg dose of any of the fulvestrant pharmaceutical compositions as described herein is administered on days 1, 15, 29, and once monthly thereafter.

In certain embodiments of the invention, a fulvestrant pharmaceutical composition as described herein is administered as a single injection. In other embodiments of the invention, a 500 mg dose of any of the fulvestrant pharmaceutical compositions as described herein is administered as a single injection. In yet other embodiments of the invention, a 500 mg dose of any of the fulvestrant pharmaceutical compositions as described herein is administered as a single 5 mL injection. In further embodiments of the invention, a 500 mg dose of any of the fulvestrant pharmaceutical compositions as described herein is administered as a single 4 mL injection. In yet further embodiments, a 500 mg dose of any of the fulvestrant pharmaceutical compositions as described herein is administered as a single 3 mL injection. In still other embodiments of the invention, a 250 mg dose of any of the fulvestrant pharmaceutical compositions as described herein is administered as a single injection. In further embodiments of the invention, a 250 mg dose of any of the fulvestrant pharmaceutical compositions as described herein is administered as a single 2.5 mL injection. In yet further embodiments of the invention, a 250 mg dose of any of the fulvestrant pharmaceutical compositions as described herein is administered as a single 5 mL injection.

In particular embodiments of the invention, a fulvestrant pharmaceutical composition as described herein is administered as two injections. In further embodiments of the invention, a 500 mg dose of any of the fulvestrant pharmaceutical compositions as described herein is administered as two injections. In still further embodiments of the invention, a 500 mg dose of any of the fulvestrant pharmaceutical compositions as described herein is administered as two 5 mL injections. In yet further embodiments of the invention, a 500 mg dose of any of the fulvestrant pharmaceutical compositions as described herein is administered as two 2 mL injections, two 2.5 mL injections, two 3 mL injections, two 3.5 mL injections, or two 4 mL injections. In other embodiments of the invention, a 250 mg dose of any of the fulvestrant pharmaceutical compositions as described herein is administered as two injections. In yet other embodiments of the invention, a 250 mg dose of any of the fulvestrant pharmaceutical compositions as described herein is administered as two 2.5 mL injections.

The fulvestrant pharmaceutical compositions described herein may be administered alone, or in combination with one or more additional therapeutic agents as defined herein. An additional therapeutic agent may be used to treat one or more core symptoms and/or comorbidities associated with cancer in general or breast cancer in particular. In one aspect, fulvestrant is formulated (and administered) with at least one therapeutic agent as a fixed dose. In another aspect, fulvestrant is formulated (and administered) separately from the therapeutic agent(s).

Some examples of therapeutic agents that may be used in combination with fulvestrant include, but are not limited to, e.g., a EGFR kinase inhibitor, a PDGFR kinase inhibitor, a FGFR kinase inhibitor, or any of the other cytotoxic, chemotherapeutic, antihormonal, anti-angiogenic, antiproliferative, pro-apoptotic, anti-HER2, radiation or a radiopharmaceutical, signal transduction inhibitors, or other anti-cancer agents or treatments. Examples of particular agents that can be used in combination with the fulvestrant pharmaceutical compositions of the disclosure include palbociclib, letrozole, anastrozole, doxorubicin, paclitaxel, docetaxel, vinorelbine, and 5-fluorouracil. In other embodiments, therapeutic agents that may be used in combination with fulvestrant include, but are not limited to, agents or treatments for one or more of pain, nausea, emesis, hot flushes, constipation, and dizziness.

Those skilled in the art will appreciate that numerous changes and modifications can be made to the preferred embodiments of the disclosure and that such changes and modifications can be made without departing from the spirit of the disclosure. It is, therefore, intended that the following examples and appended claims cover all such equivalent variations as fall within the true spirit and scope of the disclosure.

The disclosures of each patent, patent application, and publication cited or described in this document are hereby incorporated herein by reference, in its entirety.

EXAMPLES

Example: Preparation of Fulvestrant Pharmaceutical Compositions/Variants

Some exemplary fulvestrant pharmaceutical compositions were prepared with 50 mg/mL and 100 mg/mL concentrations of fulvestrant in aqueous suspensions. Tables 1-20 show aspects of the pharmaceutical compositions of the pharmaceutical compositions and the methods of preparation of some of the pharmaceutical compositions, also referred to as formulations, variants, or Lots in the Tables. Tables 4-7 and 23-27 and FIGS. 4-12 and 15 show aspects of the methods of preparation used to prepare some of the pharmaceutical compositions.

Where indicated in the Tables and Figures, the formulations B, E, I, J, K, L, L3F, L6, F003a, F003b, F003e, F004a, F003k2, F003k3, F005a2, F003l, F005b1, F015a1, F015a3, F005d1, F005c3, F005g5 tested in Studies 1-3 below were prepared via one or more of process steps of (1) low shear mixing, indicated in the Tables 23-27 and FIGS. 4-12 as "Mix" or "Mix with Vortex Mixer" steps; (2) high shear mixing, indicated as "HSM" or "Homogenize" steps; (3) high pressure homogenization, indicated as "HPH" or "Process with Nano DeBee" steps; (4) concentration via supernatant removal; and (5) application of sonication. Where indicated, supernatant removal was performed by phase separating the pharmaceutical composition and withdrawing the desired amount of supernatant to concentrate the suspensions to the target concentrations of fulvestrant, either 50 mg/mL or 100 mg/mL, depending on the pharmaceutical composition. Where indicated, phase separation was performed by overnight settling in a clear glass centrifuge tube. Application of centrifuge for phase separation could also be utilized.

Fulvestrant active pharmaceutical ingredient (which may also be referred to as "API" herein and in the Tables and Figures) was obtained in un-milled forms or in milled, micronized, or recrystallized forms from commercial suppliers. As-obtained particle size distributions for un-milled API varied from an LD Dv(90) of about 240 microns to an LD Dv(90) of about 2130 microns. As-obtained particle size distributions for milled, micronized, and recrystallized API varied from an LD Dv(90) of about 7 microns to an LD Dv(90) of about 18 microns. Fulvestrant API may be obtained in various particle size distributions from commercial sources and processed as described elsewhere herein to achieve the desired particle size distributions. Particle size distributions can be monitored throughout the processing steps through analysis of samples as described elsewhere herein.

Where indicated in the Tables and Figures, the formulations B, E, I, J, K, L, L3F, L6, F003a, F003b, F003e, F004a, F003k2, F003k3, F005a2, F003l, F005b1, F015a1, F015a3, F005d1, F005c3, F005g5 tested in Studies 1-3 below were prepared via high shear mixing (HSM) steps. The preparation of formulations can be performed with an IKA T10 Basic Disperser with an IKA S 10N-10G dispersing tool. At the speeds indicated (~20,000 to 30,000 rpm), the mixture of fulvestrant and suspension vehicle was processed in cycles until the total processing time indicated was reached. Between each cycle, a formulation was vortexed at ~3000 rpm for 30 seconds then sonicated for 1 minute to remove or reduce foam generated during the high shear mixing by the disperser. Formulations were also rested as needed in between cycles at room temperature to allow the disperser to cool down and avoid overheating of the product and the equipment. Sonication was performed with a Branson 3800 Ultrasonic Bath (Branson Ultrasonics Corp., Danbury, CT) at a frequency of 40 kHz. Other mixing and ultrasonic apparatuses may also be used to achieve mixing and particle size distribution as desired.

In some embodiments, high pressure homogenization was performed. In certain embodiments, high pressure homogenization (HPH) steps were performed with a Nano DeBEE High Pressure Homogenizer (BEE International, South Easton, MA) in a Labconco XPert Filtered Balance System (Model 3950630) (Labconco, Kansas City, MO), installed the 100 ml sample holder and Z5 nozzle in parallel flow configuration on Nano DeBEE High Pressure Homogenizer. The homogenizer was primed with filing water until the process pressure reached the processing pressure as indicated in the Tables and Figures. Water was removed from the system using the plunger to minimize the dilution of the batch by the residual priming water. Approximately ~50 ml of the suspension for HPH processing was loaded from the 50 mL clear Pyrex glass bottle on Nano DeBEE High Pressure Homogenizer. The Nano DeBEE was run in continuous mode until the pressure reached the indicated target processing pressure. The suspension was then processed for the indicated number passes at the processing pressure. To avoid losing the prime of the system and consequently the processing pressure, only total ~40 mL (8 strokes of ~5 mL per stroke) of the suspension was processed and collected from each pass. The 40 mL suspension was then loaded back to the reservoir for the suspension to be processed in the next pass. After the processing was completed, 40 ml fine suspension was collected in a 100 mL clear Pyrex glass bottle by running Nano DeBEE High Pressure Homogenizer until no sample was pumped out. In certain embodiments, high pressure homogenization was performed with other apparatuses at processing pressures ranging from about 5,000 psi to about 45,000 psi. Other high pressure homogenization apparatuses may also be used to achieve the desired particle size distributions described herein.

Some formulations for Study 3 below were lyophilized and reconstituted with sterile water for injection, USP prior to administration, as indicated in the Example below.

References to "Assay" refers to high-performance liquid chromatography (HPLC) measurement of the fulvestrant concentration of the pharmaceutical composition at intermediate processing steps or in final result as prepared. The "Assay" results are given in absolute measured mg/mL or as a percentage (%) or (% LC), where percentages indicate the concentration of fulvestrant relative to the 50 mg/mL label claim of the commercially available FASLODEX™ product. Total impurities were also measured and are provided in the figures as a percentage by area (% a/a) where indicated. HPLC was performed with Agilent Technologies Agilent 1260 Infinity Quaternary LC module G1311B (Agilent Technologies, Santa Clara, CA). Other HPLC apparatuses may also be used to analyze the fulvestrant concentrations.

In some aspects, particle size and particle size distributions were analyzed with Malvern Mastersizer 3000 (Malvern Instruments Ltd., Malvern, Worcestershire, UK), with an attached sample dispersion unit with an in-line sonication probe for agglomerate dispersion prior to analysis via laser diffraction.

In some aspects, particle size and particle size distributions were analyzed with Malvern Morphologi G3 (Malvern Instruments Ltd., Malvern, Worcestershire, UK), to determine circle equivalent (CE) diameters via microscopy image capture and analysis.

Measurements of pH were obtained at ambient room temperature with a Thermo Scientific Orion Star A211 pH Meter (Thermo Fisher Scientific Inc., Waltham, MA).

Example: Pharmacokinetic Study 1 of Intramuscular Administration to Female Dogs

Fulvestrant pharmaceutical compositions B, E, I, J, K, and L were prepared as described elsewhere herein and in the Figures. A preclinical study was performed to determine the pharmacokinetics of the pharmaceutical compositions following a single intramuscular administration of 15.4 mg/kg to female dogs. The pharmacokinetics of 15.4 mg/kg IM FASLODEX™ (fulvestrant injection, 250 mg/5 mL) were also determined and used for comparison to the three prototype pharmaceutical compositions. The 15.4 mg/kg dose used in this study is the canine equivalent, in mg/m$^2$, of the maximum dose (500 mg) for human use and was scaled for use in canine by dividing the dose (based on a 60 kg human) by a canine species conversion factor of 0.54.

Twenty-four non-naïve female beagle dogs were used in the study. The animals weighed between approximately 5-10 kg. Animal welfare for this study was in compliance with the U.S. Department of Agriculture's (USDA) Animal Welfare Act (9 Code of Federal Regulations (CFR) Parts 1, 2 and 3). The Guide for the Care and Use of Laboratory Animals, Institute of Laboratory Animal Resources, National Academy Press, Washington, D.C., was followed. The facility maintained an Animal Welfare Assurance statement with the National Institutes of Health, Office of Laboratory Animal Welfare.

The FASLODEX™ test articles contained a small molecule that was used as received and no adjustment was made for purity, salt correction, etc. The FASLODEX™ test articles were gently agitated prior to dispensing and dose delivery. Pharmaceutical Composition B, Pharmaceutical Composition E, Pharmaceutical Composition I, Pharmaceutical Composition J, Pharmaceutical Composition K, and Pharmaceutical Composition L were stored at room temperature and protected from light prior to use, and gently agitated prior to dispensing and dose delivery.

The animals were not fasted prior to dosing. Each animal received a single intramuscular (IM) dose of only one of the appropriate test article pharmaceutical compositions as outlined in the following study design table, Table 30. IM doses were administered with a 20 G needle via bolus injection into the same large muscle mass (using the Z-track injection technique) in the left hind limb of each animal. Attempts were made for consistent injections between animals [selection of the dose site (muscle), depth, etc.]. The hair was clipped from the injection site prior to dosing. The injection site was marked following dosing and remarked as necessary throughout the study. Specifications for all dose delivery were recorded and reported in the study report [including, but not limited to needle gauge/length, syringe size/barrel type with manufacturer and part number, estimated injection depth into the muscle, approximate duration required to administer the injection; any substantial resistance (either flow through the syringe/needle and/or into the muscle during administration)] was documented.

TABLE 30

| Group | Test Article | No of Females | Pharmaceutical Composition Fulvestrant Concentration (mg/mL) | Dose Level (mg/kg) | Dose Volume (mL/kg) |
|---|---|---|---|---|---|
| 1 | FASLODEX ™ | 3 | 50 | 15.4 | 0.308 |
| 2 | Pharmaceutical Composition B | 3 | 50 | 15.4 | 0.308 |
| 3 | Pharmaceutical Composition E | 3 | 50 | 15.4 | 0.308 |
| 4 | FASLODEX ™ | 3 | 50 | 15.4 | 0.308 |
| 5 | Pharmaceutical Composition I | 3 | 50 | 15.4 | 0.308 |
| 6 | Pharmaceutical Composition J | 3 | 50 | 15.4 | 0.308 |
| 7 | Pharmaceutical Composition K | 3 | 50 | 15.4 | 0.308 |
| 8 | Pharmaceutical Composition L | 3 | 100 | 15.4 | 0.154 |

All animals were observed at least twice a day for morbidity, mortality, injury, and availability of food and water. Any animals in poor health were identified for further monitoring and possible euthanasia.

Blood samples were collected at various time intervals to measure the blood plasma concentration of fulvestrant. Blood samples for Groups 1-3 were collected predose and at 0.25, 0.5, 1, 2, 4, 8, and 12 (on Day 1); and 24 (on Day 2), 48 (on Day 3), 120 (on Day 6), 192 (on Day 9), 264 (on Day 12), 336 (on Day 15), 384 (on Day 17), 456 (on Day 20), 528 (on Day 23), 600 (on Day 26), and 672 (on Day 29) hours postdose. Blood samples for Groups 4-8 were collected predose and at 0.25, 0.5, 1, 2, 4, 8, and 12 (on Day 1); and 24 (on Day 2), 48 (on Day 3), 72 (on Day 4), 96 (on Day 5), 120 (on Day 6), 192 (on Day 9), 264 (on Day 12), 336 (on Day 15), 384 (on Day 17), 528 (on Day 23), and 672 (on Day 29) hours postdose.

Whole venous blood samples of approximately 2 mL each were collected from a peripheral vein of all animals for determination of fulvestrant exposure. Blood was collected with sodium heparin anticoagulant (glass tube, no gel separator). All blood samples were placed on wet ice following collection until centrifuged. Blood was centrifuged at 3500 rpm for 7 minutes at 2 to 8° C. Plasma (minimum of 0.8 mL volume) was separated from blood cells within 0.75 hours of blood collection and frozen. Plasma samples were initially placed on dry ice prior to being stored in the appropriate freezer (−60 to −90° C.). Samples were shipped on dry ice for bioanalytical analysis.

A model independent method was used to determine $C_{max}$ and AUC values from fulvestrant plasma concentration-time data. Results are shown in Tables 31-37 and FIGS. 1B, 2A, 2C, and 3. Table 31 shows the pharmacokinetic data from the 15.4 mg/kg dosages as nominally dosed (based on the target fulvestrant concentration for each pharmaceutical composition). An "Assay %" is shown for the fulvestrant pharmaceutical compositions of the present disclosure used in the study. The "Assay %" represents the percentage equivalence of the particular pharmaceutical composition in comparison to the FASLODEX™ label claim fulvestrant concentration, with "Assay %" values determined via HPLC, measurement samples taken pre- and post-dose, with one value selected for normalization. The data in Tables 32-37 are normalized using the "Assay %" values to compare PK results based upon the actual mg/kg of fulvestrant administered, assuming linear scaling. FIGS. 1B, 2A, 2C, and 3 depict graphs of the dose normalized fulvestrant mean plasma concentrations.

TABLE 31

PK parameters based upon the nominal dose 15.4 mg/kg

| Variant (Geometric Mean of n as indicated) | Cmax (ng/mL) | AUC0-14d (hr * ng/mL) | AUC0-28d (hr * ng/mL) | Assay (%) (measured predose) Starred value used for normalization | Assay (%) (measured post-dose) |
|---|---|---|---|---|---|
| Faslodex (LW466, n = 9) | 35.0 | 7015 | 8917 | | |
| Faslodex (MB122, n = 6) | 45.7 | 7666 | 9306 | | |
| Faslodex (MB948, n = 3) | 32.0 | 7177 | 9018 | | |
| Faslodex (MC949, n = 4) | 36.9 | 8149 | 9817 | | |
| Faslodex (All, n = 22) | 37.5 | 7408 | 9195 | | |
| B (n = 3) | 8.7 | 1930 | 3250 | 100.0* | 138.9 |
| E (n = 3) | 29.1 | 5750 | 8380 | 93.4* | 91.8 |
| I (n = 3) | 41.5 | 8840 | 12300 | 95.6* | 99.6 |
| J (n = 3) | 44.8 | 5750 | 8100 | 87.6* | 93.6 |
| K (n = 3) | 69.7 | 7540 | 9630 | 84.6* | 91.2 |
| L (n = 3) | 63.9 | 8430 | 11000 | 94.1* | 97.3 |
| L3F (n = 3) | 22.6 | 5140 | 7130 | 83.8* | 79.0 |
| L6 (n = 3) | 24.7 | 6050 | 9360 | 113.9* | 113.9 |
| F003a (n = 3) | 27.7 | 5860 | 8610 | 95.0* | 97.1 |
| F003b (n = 3) | 32.5 | 7210 | 9650 | 96.3* | |
| F003e (n = 3) | 28.5 | 6400 | 9080 | 100.6* | 100.5 |
| F004a (n = 3) | 31.7 | 4310 | 6190 | 99.8* | 100.4 |
| F003k2 (n = 4) | 33 | 3910 | 5960 | 97.8* | 100.1 |
| F003k3 (n = 4) | 26.8 | 5430 | 7060 | 99.6* | 100.7 |
| F005a2 (L, n = 3) | 19.7 | 4370 | 6840 | — | 93.2* |
| F003l (L, n = 3) | 25.1 | 5510 | 8680 | — | 99.2* |
| F005b1 (n = 3) | 49.7 | 9420 | 12100 | 100.2* | — |
| F015a1 (n = 3) | 63.6 | 4750 | 7120 | 103.8* | — |
| F015a3 (L, n = 3) | 34.4 | 3850 | 6000 | — | 98.6* |
| F005d1 (n = 3) | 37.9 | 7180 | 9910 | 100.5* | 99.2 |
| F005c3 (L, n = 3) | 17.7 | 3680 | 5820 | 95.2* | |

TABLE 32

PK parameters normalized against the actual dose

| Variant (Geometric Mean of n as indicated) | Cmax (ng/mL per mg/kg) | AUC0-14d (hr * ng/mL per mg/kg) | AUC0-28d (hr * ng/mL per mg/kg) |
|---|---|---|---|
| Faslodex (LW466, n = 9) | 2.3 | 456 | 579 |
| Faslodex (MB122, n = 6) | 3.0 | 498 | 604 |
| Faslodex (MB948, n = 3) | 2.1 | 466 | 586 |
| Faslodex (MC949, n = 4) | 2.4 | 529 | 637 |
| Faslodex (All, n = 22) | 2.4 | 481 | 597 |
| B (n = 3) | 0.6 | 125 | 211 |
| E (n = 3) | 2.0 | 400 | 583 |
| I (n = 3) | 2.8 | 600 | 835 |
| J (n = 3) | 3.3 | 426 | 600 |
| K (n = 3) | 5.3 | 579 | 739 |
| L (n = 3) | 4.4 | 582 | 759 |
| L3F (n = 3) | 1.8 | 398 | 552 |
| L6 (n = 3) | 1.4 | 345 | 534 |
| F003a (n = 3) | 1.9 | 401 | 589 |
| F003b (n = 3) | 2.2 | 486 | 651 |
| F003e (n = 3) | 1.8 | 413 | 586 |
| F004a (n = 3) | 2.1 | 280 | 403 |
| F003k2 (n = 4) | 2.2 | 260 | 396 |
| F003k3 (n = 4) | 1.7 | 354 | 460 |
| F005a2 (L, n = 3) | 1.4 | 304 | 477 |
| F003l (L, n = 3) | 1.6 | 361 | 568 |
| F005b1 (n = 3) | 3.2 | 610 | 784 |
| F015a1 (n = 3) | 4.0 | 297 | 445 |
| F015a3 (L, n = 3) | 2.3 | 254 | 395 |
| F005d1 (n = 3) | 2.4 | 464 | 640 |
| F005c3 (L, n = 3) | 1.2 | 251 | 397 |

TABLE 33

Comparison of normalized PK parameters against all Faslodex lots

| Variant (Geometric Mean of n as indicated) | Cmax ratio to Faslodex (%) | AUC0-14d ratio to Faslodex (%) | AUC0-28d ratio to Faslodex (%) |
|---|---|---|---|
| Faslodex (LW466, n = 9) | 93 | 95 | 97 |
| Faslodex (MB122, n = 6) | 122 | 103 | 101 |
| Faslodex (MB948, n = 3) | 85 | 97 | 98 |
| Faslodex (MC949, n = 4) | 98 | 110 | 107 |
| Faslodex (All, n = 22) | 100 | 100 | 100 |
| B (n = 3) | 23 | 26 | 35 |
| E (n = 3) | 83 | 83 | 98 |
| I (n = 3) | 116 | 125 | 140 |
| J (n = 3) | 136 | 89 | 101 |

TABLE 33-continued

Comparison of normalized PK parameters against all Faslodex lots

| Variant (Geometric Mean of n as indicated) | Cmax ratio to Faslodex (%) | AUC0-14d ratio to Faslodex (%) | AUC0-28d ratio to Faslodex (%) |
|---|---|---|---|
| K (n = 3) | 219 | 120 | 124 |
| L (n = 3) | 181 | 121 | 127 |
| L3F (n = 3) | 72 | 83 | 93 |
| L6 (n = 3) | 58 | 72 | 89 |
| F003a (n = 3) | 78 | 83 | 99 |
| F003b (n = 3) | 90 | 101 | 109 |
| F003e (n = 3) | 75 | 86 | 98 |
| F004a (n = 3) | 85 | 58 | 67 |
| F003k2 (n = 4) | 90 | 54 | 66 |
| F003k3 (n = 4) | 72 | 74 | 77 |
| F005a2 (L, n = 3) | 56 | 63 | 80 |
| F003l (L, n = 3) | 67 | 75 | 95 |
| F005b1 (n = 3) | 132 | 127 | 131 |
| F015a1 (n = 3) | 163 | 62 | 75 |
| F015a3 (L, n = 3) | 93 | 53 | 66 |
| F005d1 (n = 3) | 100 | 96 | 107 |
| F005c3 (L, n = 3) | 50 | 52 | 66 |

TABLE 34

Comparison of normalized PK parameters against Faslodex lot LW466

| Variant (Geometric Mean of n as indicated) | Cmax ratio to Faslodex (%) | AUC0-14d ratio to Faslodex (%) | AUC0-28d ratio to Faslodex (%) |
|---|---|---|---|
| Faslodex (LW466, n = 9) | 100 | 100 | 100 |
| Faslodex (MB122, n = 6) | 131 | 109 | 104 |
| Faslodex (MB948, n = 3) | 92 | 102 | 101 |
| Faslodex (MC949, n = 4) | 106 | 116 | 110 |
| Faslodex (All, n = 22) | 107 | 106 | 103 |
| B (n = 3) | 25 | 28 | 36 |
| E (n = 3) | 89 | 88 | 101 |
| I (n = 3) | 124 | 132 | 144 |
| J (n = 3) | 146 | 94 | 104 |
| K (n = 3) | 236 | 127 | 128 |
| L (n = 3) | 194 | 128 | 131 |
| L3F (n = 3) | 77 | 87 | 95 |
| L6 (n = 3) | 62 | 76 | 92 |
| F003a (n = 3) | 83 | 88 | 102 |
| F003b (n = 3) | 97 | 107 | 112 |
| F003e (n = 3) | 81 | 91 | 101 |
| F004a (n = 3) | 91 | 62 | 70 |
| F003k2 (n = 4) | 97 | 57 | 68 |
| F003k3 (n = 4) | 77 | 78 | 79 |
| F005a2 (L, n = 3) | 60 | 67 | 82 |
| F003l (L, n = 3) | 72 | 79 | 98 |
| F005b1 (n = 3) | 142 | 134 | 135 |
| F015a1 (n = 3) | 175 | 65 | 77 |
| F015a3 (L, n = 3) | 100 | 56 | 68 |
| F005d1 (n = 3) | 108 | 102 | 111 |
| F005c3 (L, n = 3) | 53 | 55 | 69 |

TABLE 35

Comparison of normalized PK parameters against Faslodex lot MB122

| Variant (Geometric Mean of n as indicated) | Cmax ratio to Faslodex (%) | AUC0-14d ratio to Faslodex (%) | AUC0-28d ratio to Faslodex (%) |
|---|---|---|---|
| Faslodex (LW466, n = 9) | 76 | 92 | 96 |
| Faslodex (MB122, n = 6) | 100 | 100 | 100 |
| Faslodex (MB948, n = 3) | 70 | 94 | 97 |
| Faslodex (MC949, n = 4) | 81 | 106 | 105 |
| Faslodex (All, n = 22) | 82 | 97 | 99 |
| B (n = 3) | 19 | 25 | 35 |
| E (n = 3) | 68 | 80 | 96 |
| I (n = 3) | 95 | 121 | 138 |
| J (n = 3) | 112 | 86 | 99 |
| K (n = 3) | 180 | 116 | 122 |
| L (n = 3) | 148 | 117 | 126 |
| L3F (n = 3) | 59 | 80 | 91 |
| L6 (n = 3) | 47 | 69 | 88 |
| F003a (n = 3) | 64 | 80 | 97 |
| F003b (n = 3) | 74 | 98 | 108 |
| F003e (n = 3) | 62 | 83 | 97 |
| F004a (n = 3) | 69 | 56 | 67 |
| F003k2 (n = 4) | 74 | 52 | 65 |
| F003k3 (n = 4) | 59 | 71 | 76 |
| F005a2 (L, n = 3) | 46 | 61 | 79 |
| F003l (L, n = 3) | 55 | 72 | 94 |
| F005b1 (n = 3) | 108 | 123 | 130 |
| F015a1 (n = 3) | 134 | 60 | 74 |
| F015a3 (L, n = 3) | 76 | 51 | 65 |
| F005d1 (n = 3) | 82 | 93 | 106 |
| F005c3 (L, n = 3) | 41 | 50 | 66 |

TABLE 36

Comparison of normalized PK parameters against Faslodex lot MB948

| Variant (Geometric Mean of n as indicated) | Cmax ratio to Faslodex (%) | AUC0-14d ratio to Faslodex (%) | AUC0-28d ratio to Faslodex (%) |
|---|---|---|---|
| Faslodex (LW466, n = 9) | 109 | 98 | 99 |
| Faslodex (MB122, n = 6) | 143 | 107 | 103 |
| Faslodex (MB948, n = 3) | 100 | 100 | 100 |
| Faslodex (MC949, n = 4) | 115 | 114 | 109 |
| Faslodex (All, n = 22) | 117 | 103 | 102 |
| B (n = 3) | 27 | 27 | 36 |
| E (n = 3) | 97 | 86 | 99 |
| I (n = 3) | 136 | 129 | 143 |
| J (n = 3) | 160 | 91 | 103 |
| K (n = 3) | 257 | 124 | 126 |
| L (n = 3) | 212 | 125 | 130 |
| L3F (n = 3) | 84 | 85 | 94 |
| L6 (n = 3) | 68 | 74 | 91 |
| F003a (n = 3) | 91 | 86 | 100 |
| F003b (n = 3) | 105 | 104 | 111 |
| F003e (n = 3) | 89 | 89 | 100 |
| F004a (n = 3) | 99 | 60 | 69 |
| F003k2 (n = 4) | 105 | 56 | 68 |
| F003k3 (n = 4) | 84 | 76 | 79 |
| F005a2 (L, n = 3) | 66 | 65 | 81 |
| F003l (L, n = 3) | 79 | 77 | 97 |
| F005b1 (n = 3) | 155 | 131 | 134 |
| F015a1 (n = 3) | 191 | 64 | 76 |
| F015a3 (L, n = 3) | 109 | 54 | 67 |

TABLE 36-continued

Comparison of normalized PK parameters against Faslodex lot MB948

| Variant (Geometric Mean of n as indicated) | Cmax ratio to Faslodex (%) | AUC0-14d ratio to Faslodex (%) | AUC0-28d ratio to Faslodex (%) |
|---|---|---|---|
| F005d1 (n = 3) | 118 | 100 | 109 |
| F005c3 (L, n = 3) | 58 | 54 | 68 |

TABLE 37

Comparison of normalized PK parameters against Faslodex lot MB949

| Variant (Geometric Mean of n as indicated) | Cmax ratio to Faslodex (%) | AUC0-14d ratio to Faslodex (%) | AUC0-28d ratio to Faslodex (%) |
|---|---|---|---|
| Faslodex (LW466, n = 9) | 95 | 86 | 91 |
| Faslodex (MB122, n = 6) | 124 | 94 | 95 |
| Faslodex (MB948, n = 3) | 87 | 88 | 92 |
| Faslodex (MC949, n = 4) | 100 | 100 | 100 |
| Faslodex (All, n = 22) | 102 | 91 | 94 |
| B (n = 3) | 24 | 24 | 33 |
| E (n = 3) | 84 | 76 | 91 |
| I (n = 3) | 118 | 113 | 131 |
| J (n = 3) | 139 | 81 | 94 |
| K (n = 3) | 223 | 109 | 116 |
| L (n = 3) | 184 | 110 | 119 |
| L3F (n = 3) | 73 | 75 | 87 |
| L6 (n = 3) | 59 | 65 | 84 |
| F003a (n = 3) | 79 | 76 | 92 |
| F003b (n = 3) | 91 | 92 | 102 |
| F003e (n = 3) | 77 | 78 | 92 |
| F004a (n = 3) | 86 | 53 | 63 |
| F003k2 (n = 4) | 91 | 49 | 62 |
| F003k3 (n = 4) | 73 | 67 | 72 |
| F005a2 (L, n = 3) | 57 | 58 | 75 |
| F003l (L, n = 3) | 69 | 68 | 89 |
| F005b1 (n = 3) | 134 | 115 | 123 |
| F015a1 (n = 3) | 166 | 56 | 70 |
| F015a3 (L, n = 3) | 94 | 48 | 62 |
| F005d1 (n = 3) | 102 | 88 | 100 |
| F005c3 (L, n = 3) | 50 | 47 | 62 |

Example: Pharmacokinetic Study 2 of Intramuscular Administration to Female Dogs

Fulvestrant pharmaceutical compositions L3F and L6 were prepared as described elsewhere herein and in the Figures. A preclinical study was performed to determine the pharmacokinetics of the pharmaceutical compositions following a single intramuscular administration of 15.4 mg/kg to female dogs. The pharmacokinetics of 15.4 mg/kg IM FASLODEX™ (fulvestrant injection, 250 mg/5 mL) were also determined and used for comparison to the three prototype pharmaceutical compositions. The 15.4 mg/kg dose used in this study is the canine equivalent, in mg/m², of the maximum dose (500 mg) for human use and was scaled for use in canine by dividing the dose (based on a 60 kg human) by a canine species conversion factor of 0.54.

Nine non-naïve female beagle dogs were used in the study. The animals weighed between approximately 5-13 kg. Animal welfare for this study was in compliance with the U.S. Department of Agriculture's (USDA) Animal Welfare Act (9 Code of Federal Regulations (CFR) Parts 1, 2 and 3). The Guide for the Care and Use of Laboratory Animals, Institute of Laboratory Animal Resources, National Academy Press, Washington, D.C., was followed. The facility maintained an Animal Welfare Assurance statement with the National Institutes of Health, Office of Laboratory Animal Welfare.

The FASLODEX™ test articles contained a small molecule that was used as received and no adjustment was made for purity, salt correction, etc. The FASLODEX™ test articles were gently agitated prior to dispensing and dose delivery. Pharmaceutical Compositions L3F and L6 were stored at room temperature and protected from light prior to use, and gently agitated prior to dispensing and dose delivery.

TABLE 38

| Dose Group | Test Article | Dosage (mg/kg) | Fulvestrant Conc. (mg/mL) | Dose Volume (mL/kg) |
|---|---|---|---|---|
| 1 | FASLODEX ™ | 15.4 | 50 | 0.308 |
| 2 | Pharmaceutical Composition L3F | 15.4 | 100 | 0.154 |
| 3 | Pharmaceutical Composition L6 | 15.4 | 100 | 0.154 |

The animals were not fasted prior to dosing. Each animal received a single intramuscular (IM) dose of only one of the appropriate test article pharmaceutical compositions as outlined in the following study design table, Table 38. IM doses were administered with a 20 G needle via bolus injection into the same large muscle mass (using the Z-track injection technique) in the left hind limb of each animal. Attempts were made for consistent injections between animals [selection of the dose site (muscle), depth, etc.]. The hair was clipped from the injection site prior to dosing. The injection site was marked following dosing and remarked as necessary throughout the study. Specifications for all dose delivery were recorded and reported in the study report [including, but not limited to needle gauge/length, syringe size/barrel type with manufacturer and part number, estimated injection depth into the muscle, approximate duration required to administer the injection; any substantial resistance (either flow through the syringe/needle and/or into the muscle during administration)] was documented.

All animals were observed at least twice a day for morbidity, mortality, injury, and availability of food and water. Any animals in poor health were identified for further monitoring and possible euthanasia.

Whole venous blood samples of approximately 2 mL each were collected from a peripheral vein of all animals for determination of fulvestrant exposure. Samples were collected at the following target timepoints; predose, 0.25, 0.5, 1, 2, 4, 8, 12, 24 (Day 2), 48 (Day 3), 72 (Day 4), 96 (Day 5), 120 (Day 6), 192 (Day 9), 264 (Day 12), 336 (Day 15), 384 (Day 17), 528 (Day 23), and 672 (Day 29) hours after administration. Blood was collected with sodium heparin anticoagulant (glass tube, no gel separator). All blood samples were placed on wet ice following collection until centrifuged. Blood was centrifuged at 3500 rpm for 7 minutes at 2 to 8° C. Plasma (minimum of 0.8 mL volume) was separated from blood cells within 0.75 hours of blood collection and frozen. Plasma samples were initially placed on dry ice prior to being stored in the appropriate freezer (−60 to −90° C.). Samples were shipped on dry ice for bioanalytical analysis.

Figure 2A:
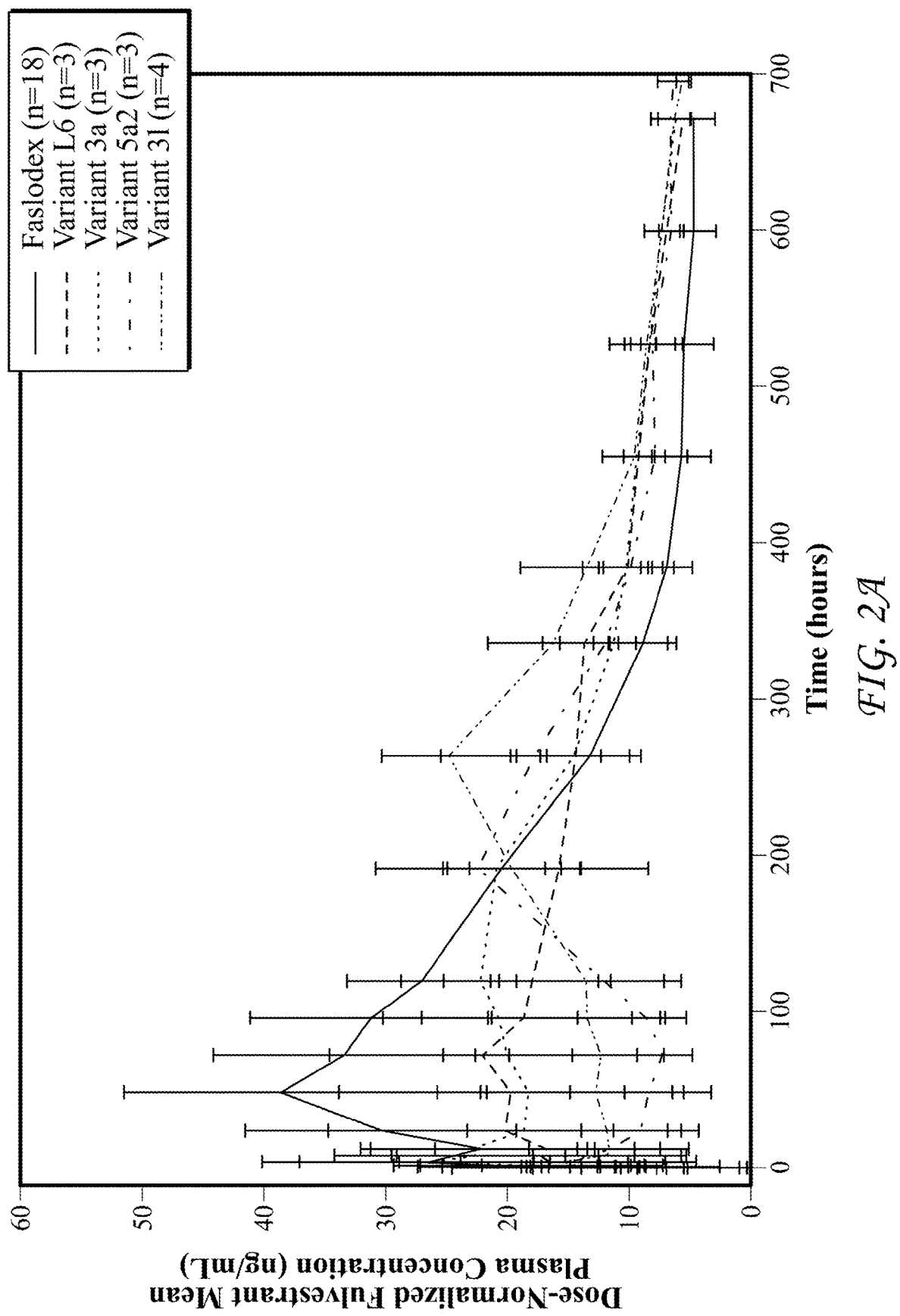
FIG. 2A depicts pharmacokinetic data for administration of commercial fulvestrant formulations (FASLODEX™) and some exemplary fulvestrant formulations of the present disclosure to canines.
Figure 2B:
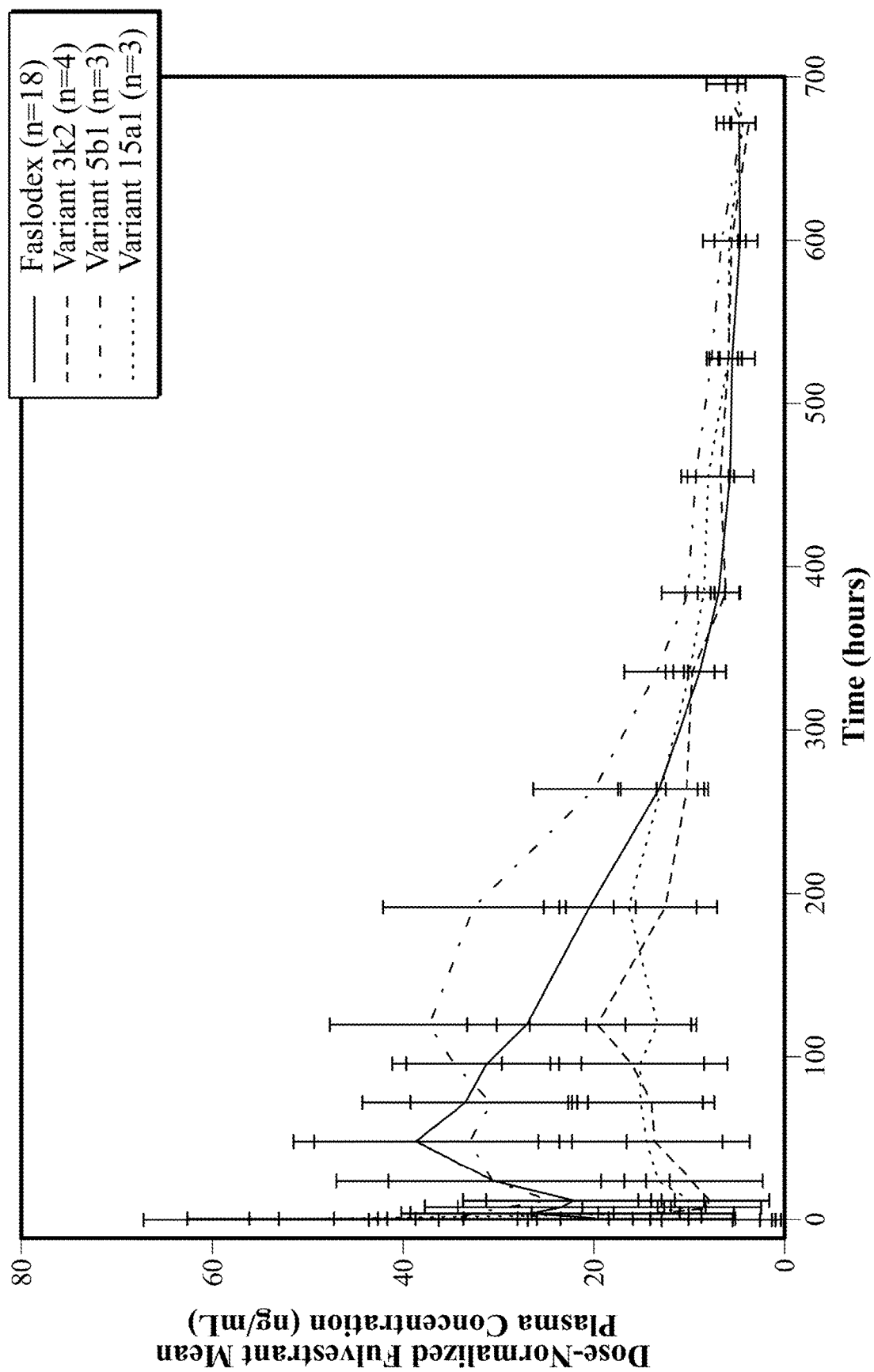
FIG. 2B depicts pharmacokinetic data for administration of commercial fulvestrant formulations (FASLODEX™) and some exemplary fulvestrant formulations of the present disclosure to canines.
Figure 2C:
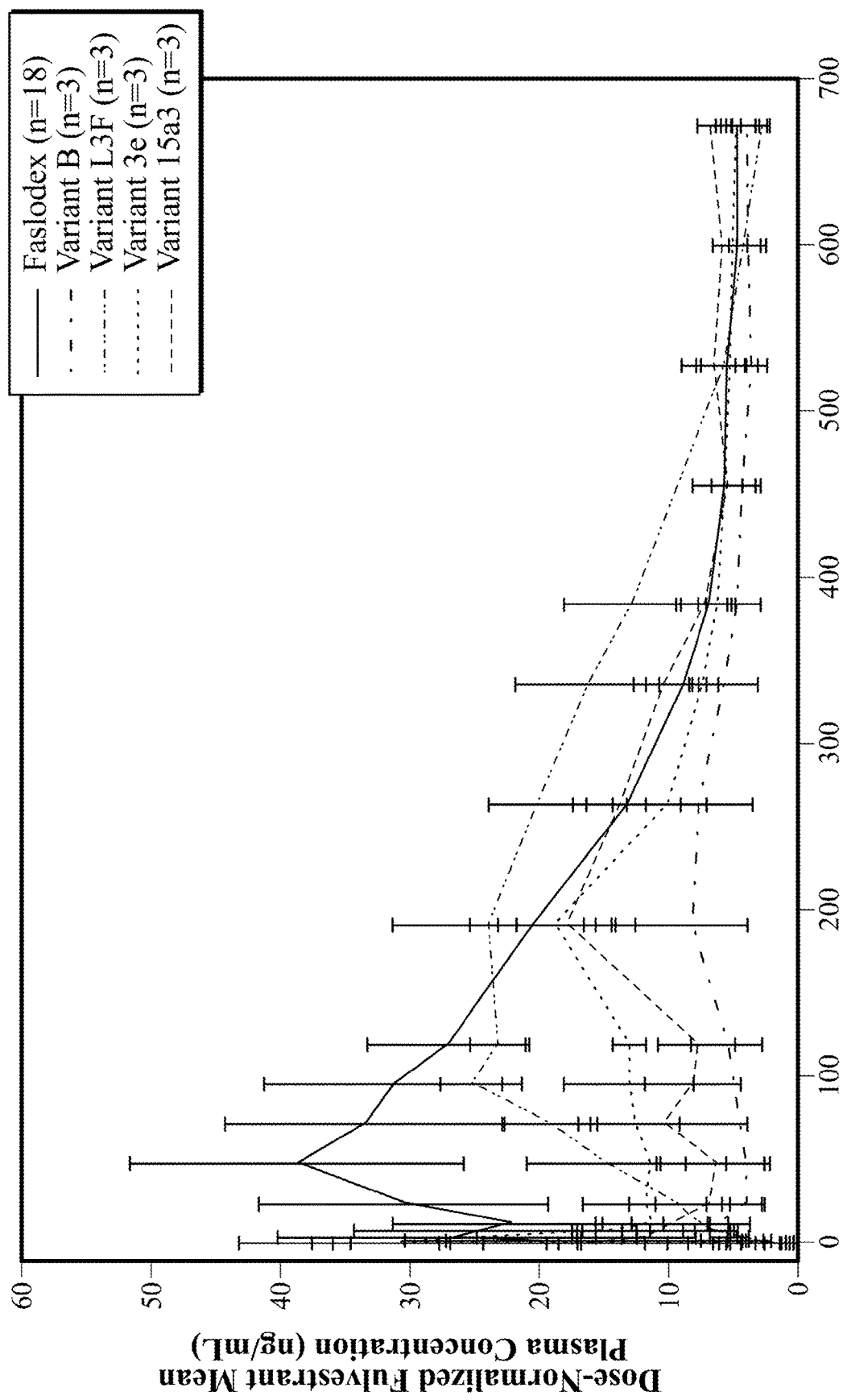
FIG. 2C depicts pharmacokinetic data for administration of commercial fulvestrant formulations (FASLODEX™) and some exemplary fulvestrant formulations of the present disclosure to canines.
Figure 3:
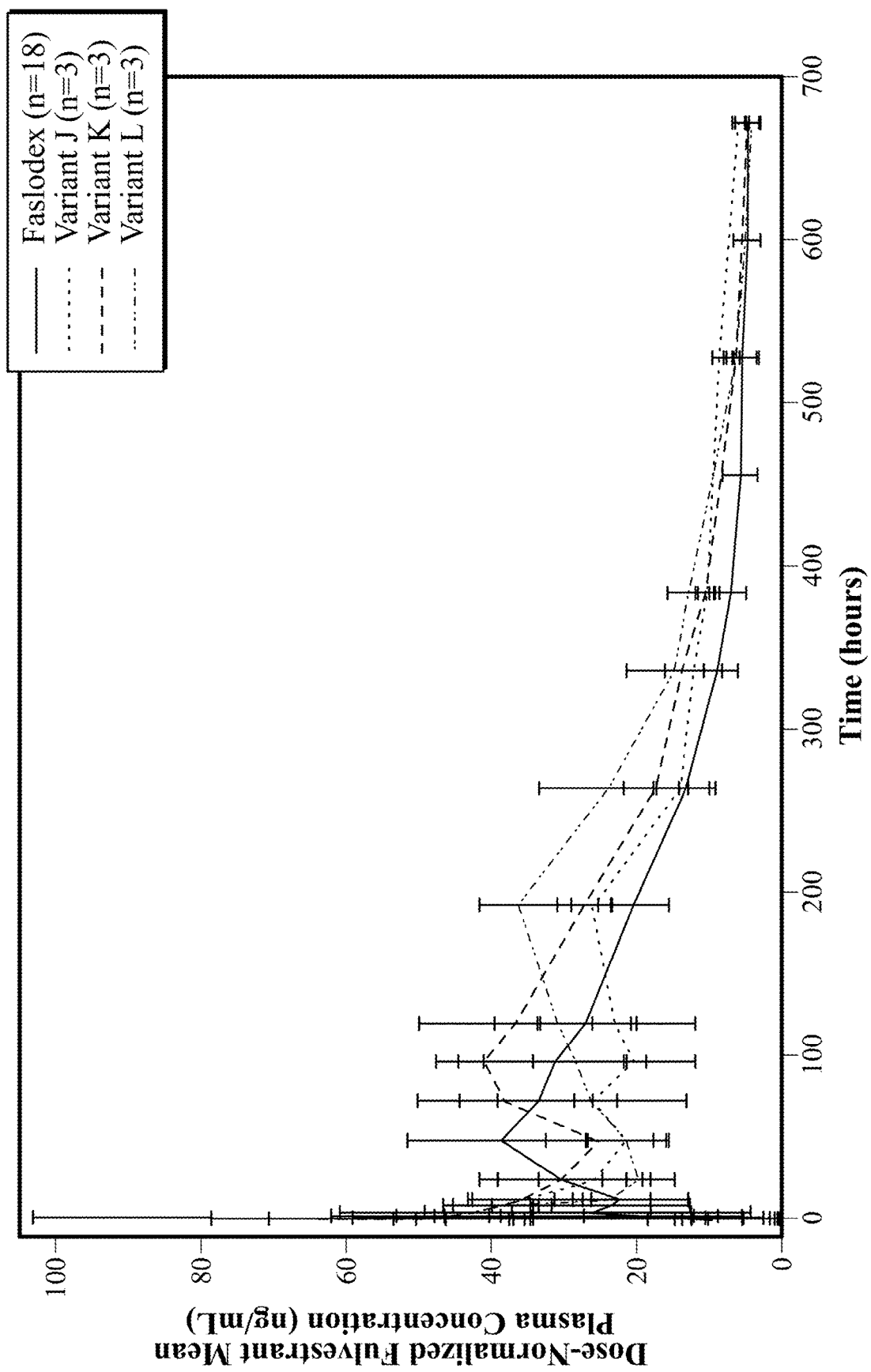
FIG. 3 depicts pharmacokinetic data for administration of commercial fulvestrant formulations (FASLODEX™) and some exemplary fulvestrant formulations of the present disclosure to canines.
Figure 7:
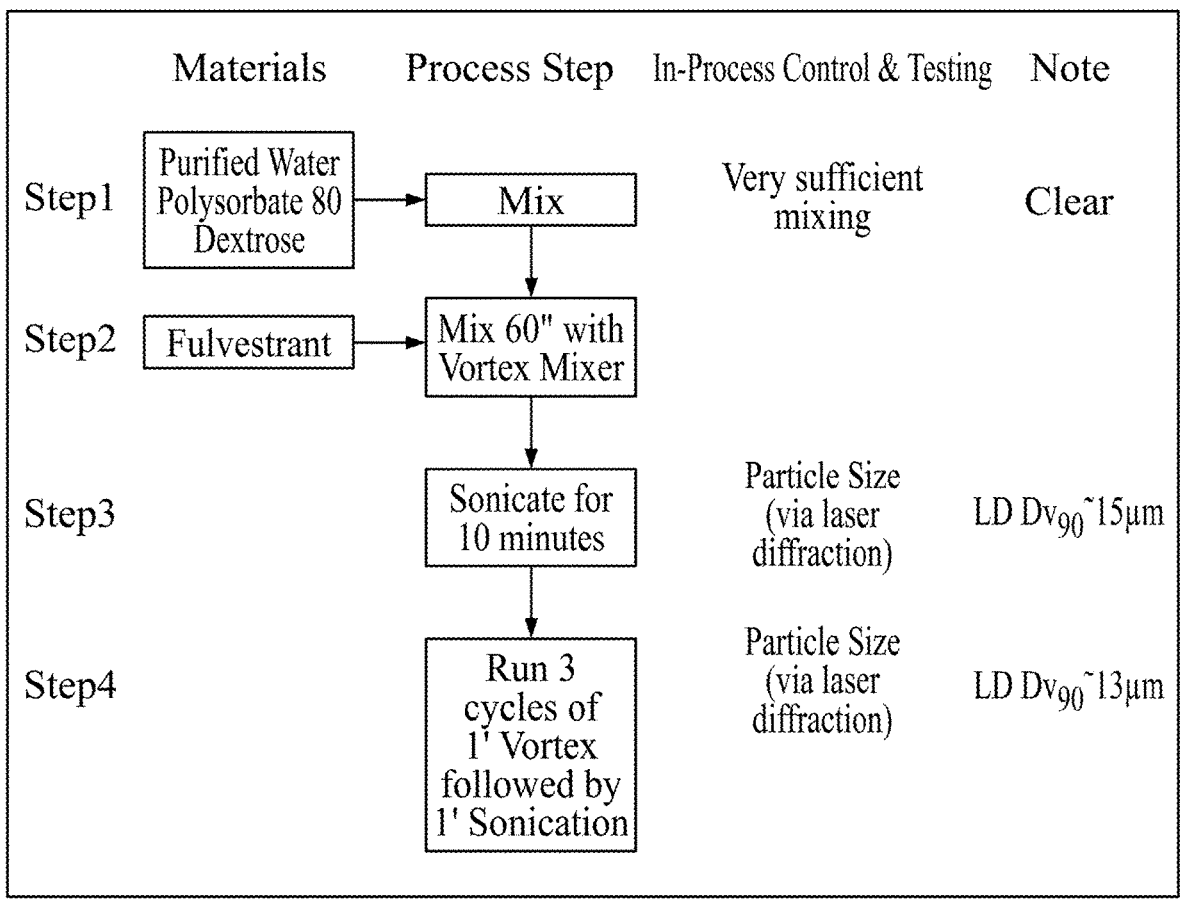
FIG. 7 depicts aspects of exemplary methods of preparation for fulvestrant suspensions of the present disclosure.
Figure 9:
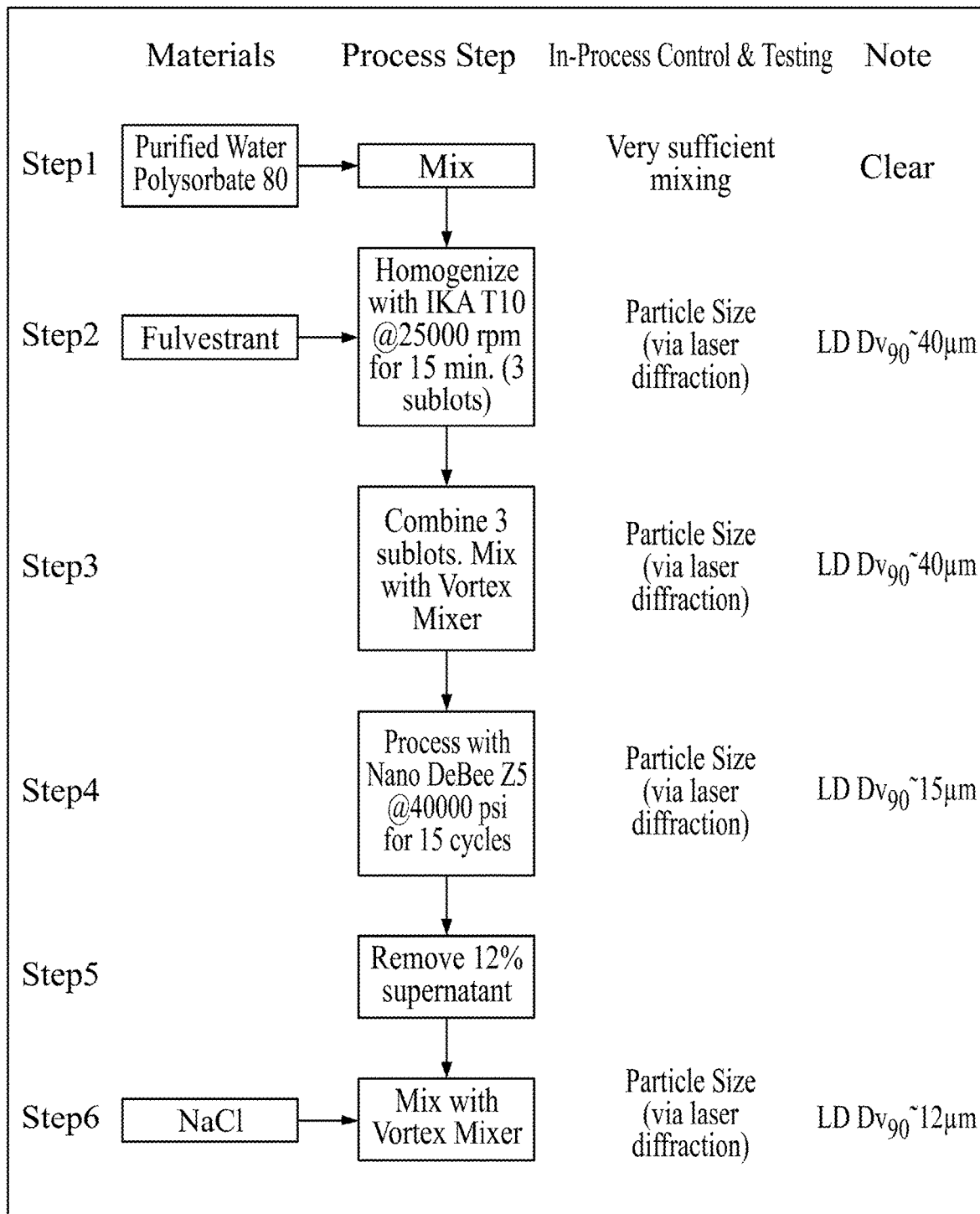
FIG. 9 depicts aspects of exemplary methods of preparation for fulvestrant suspensions of the present disclosure.

A model independent method was used to determine $C_{max}$ and AUC values from fulvestrant plasma concentration-time data. Results are shown in Tables 31-37 and FIGS. 2A and 2C. Table 31 shows the pharmacokinetic data from the 15.4 mg/kg dosages as nominally dosed (based on the target fulvestrant concentration for each pharmaceutical composition). An "Assay %" is shown for the fulvestrant pharmaceutical compositions of the present disclosure used in the study. The "Assay %" represents the percentage equivalence of the particular pharmaceutical composition in comparison to the FASLODEX™ label claim fulvestrant concentration, with "Assay %" values determined via HPLC, measurement samples taken pre- and post-dose, with one value selected for normalization. The data in Tables 32-37 are normalized using the "Assay %" values to compare PK results based upon the actual mg/kg of fulvestrant administered, assuming linear scaling. FIGS. 2A and 2C depict graphs of the dose normalized fulvestrant mean plasma concentrations.

Example: Pharmacokinetic Study 3 of Intramuscular and Intravenous Administration to Female Dogs Fulvestrant formulations F003a, F003b, F004a, F003e, F003k2, F003k3, F005a2, F003l, F005b1, F015a1, F005d1, F005c3, F015a3, F005g5, Del-1S, Del-2S, F005H3, Lot 15, Lot 26, Lot 27, Lot 28, Lot 42, Lot 43, Lot 45, Lot 46, Lot 47, and Lot 48 were prepared as described elsewhere herein and in the Figures. In some instances, the formulations were prepared using different processes as indicated, referred to by an alphanumeric process identifier, such as "Process A1," "Process A2," and the like. A fulvestrant pharmaceutical composition for intravenous injection, referred to as batch FV-004/15M, was prepared as described below. A preclinical study was performed to determine the pharmacokinetics of the pharmaceutical compositions following a single intramuscular (IM) administration of 15.4 mg/kg to female dogs. The pharmacokinetics of 15.4 mg/kg IM FASLODEX™ (fulvestrant injection, 250 mg/5 mL) were also determined and used for comparison to the three prototype pharmaceutical compositions. The 15.4 mg/kg dose used in this study is the canine equivalent, in mg/m², of the maximum dose (500 mg) for human use and was scaled for use in canine by dividing the dose (based on a 60 kg human) by a canine species conversion factor of 0.54.

One hundred fifty-six non-naïve female beagle dogs of body weight range of 5.65 to 11.40 kilograms were used in the study and assigned to Groups 1-48, as shown in Table 39 below.

Animal welfare for this study was in compliance with the U.S. Department of Agriculture's (USDA) Animal Welfare Act (9 Code of Federal Regulations (CFR) Parts 1, 2 and 3). The Guide for the Care and Use of Laboratory Animals, Institute of Laboratory Animal Resources, National Academy Press, Washington, D.C., was followed. The facility maintained an Animal Welfare Assurance statement with the National Institutes of Health, Office of Laboratory Animal Welfare.

TABLE 39

| Group Number | Test Article | Number of Females | Dose Route | Fulvestrant Concentration (mg/mL) | Dose Level (mg/kg) | Dose Volume (mL/kg) |
| --- | --- | --- | --- | --- | --- | --- |
| 1 | Faslodex (lot LW466) | 3 | IM | 50 | 15.4 | 0.308 |
| 2 | Faslodex (lot MB122) | 3 | IM | 50 | 15.4 | 0.308 |
| 3 | Faslodex (lot MB948) | 3 | IM | 50 | 15.4 | 0.308 |
| 4 | Formulation F003a | 3 | IM | 100 | 15.4 | 0.154 |
| 5 | Formulation F003b | 3 | IM | 100 | 15.4 | 0.154 |
| 6 | Formulation F004a | 3 | IM | 100 | 15.4 | 0.154 |
| 7 | Formulation F003e | 3 | IM | 100 | 15.4 | 0.154 |
| 8 | Formulation F003k2 | 4 | IM | 100 | 15.4 | 0.154 |
| 9 | Formulation F003k3 | 4 | IM | 100 | 15.4 | 0.154 |
| 10 | Faslodex (lot MC949) | 4 | IM | 50 | 15.4 | 0.308 |
| 11 | Formulation F005a2 | 3 | IM | 100 | 15.4 | 0.154 |
| 12 | Formulation F003l | 4 | IM | 100 | 15.4 | 0.154 |
| 13 | Formulation F005b1 | 3 | IM | 100 | 15.4 | 0.154 |
| 14 | Formulation F015a1 | 3 | IM | 100 | 15.4 | 0.154 |
| 15 | Formulation F005d1 | 3 | IM | 100 | 15.4 | 0.154 |
| 16 | Formulation F005c3 | 4 | IM | 100 | 15.4 | 0.154 |
| 17 | Formulation F015a3 | 3 | IM | 100 | 15.4 | 0.154 |
| 18 | Fulvestrant (batch FV-004/15 M) | 4 | IV | 20 | 2.5 | 0.125 |
| 19 | Formulation F005g5 | 4 | IM | 100 | 15.4 | 0.154 |
| 20 | Formulation Del-1S | 4 | IM | 100 | 15.4 | 0.154 |
| 21 | Formulation Del-2S | 4 | IM | 100 | 15.4 | 0.154 |
| 22 | Formulation F005H3 | 3 | IM | 100 | 15.4 | 0.154 |
| 23 | Lot 15, by Process E1 | 4 | IM | 100 | 15.4 | 0.154 |
| 24 | Lot 15, by Process E2 | 3 | IM | 100 | 15.4 | 0.154 |
| 25 | Lot 26, by Process F1 | 3 | IM | 100 | 15.4 | 0.154 |
| 26 | Lot 26, by Process F2 | 3 | IM | 100 | 15.4 | 0.154 |
| 27 | Lot 26, by Process F3 | 3 | IM | 100 | 15.4 | 0.154 |
| 28 | Lot 26, by Process F4 | 3 | IM | 100 | 15.4 | 0.154 |
| 29 | Lot 26, by Process J1 | 3 | IM | 100 | 15.4 | 0.154 |
| 30 | Lot 26, by Process J2 | 3 | IM | 100 | 15.4 | 0.154 |
| 31 | Lot 26, by Process J3 | 3 | IM | 100 | 15.4 | 0.154 |
| 32 | Lot 26, by Process J4 | 3 | IM | 100 | 15.4 | 0.154 |
| 33 | Lot 42, by Process G1 | 3 | IM | 100 | 15.4 | 0.154 |
| 34 | Lot 42, by Process G2 | 3 | IM | 100 | 15.4 | 0.154 |
| 35 | Lot 43, by Process H1 | 3 | IM | 100 | 15.4 | 0.154 |
| 36 | Lot 43, by Process H2 | 3 | IM | 100 | 15.4 | 0.154 |
| 37 | Lot 27, by Process A1 | 3 | IM | 100 | 15.4 | 0.154 |
| 38 | Lot 27, by Process A2 | 3 | IM | 100 | 15.4 | 0.154 |

TABLE 39-continued

| Group Number | Test Article | Number of Females | Dose Route | Fulvestrant Concentration (mg/mL) | Dose Level (mg/kg) | Dose Volume (mL/kg) |
|---|---|---|---|---|---|---|
| 39 | Lot 27, by Process A3 | 3 | IM | 100 | 15.4 | 0.154 |
| 40 | Lot 27, by Process A4 | 3 | IM | 100 | 15.4 | 0.154 |
| 41 | Lot 28, by Process B1 | 3 | IM | 100 | 15.4 | 0.154 |
| 42 | Lot 28, by Process B2 | 3 | IM | 100 | 15.4 | 0.154 |
| 43 | Lot 28, by Process B3 | 3 | IM | 100 | 15.4 | 0.154 |
| 44 | Lot 28, by Process B4 | 3 | IM | 100 | 15.4 | 0.154 |
| 45 | Lot 45, by Process C1 | 3 | IM | 100 | 15.4 | 0.154 |
| 46 | Lot 46 | 3 | IM | 100 | 15.4 | 0.154 |
| 47 | Lot 47 | 3 | IM | 100 | 15.4 | 0.154 |
| 48 | Lot 48 | 3 | IM | 100 | 15.4 | 0.154 |

Pharmaceutical Compositions F003a, F003b, F004a, F003e, F003k2, F003k3, F005a2, F003l, F005b1, F015a1, F005d1, F005c3, F015a3, FV-004/15M, Del-1S, and Del-2S were stored at room temperature and protected from light prior to use, and gently agitated via inversion prior to dispensing and dose delivery. If visible clumps of material were seen on the vial inside wall or inner seal of the vial cap after 3 minutes of inversion, the tightly capped vial was vortexed at moderate intensity and unlimited duration until clumps were not visible. FASLODEX™ was supplied as two 5-mL clear neutral glass (Type 1) syringe barrels, each containing a 250 mg/5 mL (50 mg/mL) solution for intramuscular injection. Upon receipt, FASLODEX™ was stored refrigerated (2°–8° C.) and protected from light. The procedure to prepare and administer FASLODEX™ was performed as outlined in the manufacturer's prescribing information.

Lyophilized pharmaceutical compositions of formulations F005g5, F005H3, F015a3, Lot 15, Lot 26, Lot 27, Lot 28, Lot 42, Lot 43, Lot 45, Lot 46, Lot 47, and Lot 48 were reconstituted prior to dosing. Using an empty syringe and hypodermic needle, about 5 mL of air was withdrawn from the head space of the vial (above the lyophilized contents) via the septum and the syringe and needle were discarded. Using a sterile syringe and hypodermic needle, 5 mL of sterile water for injection, USP were added to the vial by piercing the septum and injecting a stream of water slowly around the inner wall of the neck of the vial to wet the lyophilized cake without touching any of the vial contents. The needle was removed from the septum and the vial was gently swirled until a visually homogeneous particulate suspension formed, with no visual clumps or material attached to the inside wall of the vial. If a homogeneous suspension was not formed after 5 minutes of swirling, the vial was vortexed until a homogeneous suspension was formed. The vials were not shaken to avoid generating bubbles or excessive foam.

Group 18 was administered an intravenous batch of fulvestrant (batch FV-004/15M) prepared as follows by (% w/v): 2% fulvestrant, 10% EtOH, 79% propylene glycol, 1% Poloxamer 407, 8% Water for Injection, USP. Fulvestrant API was stored at 2-8° C., protected from light. Care was taken to protect the API from humidity during weighing. Fulvestrant powder was dissolved in ethanol and swirled and vortexed as needed to dissolve completely. Propylene glycol was added and mixed to dissolve to a clear liquid state. Poloxamer 407 was dissolved in water for injection, USP in a separate vessel and mixed, vortexed, and sonicated as needed to dissolve into to a clear liquid state. The Poloxamer 407 in water for injection solution was added to the fulvestrant/ethanol solution. Propylene glycol was added and the solution was mixed and vortexed to achieve a clear liquid. The solution was filtered through a 0.2 μm or 0.22 μm syringe (to ensure that all liquid volume was usable) tip filter (PVDF) into a clear glass vessel. The prepared formulation as stored at room temperature for up to four hours prior to dosing under protection from light exposure. Intravenous doses were administered via the cephalic (or other suitable) vein as a slow injection over approximately 1 minute. Batch FV-004/15M was administered intravenously at a dose of 2.5 mg/kg.

The animals were not fasted prior to dosing. Each animal in Groups 4-9, 11-17, and 19-48 received a single intramuscular (IM) dose of only one of the appropriate test article pharmaceutical compositions as outlined in Table 39. IM doses were administered with a 20 G needle via bolus injection into the same large muscle mass (using the Z-track injection technique) in the left hind limb of each animal. Attempts were made for consistent injections between animals [selection of the dose site (muscle), depth, etc.]. The hair was clipped from the injection site prior to dosing. The injection site was marked following dosing and remarked as necessary throughout the study. Specifications for all dose delivery were recorded and reported in the study report [including, but not limited to needle gauge/length, syringe size/barrel type with manufacturer and part number, estimated injection depth into the muscle, approximate duration required to administer the injection; any substantial resistance (either flow through the syringe/needle and/or into the muscle during administration)] was documented. Animals in Groups 13-17 and 19-48 were administered 1 tablet or capsule (25 mg) of (PO) diphenhydramine at approximately 1 hour prior to dosing.

All animals were observed at least twice a day for morbidity, mortality, injury, and availability of food and water. Any animals in poor health were identified for further monitoring and possible euthanasia.

Whole venous blood samples of approximately 2 mL each were collected from a peripheral vein of all animals for determination of fulvestrant exposure. Blood samples for Groups 1-7 were collected predose and at 0.25, 0.5, 1, 2, 4, 8, and 12 (on Day 1); and 24 (on Day 2), 48 (on Day 3), 72 (on Day 4), 96 (on Day 5), 120 (on Day 6), 192 (on Day 9), 264 (on Day 12), 336 (on Day 15), 384 (on Day 17), 528 (on Day 23), and 672 (on Day 29) hours postdose. Blood samples for Groups 8-14 were collected predose and at 0.25, 0.5, 1, 2, 4, 8, and 12 (on Day 1); and 24 (on Day 2), 48 (on Day 3), 72 (on Day 4), 96 (on Day 5), 120 (on Day 6), 192 (on Day 9), 264 (on Day 12), 336 (on Day 15), 384 (on Day 17), 456 (on Day 20), 528 (on Day 23), 600 (on Day 26), 672 (on Day 29), 696 (Day 30), 768 (Day 33), 816 (Day 35), 864 (Day 37), 936 (Day 40) and 1008 (Day 43) hours post-dose.

Blood samples for Groups 15-17 and 19-21 were collected predose and at 0.25, 0.5, 1, 2, 4, 8, 12 (Day 1), 24 (Day 2), 48 (Day 3), 72 (Day 4), 96 (Day 5), 120 (Day 6), 192 (Day 9), 264 (Day 12), 336 (Day 15), 384 (Day 17), 456 (Day 20), 528 (Day 23), 600 (Day 26), 672 (Day 29), 696 (Day 30), 768 (Day 33), 816 (Day 35), 864 (Day 37), 936 (Day 40), 1008 (Day 43), and 1176 (Day 50) hours postdose. Blood samples for Group 18 were collected predose and at 0.033 (2 minutes), 0.1 (6 minutes), 0.13 (8 minutes), 0.27 (16 minutes), 0.52 (31 minutes), 0.77 (46 minutes), 1, 2, 3, 4, 6, 8, 10, and 12 hours postdose on Day 1 and at 24 (on Day 2), 30 (on Day 2), 48 (on Day 3) and 72 (on Day 4) hours postdose, with postdose measurements from the start of dose administration, which took about 1 minute to complete. Blood samples for Groups 22-48 were collected predose and at 0.25, 0.5, 1, 2, 4, 8, 12 (Day 1), 24 (Day 2), 48 (Day 3), 72 (Day 4), 96 (Day 5), 120 (Day 6), 144 (Day 7), 168 (Day 8), 192 (Day 9), 216 (Day 10), 240 (Day 11), 264 (Day 12), 336 (Day 15), 384 (Day 17), 456 (Day 20), 528 (Day 23), 600 (Day 26), 672 (Day 29), 696 (Day 30), 768 (Day 33), 816 (Day 35), 864 (Day 37), 936 (Day 40), 1008 (Day 43), and 1176 (Day 50) hours postdose. Blood was collected with sodium heparin anticoagulant (glass tube, no gel separator). All blood samples were placed on wet ice following collection until centrifuged. Blood was centrifuged at 3500 rpm for 7 minutes at 2 to 8° C. Plasma (minimum of 0.8 mL volume) was separated from blood cells within 0.75 hours of blood collection and frozen. Plasma samples were initially placed on dry ice prior to being stored in the appropriate freezer (−60 to −90° C.). Samples were shipped on dry ice for bioanalytical analysis to determine absolute ng/mL fulvestrant in the plasma.

Figure 13:
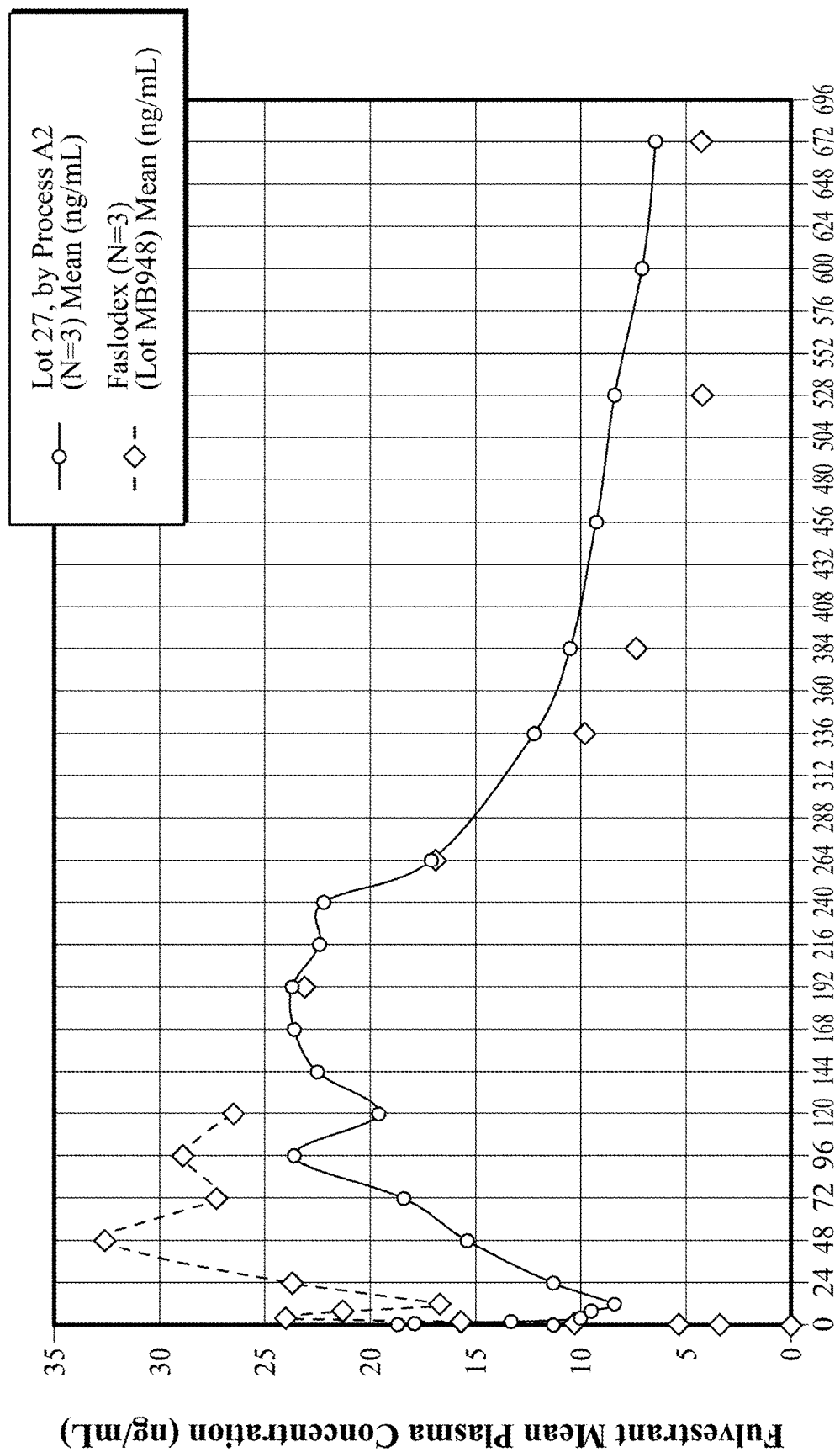
FIG. 13 depicts pharmacokinetic data for administration of commercial fulvestrant formulations (FASLODEX™) and some exemplary fulvestrant formulations of the present disclosure to canines.
Figure 14:
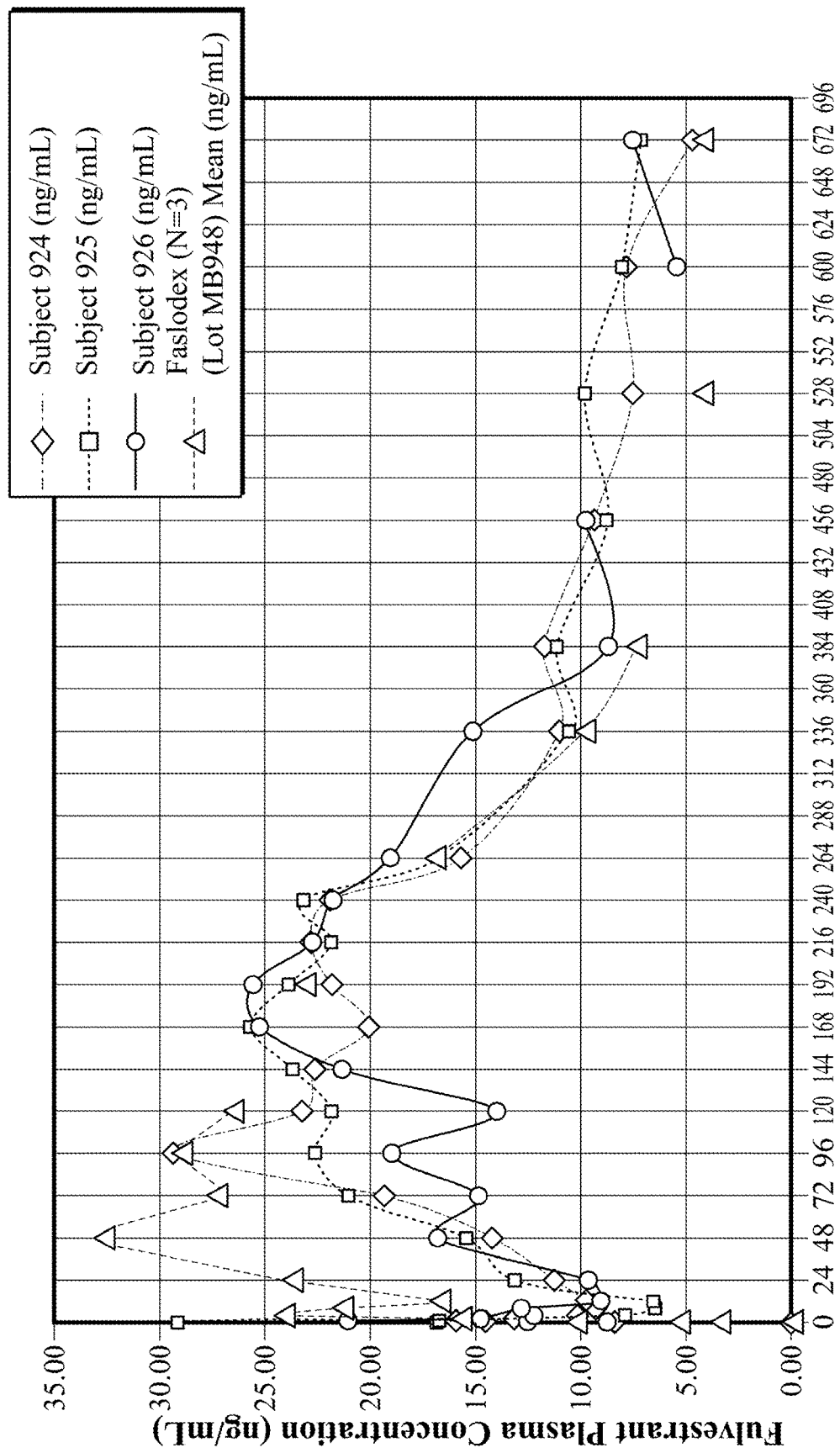
FIG. 14 depicts pharmacokinetic data for administration of commercial fulvestrant formulations (FASLODEX™) and some exemplary fulvestrant formulations of the present disclosure to canines.

A model independent method was used to determine $C_{max}$ and AUC values from fulvestrant plasma concentration-time data. Results are shown in Tables 31-37 and 40 and FIGS. 1A, 1B, 2A, 2B, 2C, 13, and 14. Table 31 shows the pharmacokinetic data from the 15.4 mg/kg dosages as nominally dosed (based on the target fulvestrant concentration for each pharmaceutical composition). An "Assay %" is shown in Table 31 for the fulvestrant pharmaceutical compositions of the present disclosure used in the study. The "Assay %" represents the percentage equivalence of the particular pharmaceutical composition in comparison to the FASLODEX™ label claim fulvestrant concentration, with "Assay %" values determined via HPLC, measurement samples taken pre- and post-dose, with one value selected for normalization. The data in Tables 32-37 are normalized using the "Assay %" values to compare PK results based upon the actual mg/kg of fulvestrant administered, assuming linear scaling. FIGS. 1A, 1B, 2A, 2B, and 2C depict graphs of the dose normalized fulvestrant mean plasma concentrations. Table 40 shows the pharmacokinetic data from the 15.4 mg/kg dosages as nominally dosed (based on the target fulvestrant concentration for each pharmaceutical composition) in comparison to the geometric mean of all Faslodex lots tested (n=22). FIGS. 13 and 14 depict fulvestrant plasma measurements for administration of Faslodex Lot MB948 to three female dogs and administration of fulvestrant formulation Lot 27 processed by Process A2 to three female dogs (referred to in FIG. 14 as subjects 924, 925, and 926).

Example: Microscopic Imaging of Fulvestrant Particles in Suspensions

Some exemplary fulvestrant pharmaceutical compositions of the present disclosure were examined via optical and

TABLE 40

| Formulation (Geometric Mean, n = 3 unless indicated otherwise) | PK parameters compared to nominal dose 15.4 mg/kg | | | PK parameters based upon the Faslodex lots based upon the nominal dose 15.4 mg/kg | | |
|---|---|---|---|---|---|---|
| | Cmax (ng/mL) | $AUC_{0-14\,d}$ (hr*ng/mL) | $AUC_{0-28\,d}$ (hr*ng/mL) | Cmax ratio to Faslodex (%) | $AUC_{0-14\,d}$ ratio to Faslodex (%) | $AUC_{0-28\,d}$ ratio to Faslodex (%) |
| Faslodex (All, n = 22) | 37.5 | 7408 | 9195 | 100 | 100 | 100 |
| F005g5 | 32.1 | 6950 | 10400 | 86 | 94 | 113 |
| Lot 15, by Process E1 | 20.1 | 3890 | 5500 | 54 | 53 | 60 |
| Lot 15, by Process E2 | 20.3 | 4190 | 6230 | 54 | 57 | 68 |
| Lot 26, by Process F1 | 19.5 | 4150 | 6650 | 52 | 56 | 72 |
| Lot 26, by Process F2 | 30.5 | 5510 | 7850 | 81 | 74 | 85 |
| Lot 26, by Process F3 | 25.7 | 5350 | 8260 | 68 | 72 | 90 |
| Lot 26, by Process F4 | 30.8 | 7210 | 10200 | 82 | 97 | 111 |
| Lot 26, by Process J1 | 25.2 | 5490 | 7910 | 67 | 74 | 86 |
| Lot 26, by Process J2 | 20.8 | 4640 | 7190 | 55 | 63 | 78 |
| Lot 26, by Process J3 | 21.1 | 4720 | 7310 | 56 | 64 | 80 |
| Lot 26, by Process J4 | 21.3 | 4320 | 5900 | 57 | 58 | 64 |
| Lot 42, by Process G1 | 28.1 | 4640 | 7410 | 75 | 63 | 81 |
| Lot 42, by Process G2 | 33.8 | 6110 | 8800 | 90 | 82 | 96 |
| Lot 43, by Process H1 | 25.0 | 5190 | 7500 | 67 | 70 | 82 |
| Lot 43, by Process H2 | 22.2 | 4430 | 6250 | 59 | 60 | 68 |
| Lot 27, by Process A1 | 92.6 | 6150 | 8710 | 247 | 83 | 95 |
| Lot 27, by Process A2 | 27.9 | 6240 | 9170 | 74 | 84 | 100 |
| Lot 27, by Process A3 | 26.3 | 5100 | 7680 | 70 | 69 | 84 |
| Lot 27, by Process A4 | 29.1 | 6030 | 8620 | 78 | 81 | 94 |
| Lot 28, by Process B1 | 21.9 | 3950 | 6230 | 58 | 53 | 68 |
| Lot 28, by Process B2 | 36.3 | 7010 | 9870 | 97 | 95 | 107 |
| Lot 28, by Process B3 | 31.6 | 6880 | 9660 | 84 | 93 | 105 |
| Lot 28, by Process B4 | 31.0 | 6330 | 9000 | 83 | 85 | 98 |
| Lot 45, by Process C1 | 29.8 | 5320 | 8560 | 79 | 72 | 93 |
| Lot 46 | 30.2 | 5570 | 8240 | 80 | 75 | 90 |
| Lot 47 | 27.9 | 5230 | 8070 | 74 | 71 | 88 |
| Lot 48 | 26.3 | 4900 | 7410 | 70 | 66 | 81 | scanning electron microscopy. Suspensions of fulvestrant pharmaceutical compositions Variants B, E, I, J, K, L, L3F, L6, F003a, F003b, F004a, F003e, F00k2, and F003k3 were examined via optical microscopy. Optical microscopy was performed at 400× magnification with a polarized light filter using fully dispersed homogeneous suspension samples.

Example: Particle Size Distribution Characterization of Fulvestrant Pharmaceutical Compositions Batches of fulvestrant pharmaceutical composition Lot 27, described elsewhere herein, were prepared by the methods of preparation 101 of FIG. 15. Samples were taken periodically during high shear mixing, prior to any high pressure homogenization steps. Some test samples, referred to as "Sample 1", were taken after approximately five hours of high shear mixing and other test samples, referred to as "Sample 2", were taken after approximately 13.7 hours to high shear mixing. Particle sizes of test samples were analyzed using optical microscopy with a Malvern Morphologi G3 apparatus for microscopy image capture and analysis. CE diameters were measured and number-weighted and volume-weighted particle size distribution parameters were determined as shown in Tables 41 and 42. The CE diameter ranges of measurement aliquots are also shown, with the lower range value of 0.54 microns representing the lower limit of detection for the apparatus setup. Test samples were analyzed with a Malvern Mastersizer 3000 apparatus for laser diffraction particle size characterization of LD diameters.

TABLE 41

Volume-Weighted Distribution Parameters

| Formulation | CE Dv (10) (µm) | CE Dv (50) (µm) | CE Dv (90) (µm) | Circle Equivalent (CE)-diameter-range (µm) | LD Dv10 (µm) | LD Dv50 (µm) | LD Dv90 (µm) |
|---|---|---|---|---|---|---|---|
| Lot 27 (Sample 1) | 6.113 | 13.77 | 32.71 | 0.54-49.72 | 1.81 | 6.68 | 16.6 |
| Lot 27 (Sample 1) | 6.509 | 14.34 | 28.64 | 0.54-54.14 | 1.85 | 6.93 | 17.7 |
| Lot 27 (Sample 1) | 6.378 | 12.76 | 23.90 | 0.54-55.04 | | | |
| Lot 27 (Sample 1) | 5.297 | 10.73 | 24.57 | | | | |
| Lot 27 (Sample 1) | 6.015 | 13.03 | 25.25 | | | | |
| Lot 27 (Sample 1) | 5.446 | 11.41 | 22.10 | | | | |
| Lot 27 (Sample 1) | 7.222 | 14.93 | 28.99 | | | | |
| Lot 27 (Sample 1) | 8.747 | 18.31 | 32.93 | | | | |
| Lot 27 (Sample 1) | 7.663 | 14.96 | 26.58 | | | | |
| Lot 27 (Sample 2) | 6.733 | 13.61 | 24.70 | 0.54-42.64 | 1.96 | 7.54 | 19.3 |
| Lot 27 (Sample 2) | 7.182 | 14.12 | 25.15 | 0.54-44.65 | | | |
| Lot 27 (Sample 2) | 6.920 | 13.26 | 22.63 | 0.54-38.24 | | | |
| Lot 27 (Sample 2) | 7.400 | 14.86 | 27.82 | | | | |
| Lot 27 (Sample 2) | 6.857 | 14.08 | 27.39 | | | | |
| Lot 27 (Sample 2) | 8.117 | 16.58 | 30.90 | | | | |

TABLE 42

Number-Weighted Distribution Parameters

| Formulation | CE Dn10 (µm) | CE Dn50 (µm) | CE Dn90 (µm) | Circle Equivalent (CE)-diameter-range (µm) |
|---|---|---|---|---|
| Lot 27 (Sample 1) | 1.10 | 3.92 | 8.91 | 0.54-49.72 |
| Lot 27 (Sample 1) | 1.14 | 4.06 | 9.61 | 0.54-54.14 |
| Lot 27 (Sample 1) | 0.95 | 4.16 | 9.85 | 0.54-55.04 |
| Lot 27 (Sample 2) | 1.08 | 4.24 | 10.34 | 0.54-42.64 |
| Lot 27 (Sample 2) | 0.85 | 3.71 | 10.52 | 0.54-44.65 |
| Lot 27 (Sample 2) | 0.91 | 4.07 | 10.55 | 0.54-38.24 |

Example: Particle Size Distribution Characterization of Fulvestrant Pharmaceutical Compositions Fulvestrant pharmaceutical compositions F005g5, Lot 27, Lot 28, and Lot 45, described elsewhere herein, were prepared by the methods of preparation shown schematically as process 101 of FIG. 15. Samples of each Lot were prepared using different processes as indicated in Tables 43 to 50 to achieve fulvestrant particle sizes and particle size distributions. The preparation processes are referred to with alphanumeric identifiers, such as "Process A1," "Process A2," and the like, with each process representing a set of fulvestrant-particle-size-reduction steps, as more fully described elsewhere herein, to achieve final fulvestrant particle size and particle size distributions as shown in the Tables 43 to 50. Test samples were evaluated for particle size both prior to drying via lyophilization, which are indicated as "(100× Suspensions)", and after lyophilization and reconstitution, which are indicated as "(100× Reconstituted Suspensions)" in the Tables 43 to 50. Samples were analyzed with a Malvern Morphologi G3 apparatus for microscopy image capture and analysis. CE diameters were measured and volume-weighted particle size distribution parameters were determined. The CE diameter ranges of measurement samples are also shown, with the lower range value of 0.54 microns representing the lower limit of detection for the apparatus setup. Samples were analyzed with a Malvern Mastersizer 3000 apparatus for laser diffraction particle size characterization of LD diameters.

TABLE 43

Volume-Weighted Distribution Parameters
(100x Reconstituted Suspensions)

| Formulation | Process | CE Dv10 (μm) | CE Dv50 (μm) | CE Dv90 (μm) | Circle Equivalent (CE)-diameter-range (μm) |
|---|---|---|---|---|---|
| Lot 27 | Process A1 | 6.606 | 16.14 | 36.36 | 0.54-59.46 |
| | Process A2 | 7.031 | 31.23 | 84.50 | 0.54-107.10 |
| | Process A3 | 6.725 | 24.83 | 53.11 | 0.54-84.16 |
| | Process A4 | 6.790 | 43.74 | 98.32 | 0.54-105.94 |
| Lot 28 | Process B1 | 5.333 | 17.64 | 41.18 | 0.54-53.33 |
| | Process B2 | 4.863 | 12.71 | 42.29 | 0.54-75.19 |
| | Process B3 | 5.376 | 15.85 | 49.64 | 0.54-75.62 |
| | Process B4 | 4.144 | 25.86 | 82.19 | 0.54-107.08 |
| Lot 45 | Process C1 | 8.904 | 35.32 | 66.41 | 0.54-85.05 |
| | Process C2 | 8.135 | 34.79 | 56.77 | 0.54-81.50 |

TABLE 44

Volume-Weighted Distribution Parameters
(100x Reconstituted Suspensions)

| Formulation | Process | CE Dv10 (μm) | CE Dv50 (μm) | CE Dv90 (μm) | Circle Equivalent (CE)-diameter-range (μm) | As-Is LD Dv10 (μm) | As-Is LD Dv50 (μm) | As-Is LD Dv90 (μm) | Sonicated LD Dv10 (μm) | Sonicated LD Dv50 (μm) | Sonicated LD Dv90 (μm) |
|---|---|---|---|---|---|---|---|---|---|---|---|
| Lot 45 | Process C9 | 5.140 | 14.44 | 42.62 | 0.54-71.31 | 3.42 | 8.21 | 33.8 | 2.81 | 5.57 | 10.6 |
| Lot 45 | Process C9 | 6.558 | 17.10 | 44.70 | 0.54-74.57 | 3.37 | 7.81 | 32.6 | 2.82 | 5.58 | 10.5 |
| Lot 45 | Process C9 | 6.648 | 19.97 | 56.47 | 0.54-112.57 | 3.50 | 9.34 | 43.1 | 2.81 | 5.57 | 10.5 |
| Lot 45 | Process C10 | 6.541 | 15.68 | 37.75 | 0.54-55.93 | 3.20 | 7.08 | 24.3 | 2.80 | 5.52 | 10.7 |
| Lot 45 | Process C10 | 5.787 | 13.11 | 32.25 | 0.54-55.82 | 3.33 | 7.83 | 33.9 | 2.98 | 5.80 | 11.1 |
| Lot 45 | Process C10 | 5.375 | 14.59 | 55.02 | 0.54-88.17 | 3.38 | 8.02 | 35.6 | 2.97 | 5.79 | 11.1 |
| F005g5 | As shown in Table 34 | | | | | 3.07 | 29.2 | 95.1 | 2.20 | 5.25 | 14.0 |

TABLE 45

Volume-Weighted Distribution Parameters
(100x Reconstituted Suspensions)

| Formulation | Process | CE Dv10 (μm) | CE Dv50 (μm) | CE Dv90 (μm) | Circle Equivalent (CE)-diameter-range (μm) |
|---|---|---|---|---|---|
| Lot 27 | Process A2 | 4.547 | 11.10 | 33.19 | 0.54-55.75 |
| Lot 27 | Process A2 | 4.290 | 10.15 | 23.66 | 0.54-49.72 |
| Lot 27 | Process A2 | 5.908 | 12.98 | 25.55 | 0.54-42.63 |
| Lot 27 | Process A2 | 6.075 | 12.81 | 23.11 | 0.54-47.71 |
| Lot 27 | Process A2 | 7.022 | 15.59 | 30.94 | 0.54-69.41 |
| Lot 27 | Process A2 | 5.399 | 12.22 | 34.36 | 0.54-51.56 |
| Lot 27 | Process A13 | 4.89 | 11.84 | 32.47 | |
| Lot 27 | Process A13 | 6.46 | 15.33 | 32.47 | |
| Lot 27 | Process A13 | 4.93 | 11.90 | 31.23 | |
| Lot 27 | Process A13 | 5.54 | 14.17 | 50.26 | |
| Lot 27 | Process A13 | 4.19 | 10.16 | 32.22 | |
| Lot 27 | Process A13 | 5.91 | 13.71 | 33.81 | |
| Lot 27 | Process A13 | 5.10 | 13.26 | 45.32 | |
| Lot 27 | Process A13 | 4.61 | 11.47 | 39.79 | |
| Lot 27 | Process A13 | 4.79 | 12.50 | 46.19 | |
| Lot 27 | Process A13 | 4.71 | 10.33 | 22.64 | |
| Lot 27 | Process A13 | 5.66 | 12.66 | 29.72 | |
| Lot 27 | Process A13 | 4.96 | 11.62 | 37.81 | |
| Lot 27 | Process A13 | 4.22 | 12.46 | 42.59 | |
| Lot 27 | Process A13 | 5.80 | 19.69 | 57.80 | |
| Lot 27 | Process A13 | 5.12 | 11.53 | 28.37 | |
| Lot 27 | Process A13 | 3.84 | 9.28 | 32.42 | |
| Lot 27 | Process A13 | 4.64 | 10.32 | 25.28 | |
| Lot 27 | Process A13 | 4.86 | 11.69 | 32.44 | |

TABLE 46

Volume-Weighted Distribution Parameters
(100 x Reconstituted Suspensions)

| Formulation | Process | As-Is LD Dv10 (μm) | As-Is LD Dv50 (μm) | As-Is LD Dv90 (μm) | Sonicated LD Dv10 (μm) | Sonicated LD Dv50 (μm) | Sonicated LD Dv90 (μm) |
|---|---|---|---|---|---|---|---|
| Lot 27 | Process A13 | 2.03 | 8.41 | 36.0 | 1.20 | 3.93 | 7.97 |
| Lot 27 | Process A13 | 1.96 | 7.83 | 35.0 | 1.14 | 3.69 | 7.57 |

TABLE 46-continued

Volume-Weighted Distribution Parameters
(100 × Reconstituted Suspensions)

| | | As-Is | | | Sonicated | | |
|---|---|---|---|---|---|---|---|
| Formulation | Process | LD Dv10 (μm) | LD Dv50 (μm) | LD Dv90 (μm) | LD Dv10 (μm) | LD Dv50 (μm) | LD Dv90 (μm) |
| Lot 27 | Process A13 | 2.08 | 9.14 | 41.3 | 1.20 | 3.92 | 7.94 |
| Lot 27 | Process A13 | 2.10 | 9.65 | 40.3 | 1.15 | 3.66 | 7.53 |
| Lot 27 | Process A13 | 1.67 | 6.10 | 26.5 | 1.08 | 3.42 | 7.19 |
| Lot 27 | Process A13 | 1.70 | 5.71 | 21.6 | 1.17 | 3.80 | 7.78 |
| Lot 27 | Process A13 | 2.53 | 15.8 | 48.4 | 1.27 | 4.07 | 8.72 |
| Lot 27 | Process A13 | 2.01 | 12.6 | 57.6 | 1.01 | 3.04 | 6.85 |
| Lot 27 | Process A13 | 1.62 | 6.34 | 29.5 | 0.96 | 2.76 | 5.89 |

TABLE 47

Volume-Weighted Distribution Parameters
(100x Suspensions)

| Formulation | Process | CE Dv10 (μm) | CE Dv50 (μm) | CE Dv90 (μm) | Circle Equivalent (CE)- diameter- range (μm) |
|---|---|---|---|---|---|
| Lot 27 | Process A15 | 5.199 | 10.4 | 17.52 | 0.54-27.89 |
| | Process A16 | 3.766 | 7.411 | 12.15 | 0.54-25.43 |
| | Process A17 | 3.053 | 6.256 | 10.81 | 0.54-38.27 |
| | Process A18 | 3.727 | 7.277 | 13.91 | 0.54-31.30 |
| Lot 28 | Process B5 | 4.442 | 8.585 | 15.04 | 0.54-41.23 |
| | Process B6 | 4.134 | 7.773 | 13.25 | 0.54-22.59 |
| | Process B7 | 3.835 | 7.311 | 13.11 | 0.54-25.94 |
| | Process B8 | 3.417 | 6.644 | 11.62 | 0.54-28.25 |
| Lot 45 | Process C3 | 7.160 | 14.79 | 25.70 | 0.54-47.55 |
| | Process C4 | 8.587 | 18.15 | 36.68 | 0.54-62.10 |

TABLE 48

Volume-Weighted Distribution Parameters
(100 × Suspensions)

| | | As-Is | | | Sonicated | | |
|---|---|---|---|---|---|---|---|
| Formulation | Process | LD Dv10 (μm) | LD Dv50 (μm) | LD Dv90 (μm) | LD Dv10 (μm) | LD Dv50 (μm) | LD Dv90 (μm) |
| Lot 27 | Process A15 | 1.08 | 3.29 | 7.68 | 0.91 | 2.62 | 6.98 |
| | Process A16 | 1.03 | 3.15 | 7.00 | 0.83 | 2.32 | 5.72 |
| | Process A17 | 0.97 | 2.96 | 6.52 | 0.78 | 2.13 | 5.01 |
| | Process A18 | 0.92 | 2.91 | 6.32 | 0.72 | 1.96 | 4.38 |
| Lot 45 | Process C3 | 1.50 | 6.03 | 12.0 | 0.83 | 2.30 | 5.69 |
| | Process C4 | 1.59 | 5.82 | 11.0 | 0.85 | 2.37 | 5.74 |

TABLE 49

Volume-Weighted Distribution Parameters
(100x Suspensions)

| Formulation | Process | CE Dv10 (μm) | CE Dv50 (μm) | CE Dv90 (μm) | Circle Equivalent (CE)- diameter- range (μm) | As-Is LD Dv10 (μm) | As-Is LD Dv50 (μm) | As-Is LD Dv90 (μm) | Sonicated LD Dv10 (μm) | Sonicated LD Dv50 (μm) | Sonicated LD Dv90 (μm) |
|---|---|---|---|---|---|---|---|---|---|---|---|
| Lot 45 | Process C3 | 12.320 | 29.88 | 57.24 | 0.54-90.58 | 1.51 | 5.40 | 10.7 | 0.80 | 2.11 | 4.64 |
| Lot 45 | Process C4 | 7.454 | 17.37 | 40.29 | 0.54-76.61 | 1.71 | 6.36 | 12.5 | 0.82 | 2.26 | 5.20 |
| Lot 45 | Process C5 | 12.130 | 27.59 | 50.08 | 0.54-87.69 | 1.73 | 6.38 | 12.7 | 0.79 | 2.15 | 4.77 |
| Lot 45 | Process C5 | 8.193 | 17.89 | 35.05 | 0.54-54.50 | 1.63 | 5.85 | 11.7 | 0.79 | 2.13 | 4.68 |
| Lot 45 | Process C5 | 8.690 | 19.36 | 35.53 | 0.54-64.77 | 1.70 | 6.12 | 12.0 | 0.77 | 2.05 | 4.45 |
| Lot 45 | Process C6 | 8.218 | 17.00 | 46.80 | 0.54-80.21 | 1.46 | 4.92 | 9.59 | 1.36 | 4.71 | 9.55 |
| Lot 45 | Process C7 | 6.455 | 14.94 | 38.47 | 0.54-65.55 | 1.27 | 4.21 | 8.61 | 0.77 | 2.11 | 4.66 |
| Lot 45 | Process C8 | 7.795 | 17.20 | 31.60 | 0.54-45.03 | 1.55 | 5.37 | 10.7 | 0.77 | 2.14 | 4.81 |
| Lot 45 | Process C8 | 9.257 | 20.16 | 39.47 | 0.54-84.26 | 1.64 | 5.64 | 11.2 | 0.78 | 2.19 | 4.99 |
| Lot 45 | Process C8 | 10.050 | 21.35 | 36.43 | 0.54-59.43 | 1.59 | 5.55 | 11.1 | 0.76 | 2.10 | 4.66 |

TABLE 50

Volume-Weighted Distribution Parameters
(100 × Suspensions)

| Formulation | Process | CE Dv10 (µm) | CE Dv50 (µm) | CE Dv90 (µm) | Circle Equivalent (CE)- diameter- range (µm) | As-Is LD Dv10 (µm) | As-Is LD Dv50 (µm) | As-Is LD Dv90 (µm) |
|---|---|---|---|---|---|---|---|---|
| Lot 27 | Process A5 | 5.506 | 12.94 | 26.24 | 0.54-52.71 | 1.54 | 5.70 | 11.3 |
| Lot 27 | Process A6 | 8.740 | 19.30 | 35.62 | 0.54-54.43 | 1.42 | 5.10 | 10.1 |
| Lot 27 | Process A7 | 7.862 | 18.92 | 36.09 | 0.54-52.63 | 1.48 | 5.30 | 10.4 |
| Lot 27 | Process A8 | 8.184 | 17.49 | 33.02 | 0.54-63.56 | 1.46 | 5.04 | 9.69 |
| Lot 27 | Process A9 | 7.451 | 15.99 | 29.94 | 0.54-55.58 | 1.49 | 5.00 | 9.65 |
| Lot 27 | Process A10 | 7.673 | 18.50 | 36.71 | 0.54-74.22 | 1.59 | 5.55 | 10.6 |
| Lot 27 | Process A11 | 9.093 | 20.01 | 45.26 | 0.54-61.26 | 1.72 | 6.11 | 12.1 |
| Lot 27 | Process A12 | 6.355 | 14.92 | 46.31 | 0.54-63.98 | 1.66 | 5.77 | 10.9 |
| Lot 27 | Process A13 | 7.029 | 15.66 | 31.06 | 0.54-55.89 | 1.07 | 3.51 | 7.32 |
| Lot 27 | Process A14 | 7.870 | 20.15 | 43.79 | 0.54-62.35 | 1.74 | 5.87 | 11.0 |
| Lot 27 | Process A14 | 8.499 | 19.06 | 37.90 | 0.54-70.88 | 1.67 | 5.49 | 10.5 |
| Lot 27 | Process A14 | 8.072 | 17.43 | 30.90 | 0.54-56.50 | 1.76 | 6.01 | 11.5 |
| Lot 27 | Process A14 | 8.078 | 18.98 | 45.32 | 0.54-69.82 | 1.81 | 6.43 | 12.5 |

When ranges are used herein for chemical or physical properties, such as particle size or particle size distribution, formulation component concentrations, or pharmacokinetic properties, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of forming an aqueous fulvestrant suspension comprising:
   mixing an aqueous medium and at least one stabilizer to form a suspension vehicle, the at least one stabilizer comprising:
   a surfactant and
   a polyvinylpyrrolidone, polyethylene glycol with an average molecular weight of about 3350 g/mol, a carboxymethylcellulose sodium, a non-electrolyte, or a combination thereof;
   adding an amount of fulvestrant to the suspension vehicle; and
   dispersing the fulvestrant in the suspension vehicle to form an aqueous fulvestrant suspension;
   wherein the aqueous fulvestrant suspension comprises fulvestrant particles having one or more of:
   a laser diffraction determined (LD) Dv(10) from about 1 micron to about 3 microns;
   an LD Dv(50) from about 2 microns to about 35 microns; and
   an LD Dv(90) from about 4 microns to about 120 microns;
   and having one or more of:
   a microscopy image capture determined (CE) Dv(90) from about 10 microns and about 200 microns;
   a CE Dv(50) from about 5 microns to about 60 microns; and
   CE Dv(10) from about 1 microns to about 25 microns.

2. The method of claim 1, further comprising high pressure homogenizing the aqueous fulvestrant suspension.

3. The method of claim 2, wherein the high pressure homogenization is performed at a pressure of about 15,000 psi to about 45,000 psi.

4. The method of claim 2, further comprising adding an electrolyte to the homogenized aqueous fulvestrant suspension and mixing the electrolyte into the suspension.

5. The method of claim 2, further comprising adding another non-electrolyte to the homogenized aqueous fulvestrant suspension and mixing the other non-electrolyte into the suspension.

* * * * *